US009958458B2

(12) United States Patent
Amenta et al.

(10) Patent No.: US 9,958,458 B2
(45) Date of Patent: *May 1, 2018

(54) THERAPEUTIC AND DIAGNOSTIC METHODS INVOLVING BIGLYCAN AND UTROPHIN

(75) Inventors: Alison R. Amenta, Pawtucket, RI (US); Atilgan Yilmaz, Providence, RI (US); Beth A. McKechnie, Franklin, MA (US); Justin R. Fallon, Harvard, MA (US)

(73) Assignee: Brown University, Providence, RI (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 13/996,951

(22) PCT Filed: Dec. 27, 2011

(86) PCT No.: PCT/US2011/067432
§ 371 (c)(1),
(2), (4) Date: Oct. 23, 2013

(87) PCT Pub. No.: WO2012/092299
PCT Pub. Date: Jul. 5, 2012

(65) Prior Publication Data
US 2014/0038906 A1     Feb. 6, 2014

Related U.S. Application Data

(60) Provisional application No. 61/427,468, filed on Dec. 27, 2010.

(51) Int. Cl.
| *A61K 38/00* | (2006.01) |
| *G01N 33/68* | (2006.01) |
| *A61K 38/17* | (2006.01) |
| *A61K 45/06* | (2006.01) |
| *A61K 31/4985* | (2006.01) |
| *A61K 31/635* | (2006.01) |
| *A61K 38/39* | (2006.01) |

(52) U.S. Cl.
CPC ..... *G01N 33/6893* (2013.01); *A61K 31/4985* (2013.01); *A61K 31/635* (2013.01); *A61K 38/1709* (2013.01); *A61K 38/1719* (2013.01); *A61K 38/39* (2013.01); *A61K 45/06* (2013.01); *G01N 2800/2878* (2013.01); *G01N 2800/2885* (2013.01); *G01N 2800/2892* (2013.01); *G01N 2800/52* (2013.01)

(58) Field of Classification Search
None
See application file for complete search history.

(56) References Cited

U.S. PATENT DOCUMENTS

| 5,340,934 A | 8/1994 | Termine et al. |
| 5,654,270 A | 8/1997 | Ruoslahti |
| 5,705,609 A | 1/1998 | Ruoslahti et al. |
| 6,864,236 B1 | 3/2005 | Fallon et al. |
| 7,335,637 B2 | 2/2008 | Fallon et al. |
| 7,612,038 B2 | 11/2009 | Fallon et al. |
| 7,759,314 B2 | 7/2010 | Fallon et al. |
| 7,816,322 B2 | 10/2010 | Fallon et al. |
| 8,138,154 B2 | 3/2012 | Fallon et al. |
| 8,367,619 B2 | 2/2013 | Wight et al. |
| 8,658,596 B2 | 2/2014 | Fallon et al. |
| 8,691,766 B2 | 4/2014 | Fallon et al. |
| 8,822,418 B2 | 9/2014 | Fallon et al. |
| 2004/0063627 A1 | 4/2004 | Fallon et al. |
| 2005/0059580 A1 | 3/2005 | Fallon et al. |
| 2008/0274966 A1 | 11/2008 | Fallon et al. |
| 2010/0130405 A1 | 5/2010 | Fallon et al. |
| 2011/0053854 A1 | 3/2011 | Fallon et al. |
| 2011/0183910 A1 | 7/2011 | Fallon et al. |
| 2012/0245095 A1 | 9/2012 | Fallon et al. |
| 2014/0213523 A1 | 7/2014 | Fallon et al. |

FOREIGN PATENT DOCUMENTS

| EP | 0 686 397 A2 | 4/1995 |
| WO | WO-93/10808 A1 | 6/1993 |
| WO | WO-95/13298 A1 | 5/1995 |

(Continued)

OTHER PUBLICATIONS

Amenta, A. R. "Biglycan at synapses, the sarcolemma and as a potential therapeutic for Duchenne Muscular Dystrophy", PhD Thesis, 2007, Dept of neuroscience, Brown University, Providence, Rhode Island, USA.*
Amenta et al., "Biglycan Recruits Utrophin to the Sarcolemma and Counters Dystrophic Pathology in MDX Mice," *Proc Natl. Acad. Sci. USA*, 108(2):762-767 (2011).
Ameye, "Mice Deficient in Small Leucine-Rich Proteoglycans: Novel In Vivo Models for Osteoporosis, Osteoarthritis, Ehlers-Danlos Syndrome, Muscular Dystrophy, and Corneal Diseases," *Glycobiology*, 12(9):107R-116R (2002).
Athanasopoulos et al., "Recombinant adeno-associated viral (rAAV) vectors as therapeutic tools for Duchenne muscular dystrophy (DMD)," Gene Therapy 11:S109-S121 (2004).

(Continued)

*Primary Examiner* — Olga N Chernyshev
(74) *Attorney, Agent, or Firm* — Foley Hoag LLP

(57) ABSTRACT

The present disclosure provides methods for predicting a patient's response to biglycan therapy for diseases or conditions associated with an abnormal level or activity of biglycan; disorders associated with an unstable cytoplasmic membrane, for example, due to an unstable dystrophin associated protein complex (DAPC); disorders associated with abnormal synapses or neuromuscular junctions, including those resulting from an abnormal MuSK activation or acetylcholine receptor (AChR) aggregation. Examples of such diseases include muscular dystrophies, such as Duchenne's Muscular Dystrophy, Becker's Muscular Dystrophy, neuromuscular disorders and neurological disorders. This application also provides combination therapeutics, such as a biglycan therapeutic and a utrophin therapeutic.

3 Claims, 30 Drawing Sheets

(56) References Cited

FOREIGN PATENT DOCUMENTS

| WO | WO-00/54801 | 9/2000 |
|---|---|---|
| WO | WO-0125461 A1 | 4/2001 |
| WO | WO-01/036475 A2 | 5/2001 |
| WO | WO-03/015615 A2 | 2/2003 |
| WO | WO 03/070195 | 8/2003 |
| WO | WO-2007/088050 A2 | 8/2007 |
| WO | WO-2007/123848 | 11/2007 |
| WO | WO2008014458 | 1/2008 |
| WO | WO-2008/100789 | 8/2008 |
| WO | WO-2011/146480 A1 | 11/2011 |

OTHER PUBLICATIONS

Balaban et al., "Corticosterois treatment and functional improvement in Duchenne muscular dystrophy: long-term effect," American Journal of Physical Medicine & Rehabilitation / Assoc. of AcAdemic Physiatrists, 84:11 843-850 (2005).

Bianco et al., "Expression and Localization of the Two Small Proteoglycans Biglycan and Decorin in Developing Human Skeletal and Non-Skeletal Tissues," *J. Histochem. Cytochem.*, 38(11):1549-1563 (1990).

Bonaldo et al., "Collagen VI deficiency induces early onset myopathy in the mouse: an animal model for Bethlem myopathy," Human Molecular Genetics 7:13 2134-2140 (1998).

Bowe et al., "The Small Leucine-Rich Repeat Proteoglycan Biglycan Binds to Alpha-Dystroglycan and is Upregulated in Dystrophic Muscle," *J. Cell Biol.*, 148(4):801-810 (2000).

Brandan et al., "Novel Regulatory Mechanisms for the Proteoglycans Decorin and Biglycan During Muscle Formation and Muscular Dystrophy," *Matrix Biol.*, 27:700-708 (2008).

Brown. "Hybridization Analysis of DNA Blots," Unit 2.10, Current Protocols in Molecular Biology, John Wiley & Sons (2003).

Casar et al., "Transient Up-Regulation of Biglycan During Skeletal Muscle Regeneration: Delayed Fiber Growth Along with Decorin Increase in Biglycan-Deficient Mice," Dev. Biol., 268:358-371 (2004).

Chan, Yiu-mo et al., "Molecular Organization of Sarcoglycan Complex in Mouse Myotubes in Culture." J. Cell Bio. 143, 2033-2044 (Dec. 28, 1998).

Coral-Vasquez, R. et al. Disruption of the Sarcoglycan-Sarcospan Complex in Vascular Smooth Muscle: A Novel Mechanism for Cardiomyopathy and Muscular Dystrophy. Cell 98, 465-74 (1999).

Crosbie, Rachelle H. et al. Membrane Targeting and Stabilizatoin of Sarcospan is Mediated by the Saroglycan Subcomplex. J. Cell. Biol. 145, 159-165 (Apr. 5, 1999).

Ervasti et al., A Role for the Dystrophin-Glycoprotein Complex as a Transmembrane Linker between Laminin and Actin. J. Cell Biol. 122, 809-823 (Aug. 1993).

Farooqi et al., Effects of Recombinant Leptin Therapy in a Child with Congenital Leptin Deficiency, N. E. Journal of Medicine, 341: 879-884 (1999).

Ferri, R. T. et al. A Role for Biglycan in Agrin-Induced Postsynaptic Differentiation. Society for Neuroscience Abstracts 26 (2000) [Abstract Only].

Fisher et al. as "Deduced Protein Sequence of Bone Small Proteoglycan I (Biglycan Shows Homology with Proteoglycan II (Decorin) and Several Nonconnective Tissue Proteins in a Variety of Species," J. Biol. Chem., 264(8): 4571-4576 (1996).

Fukuta et al. "Molecular Cloning and Expression of Chick Chondrocyte Chondroitin 6-Sulfotransferase," *J. Biol. Chem.*, 270(31)18575-18580 (1995).

Gee, Stephen H. et al. Dystroglycan-a, a Dystrophin-Associated Glycoprotein, is a Functional Agrin Receptor. Cell 77, 675-686 (Jun. 3, 1994).

Gregorevic et al., "Gene therapy for muscular dystrophy—a review of promising progress," Expert Opin Biol Ther., 3(5) 803-14 (2003).

Guglieri, et al., "Molecular Etiopathogenesis of Limb Girdle Muscular and Congenital Muscular Dystrophies: Boundaries and Contiguities," Clinica Chimica Acta 361 (2005) 54-79.

Hammond et al., "PRO-051, an antisense oligonucleotide for the potential treatment of Duchenne muscular dystrophy" Current Opinion in Molecular Therapeutics, 12:4 478-486 (2010).

Hasenohrl et al., "Facilitation of learning following injection of the chondroitin sulfate proteoglycan biglycan into the vicinity of the nucleus basalis magnocellularis," Behavioural Brain Research, 70:59-67 (1995).

Hildebrand et al., "Interaction of the Small Intestitial Proteoglycans Biglycan, Decorin and Fibromodulin with Transforming growth Factor Beta," *J. Biochem.*, 302:527-534 (1994).

Hoch, Werner. Formation of the Neuromuscular Junction: Agrin and its unusual receptors. Eur. J. Biochem. 265, 1-10(1999).

Hocking et al., "Eukaryotic Expression of Recombinant Biglycan; Post-Translational Processing and the Importance of Secondary Structure for Biological Activity," *J. Biol. Chem.* 271: 19571-19577 (1996).

Hocking et al., "Leucine-rich Repeat Glycoproteins of the Extracellular Matrix," *Matrix Biol.*, 17(1):1-19 (1998).

Holt, Kathleen H. et al. Functional Rescue of the Sarcoglycan Complex in the BIO 14.6 Hamster Using S-Sarcoglycan Gene Transfer. Mol. Cell 1, 841-848 (May 1998).

Hwang et al., "Retrovirally Mediated Overexpression of Gylycosaminoglycan-Deficient Biglycan in Arterial Smooth Muscle Cells Induces Tropoelastin Synthesis and Elastic Fiber Formation in Vitro and in Neointimae after Vascular Injury", Am J. Pathol. 173(6):1919-1928 (2008).

Ibraghimov-Beslrovanaya et al. Human Dystroglycan: Skeletal Muscle cDNA, Genomic Structure, Origin of Tissue Specific Isoforms and Chromosomal Localization. Hum. Mol. Genet. 2, 1651-1657 (1993).

Iozzo, R. Matrix Proteoglycans: From Molecular Design to Cellular Function. Ann. Rev. Biochem. 67, 609-652 (1998).

Jarvelainen, Hannu T. et al. Differential Expression of Small Chondroitin/Dermatan Sulfate Proteoglycans, PG-I/Biglycan and PG-II/Decorin, by Vascular Smooth Muscle and Endothelial Cells in Culture. J. Biol. Chem. 266, 23274-23281 (Dec. 5, 1991).

Junghans, Ulrich et al. Purification of a Meningeal Cell-derived Chondroitin Sulphate Proteoglycan with Neurotrophic Activity for Brain Neurons and its Identification as Biglycan. Euro. J. Neurosci. 7, 2341-2350 (1995).

Khan, M.A. "Corticosteroid therapy in Duchenne muscular dystrophy" Journal of the Neurological Sciences, 120:1, 8-14 (1993).

King, W.M. et al. "Orthopedic outcomes of long-term daily corticosteroid treatment in Duchenne muscular dystrophy" Neurology, 68(19): 1607-1613 (2007).

Khurana, T. S. et al. Interaction of ARIA, a Neuregulin, with the Dystroglycan / Sarcoglycan Complex in Skeletal Muscle. Mol. Cell. Biol. 7, 314 (1996).

Kobe & Deisenhofer, "The Leucine-Rich Repeat: a Versatile Binding Motif," *Trends Biochem. Sci.*, 19(10):415-421 (1994).

Kresse et al., "Different Usage of the Glycosaminoglycan Attachment Sites of Biglycan," *J. Biol. Chem.*, 276(16):13411-13416 (2001).

Krishnan, P. et al., "Distinct Secondary Structures of the Leucinerich Repeat Proteoglycans Decorin and Biglycan." J. Biol. Chem. 274, 10945-50 (1999).

Krivickas, L.S. et al. "Single muscle fiber contractile properties in adults with muscular dystrophy treated with MYO-029" Muscle & Nerve, 39:1 309 (2009).

Lamandé et al., "Reduced collagen VI causes Bethlem myopathy: a heterozygous COL6A1 nonsense mutation results in mRNA decay and functional haploinsufficiency," Human Molecular Genetics, 7:6 (981-989 (1998).

Lampe et al., "Collagen VI Related Muscle Disorders," J. Med. Genet. 2005;42;673-685.

Langton, et al., "Localization of the Functional Domains of Human Tissue Inhibitor of Metalloproteinases-3 and the Effects of a Sorsby's Fundus Dystropy Mutation," The Journal of Biological Chemistry, 273:16778-16781 (1998).

Lechner et al., "Developmental Regulation of Biglycan Expression in Muscle and Tendon," Muscle Nerve, 34:347-355 (2006).

(56) References Cited

OTHER PUBLICATIONS

Matthews D.J. et al. "Use of corticosteroids in a population-based cohort of boys with Duchenne and Becker muscular dystrophy", Journal of Child Neurology, 25:11, 1319-1324 (2010).

Mercado et al., "Biglycan Regulates the Expression and Sarcolemmal Localization of Dystrobrevin, Syntrophin, and nNOS," FASEB Journal, 20:E1075-E1085 (2006).

Moreth et al., "The Proteoglycan Biglycan Regulates Expression of the B Cell Chemoattractant CXCL13 and Aggravates Murine Lupus Nephritis," *J. Clin. Invest.*, 120(12):4251-4272 (2010).

Nastuk et al., "Expression Cloning and Characterization of NSIST, a Novel Sulfotransferase Expressed by a Subset of Neurons and Postsynaptic Targets," *J. Neuroscience*, 18(18)7167-7177 (1998).

O'Brien et al., "Smooth Muscle Cell Biglycan Overexpression Results in Increased Lipoprotein Retention on Extracellular Matrix: Implications for the Retention of Lipoproteins in Atherosclerosis," Altherosclerosis, 177L29-35 (2004).

O'Toole et al., "Alternative splicing of agrin regulates its binding to heparin, a-dystroglycan, and the cell surface," Proc. Natl. Acad. Sci 93: 7369-7374 (1996).

Peat et al., "Exclusion of Biglycan Mutations in a Cohort of Patients With Neuromuscular Disorders," Neuromuscul Disord., 18(8):606-609 (2008).

Rafii et al, "Biglycan Binds to α- and γ-Sarcoglycan and Regulates Their Expression During Development," *J. Cell Physiol.*, 209(2):439-447 (2006).

Rafii et al., "Interactions of the Proteoglycan Biglycan with the Dystrophin Associated Protein Complex and its Roles in Muscular Dystrophy and Synaptogenesis," (Abstract from 40th American Society for Cell Biology Annual Meeting) Molecular Biology of the Cell, 11:146a (2000).

Rühland et al., The Glycosaminoglycan Chain of Decorin Plays an Important Role in Collagen Fibril Formation at Early Stages of Fibrillogenesis, The FEBS Journal, 274:4246-4255 (2007).

Sakamoto, Aiji et al. Both hypertrophic and dilated cardiomyopathies are caused by mutation of the same gene, S-sarcoglycan, in hamster. An animal model of disrupted dystrophin-associated glycoprotein complex. PNAS 94: 13873-13878 (Dec. 1997).

Schaefer et al., "Biological Functions of the Small Leucine-rich Proteoglycans: From Genetics to Signal Transduction," *J. Biol. Chem.*, 283(31):21305-21309 (2008).

Scott et al., "Crystal Structure of the Biglycan Dimer and Evidence That Dimerization is Essential for Folding and Stability of Class I Small Leucine-rich Repeat Proteoglycans," *J. Biol. Chem.*, 281(19):13324-13332 (2006).

Smythe et al., "Altered caveolin-3 expression disrupts PI(3) kinase signaling leading to death of cultured muscle cells," Experimental Cell Research, 312:15 2816-2825 (2006).

Speer et al., "Evidence for locus heterogeneity in the Bethlem myopathy and linkage to 2q37," Hum. Mol. Genet. 1996, 5(7): 1043-6.

Spence et al., "Muscular dystrophies, the cytoskeleton and cell adhesion," BioEssays 24:542-552, 2002.

Tomoyasu, Hiroshi et al. Identification of haemopoietic biglycan in hyperplastic thymus associated with myasthenia gravis, J. Neuroimmunology, 89, 59-63 (1998).

Vanegas et al., "Ullrich scleroatonic muscular dystrophy is caused by recessive mutations in collagen type VI," PNAS, 98(13):7516-7521 (2001).

Von der Mark et al., "Immunochemistry, genuine size and tissue localization of collagen VI," Eur. J. Biochem. 142(3):493-502, 1984.

Wiberg et al., "Biglycan and Decorin Bind Close to the N-terminal Region of the Collagen VI Triple Helix," J. Biol. Chem., 276;22, 18947-18952, 2001.

Winder, Steven J. The complexitites of dystroglycan. Trends in Biochem. Sci. 26, 118-124 (2001).

Xu et al., "Targeted Disruption of the Biglycan Gene Leads to an Osteoporosis-Like Phenotype in Mice," *Nature Genetics*, 20:78-82 (1998).

Adamo et al., "Sildenafil reverses cardiac dysfunction in the mdx mouse model of Duchenne muscular dystrophy," Proc. of the National Academy of Sciences USA, 107:19079-19083 (Nov. 2010).

Cadena et al., "Administration of a soluble activin type IIB receptor promotes skeletal muscle growth independent of fiber type," Journal of Applied Physiology, 109:635-642 (Sep. 2010).

Zhou et al., "Targeting Fibrosis in Duchenne Muscular Dystrophy," Journal of Neuropathology and Experimental Neurology, 69:771-776 (Aug. 2010).

Fadic et al., Increase in decorin and biglycan in Duchenne Muscular Dystrophy: role of fibroblasts as cell source of these proteoglycans in the disease. J. Cell. Mol. Med. 10:3, 758-769 (Jul. 3, 2006).

Gramolini et al., "Muscle and Neural Isoforms of Agrin Increase Utrophin Expression in Cultured Myotubes via a Transcriptional Regulatory Mechanism," Journal of Biological Chemistry, 272(2): 736-743 (1998).

Miura et al., "Utrophin upregulation for treating Duchenne or Becker muscular dystrophy: how close are we?" Trends in Molecular Medicine, Elsevier Current Trends, GB, 12(3) 122-129 (2006), XP028058695, ISSN: 1471-4914, DOI.

Nguyen, et al., "Utrophin, the autosomal homologue of dystrophin, is widely-expressed and membrane-associated in cultured cell lines," FEBS Letters, 313(1) 19-22 (1992).

Buxbaum et al., "Processing of Alzheimer beta/A4 amyloid precursor protein: modulation by agents that regulate protein phosphorylation," Proc. Nat. Acad. Sci., 87:6003-6006 (1990).

Yoshida et al., "Bidirectional Signaling Between Sarcoglycans and the Integrin Adhesion System in Cultured L6 Myocytes", The Journal of Biological Chemistry, 273(3):1583-1590 (1998).

Amenta et al., "Systemically-Administered Biglycan Upregulates Utrophin and Counters Dystrophic Pathology in MDXZ Mice: A Novel Pharmacological Approach for DMD Therapy," Neuromuscular Disorders, Pergamon Press GB 17(9-10):804 (2007).

\* cited by examiner a.
*mdx:utrn<sup>-/-</sup>*
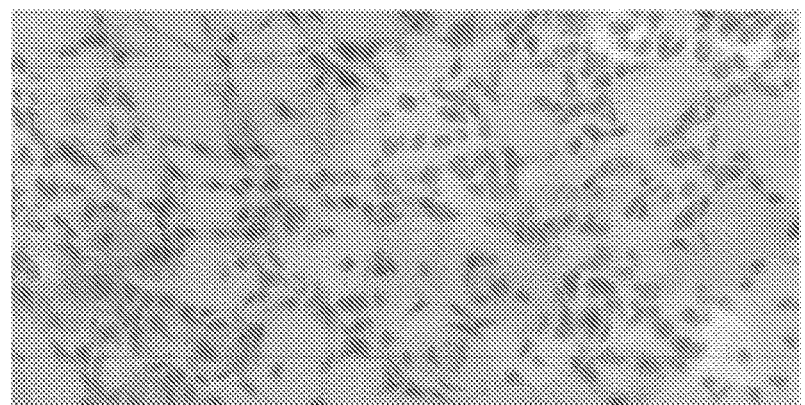
Vehicle
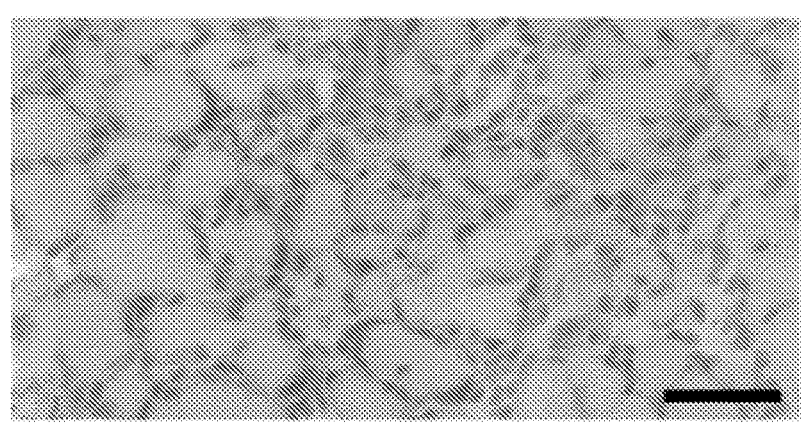
rhBGN
b.
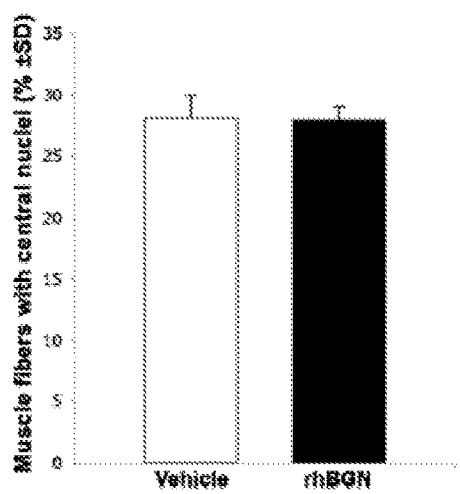
FIG. 10

- GAG addition sites
- Y – N-linked carbohydrate (a)
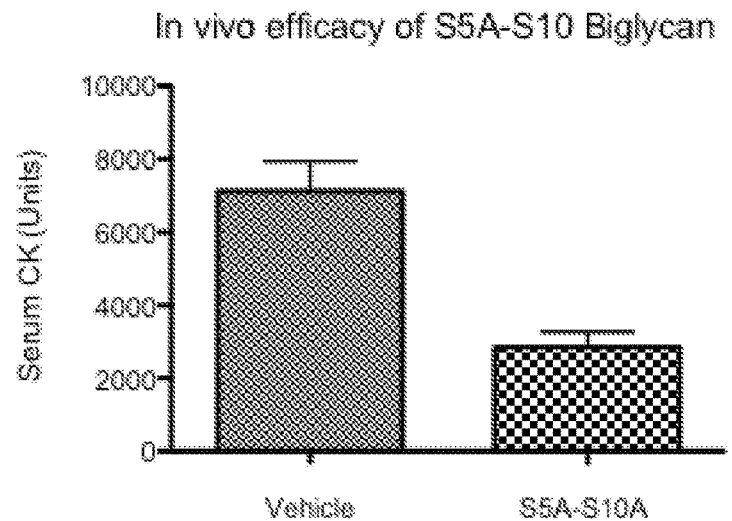
(b)
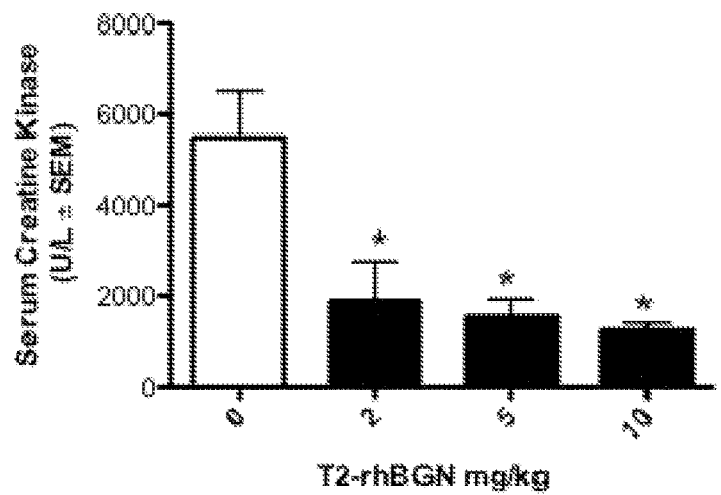
FIG. 19

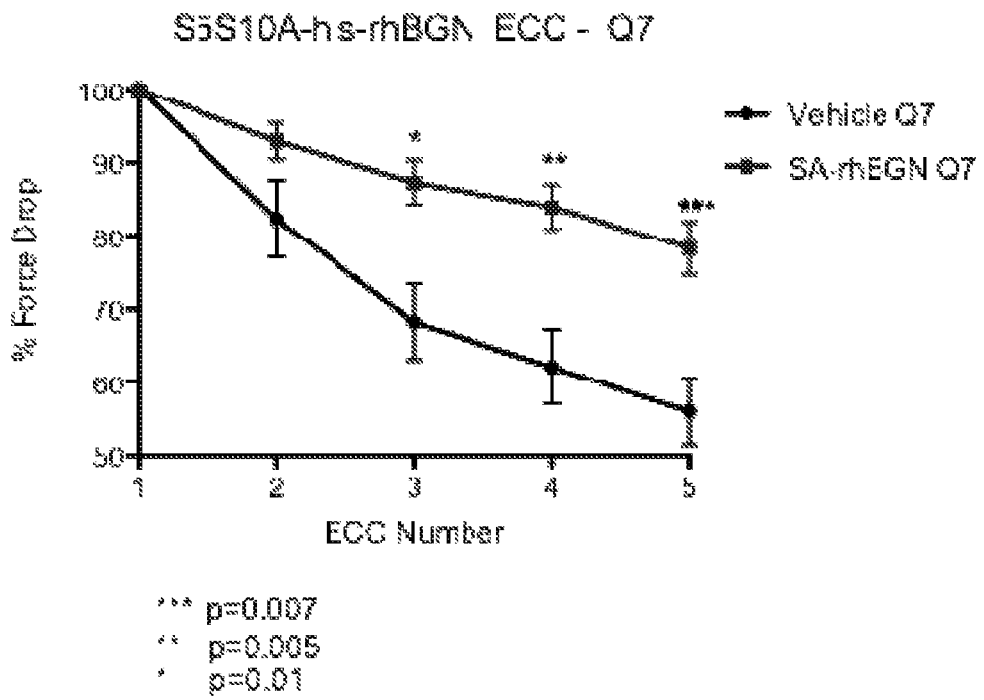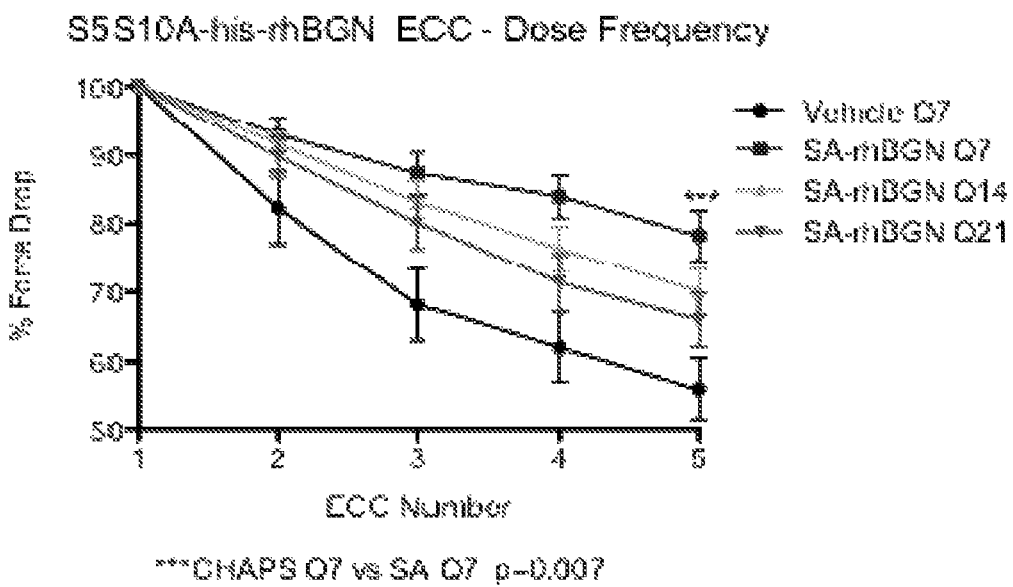
FIG. 20

Improved muscle health in mdx mice injected with SA-rhBGN

A.
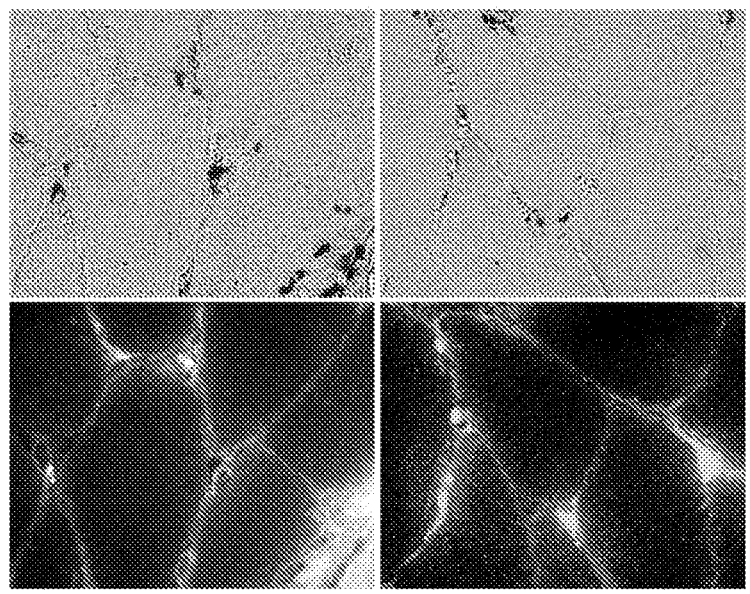
B.
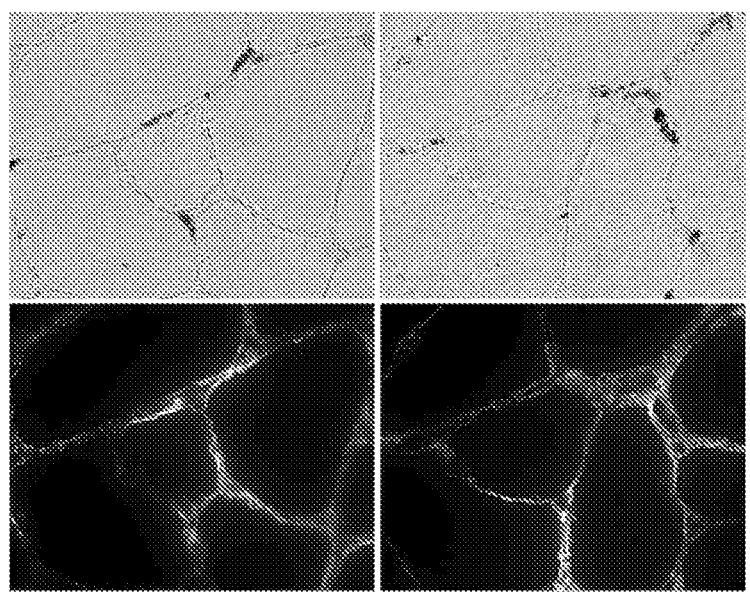
FIG. 22

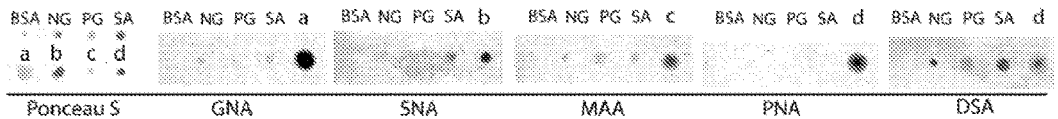

| Lectin | Binding Preference | Proteoglycan (PG) | Non-glycanated (NG) | Mutant (SA) |
|---|---|---|---|---|
| GNA (Galanthus nivalis agglutinin) | Terminal Man; (1-3), (1-6) or (1-2) | - | + | + |
| SNA (Sambucus nigra agglutinin) | Sialic acid linked (2-6) to Gal or GalNAc | - | + | + |
| MAA (Maackia amurensis agglutinin) | Sialic acid linked (2-3) to Gal | + | + | + |
| PNA (Peanut agglutinin) | Galβ(1-3)GalNAc | - | - | - |
| DSA (Datura stramonium agglutinin) | Galβ(1-4)GlcNAc or terminal GlcNAc | + | + | + |

FIG. 23

| Nonglycanated (NG) Biglycan | | |
|---|---|---|
| Sequon | Peptide Position | Peptide Sequence[a] |
| Asn$^{270}$ | 267-280 | (R)MIEN@GSLSFLPTLR(E) |
| Asn$^{311}$ | 301-314 | (K)LLQVVYLHSNN@ITK(V) |

| Mutant (SA) Biglycan | | |
|---|---|---|
| Sequon | Peptide Position | Peptide Sequence[a] |
| Asn$^{270}$ | 267-280 | (R)MIEN@GSLSFLPTLR(E) |
| Asn$^{311}$ | 301-314 | (K)LLQVVYLHSNN@ITK(V) |

[a] An @ indicates the site of N-glycosylation

Sequon → Asn-X-Ser or Asn-X-Thr

FIG. 24

SEQUENCE LISTING

<160> NUMBER OF SEQ ID NOS: 17

<210> SEQ ID NO 1
<211> LENGTH: 9
<212> TYPE: PRT
<213> ORGANISM: Torpedo californica

<400> SEQUENCE: 1

Ile Gln Ala Ile Glu Phe Glu Asp Leu
1               5

<210> SEQ ID NO 2
<211> LENGTH: 9
<212> TYPE: PRT
<213> ORGANISM: Torpedo californica

<400> SEQUENCE: 2

Leu Gly Leu Gly Phe Asn Glu Ile Arg
1               5

<210> SEQ ID NO 3
<211> LENGTH: 19
<212> TYPE: PRT
<213> ORGANISM: Torpedo californica

<400> SEQUENCE: 3

Thr Ser Tyr His Gly Ile Ser Leu Phe Asn Asn Pro Val Asn Tyr Trp
1               5                   10                  15

Asp Val Leu

<210> SEQ ID NO 4
<211> LENGTH: 9
<212> TYPE: PRT
<213> ORGANISM: Homo sapiens

<400> SEQUENCE: 4

Ile Gln Ala Ile Glu Leu Glu Asp Leu
1               5

<210> SEQ ID NO 5
<211> LENGTH: 9
<212> TYPE: PRT
<213> ORGANISM: Homo sapiens

<400> SEQUENCE: 5

Leu Gly Leu Gly His Asn Gln Ile Arg
1               5

<210> SEQ ID NO 6
<211> LENGTH: 19
<212> TYPE: PRT
<213> ORGANISM: Homo sapiens

<400> SEQUENCE: 6

Ala Tyr Tyr Asn Gly Ile Ser Leu Phe Asn Asn Pro Val Pro Tyr Trp
1               5                   10                  15

Glu Val Gln

<210> SEQ ID NO 7
<211> LENGTH: 1685
<212> TYPE: DNA
<213> ORGANISM: Homo sapiens

<400> SEQUENCE: 7

| | | | | | |
|---|---|---|---|---|---|
| gagtagctgc | tttcggtccg | ccggacacac | cggacagata | gacgtgcgga | cggcccacca | 60 |
| ccccagcccg | ccaactagtc | agcctgcgcc | tggcgcctcc | cctctccagg | tccatccgcc | 120 |
| atgtggcccc | tgtggcgcct | cgtgtctctg | ctggccctga | gccaggccct | gccctttgag | 180 |
| cagagaggct | tctgggactt | caccctggac | gatgggccat | tcatgatgaa | cgatgaggaa | 240 |
| gcttcgggcg | ctgacacctc | aggcgtcctg | gacccggact | ctgtcacacc | cacctacagc | 300 |
| gccatgtgtc | ctttcggctg | ccactgccac | ctgcgggtgg | ttcagtgctc | cgacctgggt | 360 |
| ctgaagtctg | tgcccaaaga | gatctcccct | gacaccacgc | tgctggacct | gcagaacaac | 420 |
| gacatctccg | agctccgcaa | ggatgacttc | aagggtctcc | agcacctcta | cgccctcgtc | 480 |
| ctggtgaaca | acaagatctc | caagatccat | gagaaggcct | tcagcccact | gcggaagctg | 540 |
| cagaagctct | acatctccaa | gaaccacctg | gtggagatcc | cgcccaacct | acccagctcc | 600 |
| ctggtggagc | tccgcatcca | cgacaaccgc | atccgcaagg | tgcccaaggg | agtgttcagc | 660 |
| gggctccgga | acatgaactg | catcgagatg | ggcgggaacc | cactggagaa | cagtggcttt | 720 |
| gaacctggag | ccttcgatgg | cctgaagctc | aactacctgc | gcatctcaga | ggccaagctg | 780 |
| actggcatcc | ccaaagacct | ccctgagacc | ctgaatgaac | tccacctaga | ccacaacaaa | 840 |
| atccaggcca | tcgaactgga | ggacctgctt | cgctactcca | agctgtacag | gctgggccta | 900 |

```
ggccacaacc agatcaggat gatcgagaac gggagcctga gcttcctgcc caccctccgg    960
gagctccact tggacaacaa caagttggcc agggtgccct cagggctccc agacctcaag   1020
ctcctccagg tggtctatct gcactccaac aacatcacca aagtgggtgt caacgacttc   1080
tgtcccatgg gcttcggggt gaagcgggcc tactacaacg gcatcagcct cttcaacaac   1140
cccgtgccct actgggaggt gcagccggcc actttccgct gcgtcactga ccgcctggcc   1200
atccagtttg caactacaa aaagtagagg cagctgcagc caccgcgggg cctcagtggg   1260
ggtctctggg gaacacagcc agacatcctg atggggaggc agagccagga agctaagcca   1320
gggcccagct gcgtccaacc cagcccccca cctcaggtcc ctgaccccag ctcgatgccc   1380
catcaccgcc tctccctggc tcccaagggt gcaggtgggc gcaaggcccg gcccccatca   1440
catgttccct tggcctcaga gctgcccctg ctctcccacc acagccaccc agaggcaccc   1500
catgaagctt ttttctcgtt cactcccaaa cccaagtgtc caaagctcca gtcctaggag   1560
aacagtccct gggtcagcag ccaggaggcg gtccataaga atggggacag tgggctctgc   1620
cagggctgcc gcacctgtcc agaacaacat gttctgttcc tcctcctcat gcatttccag   1680
ccttg                                                               1685
```

<210> SEQ ID NO 8
<211> LENGTH: 1104
<212> TYPE: DNA
<213> ORGANISM: Homo sapiens

<400> SEQUENCE: 8

```
atgtggcccc tgtggcgcct cgtgtctctg ctggccctga gccaggccct gccctttgag     60
cagagaggct tctgggactt caccctggac gatgggccat tcatgatgaa cgatgaggaa    120
gcttcgggcg ctgacacctc aggcgtcctg gacccggact ctgtcacacc cacctacagc    180
gccatgtgtc ctttcggctg ccactgccac ctgcgggtgg ttcagtgctc cgacctgggt    240
ctgaagtctg tgcccaaaga gatctcccct gacaccacgc tgctggacct gcagaacaac    300
gacatctccg agctccgcaa ggatgacttc aagggtctcc agcacctcta cgccctcgtc    360
ctggtgaaca acaagatctc caagatccat gagaaggcct tcagcccact gcggaagctg    420
cagaagctct acatctccaa gaaccacctg gtggagatcc cgccaacct acccagctcc    480
ctggtggagc tccgcatcca cgacaaccgc atccgcaagg tgcccaaggg agtgttcagc    540
gggctccgga catgaactg catcgagatg gcgggaacc cactggagaa cagtggcttt    600
gaacctggag ccttcgatgg cctgaagctc aactacctgc gcatctcaga ggccaagctg    660
actggcatcc ccaaagacct ccctgagacc ctgaatgaac tccacctaga ccacaacaaa    720
atccaggcca tcgaactgga ggacctgctt cgctactcca agctgtacag gctgggccta    780
ggccacaacc agatcaggat gatcgagaac gggagcctga gcttcctgcc caccctccgg    840
gagctccact tggacaacaa caagttggcc agggtgccct cagggctccc agacctcaag    900
ctcctccagg tggtctatct gcactccaac aacatcacca aagtgggtgt caacgacttc    960
tgtcccatgg gcttcggggt gaagcgggcc tactacaacg gcatcagcct cttcaacaac   1020
cccgtgccct actgggaggt gcagccggcc actttccgct gcgtcactga ccgcctggcc   1080
atccagtttg caactacaa aaag                                           1104
```

<210> SEQ ID NO 9
<211> LENGTH: 368
<212> TYPE: PRT
<213> ORGANISM: Homo sapiens

<400> SEQUENCE: 9

```
Met Trp Pro Leu Trp Arg Leu Val Ser Leu Leu Ala Leu Ser Gln Ala
1               5                   10                  15

Leu Pro Phe Glu Gln Arg Gly Phe Trp Asp Phe Thr Leu Asp Asp Gly
            20                  25                  30

Pro Phe Met Met Asn Asp Glu Glu Ala Ser Gly Ala Asp Thr Ser Gly
        35                  40                  45

Val Leu Asp Pro Asp Ser Val Thr Pro Thr Tyr Ser Ala Met Cys Pro
50                  55                  60

Phe Gly Cys His Cys His Leu Arg Val Val Gln Cys Ser Asp Leu Gly
65                  70                  75                  80

Leu Lys Ser Val Pro Lys Glu Ile Ser Pro Asp Thr Thr Leu Leu Asp
                85                  90                  95

Leu Gln Asn Asn Asp Ile Ser Glu Leu Arg Lys Asp Asp Phe Lys Gly
            100                 105                 110

Leu Gln His Leu Tyr Ala Leu Val Leu Val Asn Asn Lys Ile Ser Lys
        115                 120                 125

Ile His Glu Lys Ala Phe Ser Pro Leu Arg Lys Leu Gln Lys Leu Tyr
130                 135                 140

Ile Ser Lys Asn His Leu Val Glu Ile Pro Pro Asn Leu Pro Ser Ser
145                 150                 155                 160

Leu Val Glu Leu Arg Ile His Asp Asn Arg Ile Arg Lys Val Pro Lys
                165                 170                 175

Gly Val Phe Ser Gly Leu Arg Asn Met Asn Cys Ile Glu Met Gly Gly
            180                 185                 190

Asn Pro Leu Glu Asn Ser Gly Phe Glu Pro Gly Ala Phe Asp Gly Leu
        195                 200                 205

Lys Leu Asn Tyr Leu Arg Ile Ser Glu Ala Lys Leu Thr Gly Ile Pro
210                 215                 220

Lys Asp Leu Pro Glu Thr Leu Asn Glu Leu His Leu Asp His Asn Lys
225                 230                 235                 240

Ile Gln Ala Ile Glu Leu Glu Asp Leu Leu Arg Tyr Ser Lys Leu Tyr
                245                 250                 255

Arg Leu Gly Leu Gly His Asn Gln Ile Arg Met Ile Glu Asn Gly Ser
            260                 265                 270

Leu Ser Phe Leu Pro Thr Leu Arg Glu Leu His Leu Asp Asn Asn Lys
        275                 280                 285

Leu Ala Arg Val Pro Ser Gly Leu Pro Asp Leu Lys Leu Leu Gln Val
290                 295                 300

Val Tyr Leu His Ser Asn Asn Ile Thr Lys Val Gly Val Asn Asp Phe
305                 310                 315                 320

Cys Pro Met Gly Phe Gly Val Lys Arg Ala Tyr Tyr Asn Gly Ile Ser
                325                 330                 335

Leu Phe Asn Asn Pro Val Pro Tyr Trp Glu Val Gln Pro Ala Thr Phe
            340                 345                 350

Arg Cys Val Thr Asp Arg Leu Ala Ile Gln Phe Gly Asn Tyr Lys Lys
        355                 360                 365
```

<210> SEQ ID NO 10
<211> LENGTH: 368
<212> TYPE: PRT
<213> ORGANISM: Artificial Sequence
<220> FEATURE:
<223> OTHER INFORMATION: mutant of Homo sapiens biglycan

```
<220> FEATURE:
<221> NAME/KEY: MISC_FEATURE
<222> LOCATION: (42)..(42)
<223> OTHER INFORMATION: Xaa can be absent or can be any amino acid
      except Ser or Thr
<220> FEATURE:
<221> NAME/KEY: MISC_FEATURE
<222> LOCATION: (47)..(47)
<223> OTHER INFORMATION: Xaa can be absent or can be any amino acid
      except Ser or Thr

<400> SEQUENCE: 10
```

Met Trp Pro Leu Trp Arg Leu Val Ser Leu Leu Ala Leu Ser Gln Ala
1               5                   10                  15

Leu Pro Phe Glu Gln Arg Gly Phe Trp Asp Phe Thr Leu Asp Asp Gly
            20                  25                  30

Pro Phe Met Met Asn Asp Glu Glu Ala Xaa Gly Ala Asp Thr Xaa Gly
        35                  40                  45

Val Leu Asp Pro Asp Ser Val Thr Pro Thr Tyr Ser Ala Met Cys Pro
    50                  55                  60

Phe Gly Cys His Cys His Leu Arg Val Val Gln Cys Ser Asp Leu Gly
65                  70                  75                  80

Leu Lys Ser Val Pro Lys Glu Ile Ser Pro Asp Thr Thr Leu Leu Asp
                85                  90                  95

Leu Gln Asn Asn Asp Ile Ser Glu Leu Arg Lys Asp Asp Phe Lys Gly
            100                 105                 110

Leu Gln His Leu Tyr Ala Leu Val Leu Val Asn Asn Lys Ile Ser Lys
        115                 120                 125

Ile His Glu Lys Ala Phe Ser Pro Leu Arg Lys Leu Gln Lys Leu Tyr
    130                 135                 140

Ile Ser Lys Asn His Leu Val Glu Ile Pro Pro Asn Leu Pro Ser Ser
145                 150                 155                 160

Leu Val Glu Leu Arg Ile His Asp Asn Arg Ile Arg Lys Val Pro Lys
                165                 170                 175

Gly Val Phe Ser Gly Leu Arg Asn Met Asn Cys Ile Glu Met Gly Gly
            180                 185                 190

Asn Pro Leu Glu Asn Ser Gly Phe Glu Pro Gly Ala Phe Asp Gly Leu
        195                 200                 205

Lys Leu Asn Tyr Leu Arg Ile Ser Glu Ala Lys Leu Thr Gly Ile Pro
    210                 215                 220

Lys Asp Leu Pro Glu Thr Leu Asn Glu Leu His Leu Asp His Asn Lys
225                 230                 235                 240

Ile Gln Ala Ile Glu Leu Glu Asp Leu Leu Arg Tyr Ser Lys Leu Tyr
                245                 250                 255

Arg Leu Gly Leu Gly His Asn Gln Ile Arg Met Ile Glu Asn Gly Ser
            260                 265                 270

Leu Ser Phe Leu Pro Thr Leu Arg Glu Leu His Leu Asp Asn Asn Lys
        275                 280                 285

Leu Ala Arg Val Pro Ser Gly Leu Pro Asp Leu Lys Leu Leu Gln Val
    290                 295                 300

Val Tyr Leu His Ser Asn Asn Ile Thr Lys Val Gly Val Asn Asp Phe
305                 310                 315                 320

Cys Pro Met Gly Phe Gly Val Lys Arg Ala Tyr Tyr Asn Gly Ile Ser
                325                 330                 335

Leu Phe Asn Asn Pro Val Pro Tyr Trp Glu Val Gln Pro Ala Thr Phe
            340                 345                 350

```
Arg Cys Val Thr Asp Arg Leu Ala Ile Gln Phe Gly Asn Tyr Lys Lys
            355                 360                 365
```

<210> SEQ ID NO 11
<211> LENGTH: 368
<212> TYPE: PRT
<213> ORGANISM: Artificial Sequence
<220> FEATURE:
<223> OTHER INFORMATION: mutant of Homo sapiens biglycan

<400> SEQUENCE: 11

```
Met Trp Pro Leu Trp Arg Leu Val Ser Leu Leu Ala Leu Ser Gln Ala
1               5                   10                  15

Leu Pro Phe Glu Gln Arg Gly Phe Trp Asp Phe Thr Leu Asp Asp Gly
            20                  25                  30

Pro Phe Met Met Asn Asp Glu Glu Ala Ala Gly Ala Asp Thr Ala Gly
        35                  40                  45

Val Leu Asp Pro Asp Ser Val Thr Pro Thr Tyr Ser Ala Met Cys Pro
50                  55                  60

Phe Gly Cys His Cys His Leu Arg Val Val Gln Cys Ser Asp Leu Gly
65                  70                  75                  80

Leu Lys Ser Val Pro Lys Glu Ile Ser Pro Asp Thr Thr Leu Leu Asp
                85                  90                  95

Leu Gln Asn Asn Asp Ile Ser Glu Leu Arg Lys Asp Asp Phe Lys Gly
            100                 105                 110

Leu Gln His Leu Tyr Ala Leu Val Leu Val Asn Asn Lys Ile Ser Lys
        115                 120                 125

Ile His Glu Lys Ala Phe Ser Pro Leu Arg Lys Leu Gln Lys Leu Tyr
130                 135                 140

Ile Ser Lys Asn His Leu Val Glu Ile Pro Pro Asn Leu Pro Ser Ser
145                 150                 155                 160

Leu Val Glu Leu Arg Ile His Asp Asn Arg Ile Arg Lys Val Pro Lys
                165                 170                 175

Gly Val Phe Ser Gly Leu Arg Asn Met Asn Cys Ile Glu Met Gly Gly
            180                 185                 190

Asn Pro Leu Glu Asn Ser Gly Phe Glu Pro Gly Ala Phe Asp Gly Leu
        195                 200                 205

Lys Leu Asn Tyr Leu Arg Ile Ser Glu Ala Lys Leu Thr Gly Ile Pro
210                 215                 220

Lys Asp Leu Pro Glu Thr Leu Asn Glu Leu His Leu Asp His Asn Lys
225                 230                 235                 240

Ile Gln Ala Ile Glu Leu Glu Asp Leu Leu Arg Tyr Ser Lys Leu Tyr
                245                 250                 255

Arg Leu Gly Leu Gly His Asn Gln Ile Arg Met Ile Glu Asn Gly Ser
            260                 265                 270

Leu Ser Phe Leu Pro Thr Leu Arg Glu Leu His Leu Asp Asn Asn Lys
        275                 280                 285

Leu Ala Arg Val Pro Ser Gly Leu Pro Asp Leu Lys Leu Leu Gln Val
290                 295                 300

Val Tyr Leu His Ser Asn Asn Ile Thr Lys Val Gly Val Asn Asp Phe
305                 310                 315                 320

Cys Pro Met Gly Phe Gly Val Lys Arg Ala Tyr Tyr Asn Gly Ile Ser
                325                 330                 335

Leu Phe Asn Asn Pro Val Pro Tyr Trp Glu Val Gln Pro Ala Thr Phe
            340                 345                 350
```

Arg Cys Val Thr Asp Arg Leu Ala Ile Gln Phe Gly Asn Tyr Lys Lys
    355                 360                 365

<210> SEQ ID NO 12
<211> LENGTH: 10302
<212> TYPE: DNA
<213> ORGANISM: Homo sapiens

<400> SEQUENCE: 12

| | |
|---|---:|
| atggccaagt atgagaaca tgaagccagt cctgacaatg ggcagaacga attcagtgat | 60 |
| atcattaagt ccagatctga tgaacacaat gacgtacaga agaaaacctt taccaaatgg | 120 |
| ataaatgctc gattttcaaa gagtgggaaa ccacccatca atgatatgtt cacagacctc | 180 |
| aaagatggaa ggaagctatt ggatcttcta gaaggcctca caggaacatc actgccaaag | 240 |
| gaacgtggtt ccacaagggt acatgcctta ataacgtca acagagtgct gcaggtttta | 300 |
| catcagaaca atgtggaatt agtgaatata gggggaactg acattgtgga tggaaatcac | 360 |
| aaactgactt tggggttact ttggagcatc attttgcact ggcaggtgaa agatgtcatg | 420 |
| aaggatgtca tgtcggacct gcagcagacg aacagtgaga gatcctgct cagctgggtg | 480 |
| cgtcagacca ccaggcccta cagccaagtc aacgtcctca acttcaccac cagctggaca | 540 |
| gatggactcg cctttaatgc tgtcctccac cgacataaac ctgatctctt cagctgggat | 600 |
| aaagttgtca aatgtcacc aattgagaga cttgaacatg ccttcagcaa ggctcaaact | 660 |
| tatttgggaa ttgaaaagct gttagatcct gaagatgttg ccgttcggct tcctgacaag | 720 |
| aaatccataa ttatgtattt aacatctttg tttgaggtgc tacctcagca agtcaccata | 780 |
| gacgccatcc gtgaggtaga tactccca aggaaatata aaaagaatg tgaagaagag | 840 |
| gcaattaata tacagagtac agcgcctgag gaggagcatg agagtccccg agctgaaact | 900 |
| cccagcactg tcactgaggt cgacatggat ctggacagct atcagattgc gttggaggaa | 960 |
| gtgctgacct ggttgctttc tgctgaggac actttccagg agcaggatga tatttctgat | 1020 |
| gatgttgaag aagtcaaaga ccagtttgca acccatgaag ctttatgat ggaactgact | 1080 |
| gcacaccaga gcagtgtggg cagcgtcctg caggcaggca accaactgat aacacaagga | 1140 |
| actctgtcag acgaagaaga atttgagatt caggaacaga tgaccctgct gaatgctaga | 1200 |
| tgggaggctc ttagggtgga gagtatggac agacagtccc ggctgcacga tgtgctgatg | 1260 |
| gaactgcaga agaagcaact gcagcagctc tccgcctggt taacactcac agaggagcgc | 1320 |
| attcagaaga tggaaacttg cccctggat gatgatgtaa atctctaca aaagctgcta | 1380 |
| gaagaacata aaagtttgca agtgatctt gaggctgaac aggtgaaagt aaattcacta | 1440 |
| actcacatgg tggtcattgt tgatgaaaac agtggtgaga gcgctacagc tatcctagaa | 1500 |
| gaccagttac agaaacttgg tgagcgctgg acagcgtat gccgttggac tgaagaacgc | 1560 |
| tggaataggt tacaagaaat caatatattg tggcaggaat tattggaaga acagtgcttg | 1620 |
| ttgaaagctt ggttaaccga aaaagaagag gctttaaata agtccagac aagcaacttc | 1680 |
| aaagaccaaa aggaactaag tgtcagtgtt cgacgtctgg ctatttgaa ggaagacatg | 1740 |
| gaaatgaagc gtcaaacatt ggatcagctg agtgagattg ccaggatgt gggacaatta | 1800 |
| cttgataatt ccaaggcatc taagaagatc aacagtgact cagaggaact gactcaaaga | 1860 |
| tgggattctt tggttcagag actagaagat tcctccaacc aggtgactca ggctgtagca | 1920 |
| aagctgggga tgtctcagat tcctcagaag gaccttttgg agactgttcg tgtaagagaa | 1980 |
| caagcaatta caaaaaatc taagcaggaa ctgcctcctc ctcctccccc aagaagaga | 2040 |

```
cagatccatg tggatattga agctaagaaa aagtttgatg ctataagtgc agagctgttg    2100
aactggattt tgaaatggaa aactgccatt cagaccacag agataaaaga gtatatgaag    2160
atgcaagaca cttccgaaat gaaaagaag ttgaaggcat tagaaaaaga acagagagaa     2220
agaatcccca gagcagatga attaaaccaa actggacaaa tccttgtgga gcaaatggga    2280
aaagaaggcc ttcctactga agaaataaaa aatgttctgg agaaggtttc atcagaatgg    2340
aagaatgtat ctcaacattt ggaagatcta gaaagaaaga ttcagctaca ggaagatata    2400
aatgcttatt tcaagcagct tgatgagctt gaaaaggtca tcaagacaaa ggaggagtgg    2460
gtaaaacaca cttccatttc tgaatcttcc cggcagtcct tgccaagctt gaaggattcc    2520
tgtcagcggg aattgacaaa tcttcttggc cttcacccca aaattgaaat ggctcgtgca    2580
agctgctcgg ccctgatgtc tcagccttct gccccagatt ttgtccagcg ggcttcgat    2640 agctttctgg ccgctacca agctgtacaa gaggctgtag aggatcgtca acaacatcta    2700
gagaatgaac tgaagggcca acctggacat gcatatctgg aaacattgaa aacactgaaa    2760
gatgtgctaa atgattcaga aaataaggcc caggtgtctc tgaatgtcct taatgatctt    2820
gccaaggtgg agaaggccct gcaagaaaaa aagaccctg atgaaatcct tgagaatcag    2880
aaacctgcat tacataaact tgcagaagaa acaaaggctc tggagaaaaa tgttcatcct    2940
gatgtagaaa aattatataa gcaagaattt gatgatgtgc aaggaaagtg aacaagcta    3000 aaggtcttgg tttccaaaga tctacatttg cttgaggaaa ttgctctcac actcagagct    3060
tttgaggccg attcaacagt cattgagaag tggatggatg gcgtgaaaga cttcttaatg    3120
aaacagcagg ctgcccaagg agacgacgca ggtctacaga ggcagttaga ccagtgctct    3180
gcatttgtta atgaaataga acaattgaa tcatctctga aaaacatgaa ggaaatagag    3240
actaatcttc gaagtggtcc agttgctgga ataaaaactt gggtgcagac aagactaggt    3300
gactaccaaa ctcaactgga gaaacttagc aaggagatcg ctactcaaaa aagtaggttg    3360
tctgaaagtc aagaaaaagc tgcgaacctg aagaaagact tggcagagat gcaggaatgg    3420
atgacccagg ccgaggaaga atatttggag cgggattttg agtacaagtc accagaagag    3480
cttgagagtc tgtggaaga gatgaagagg gcaaagagg atgtgttgca gaaggaggtg    3540
agagtgaaga ttctcaagga caacatcaag ttattagctg ccaaggtgcc ctctggtggc    3600
caggagttga cgtctgagct gaatgttgtg ctggagaatt accaacttct ttgtaataga    3660
attcgaggaa agtgccacac gctagaggag gtctggtctt gttggattga actgcttcac    3720
tatttggatc ttgaaactac ctggttaaac acttggaag agcggatgaa gagcacagag    3780
gtcctgcctg agaagacgga tgctgtcaac gaagccctgg agtctctgga atctgttctg    3840
cgccacccgg cagataatcg cacccagatt cgagagcttg ccagactct gattgatggg    3900 gggatcctgg atgatataat cagtgagaaa ctggaggctt caacagccg atatgaagat    3960 ctaagtcacc tggcagagag caagcagatt tctttggaaa agcaactcca ggtgctgcgg    4020
gaaactgacc agatgcttca agtcttgcaa gagagcttgg gggagctgga caaacagctc    4080
accacatacc tgactgacag gatagatgct ttccaagttc cacaggaagc tcagaaaatc    4140
caagcagaga tctcagccca tgagctaacc ctagaggagt tgagaagaaa tatgcgttct    4200 cagccctga cctccccaga gagtaggact gccagaggag gaagtcagat ggatgtgcta    4260
cagaggaaac tccgagaggt gtccacaaag ttccagcttt tccagaagcc agctaacttc    4320
gagcagcgca tgctggactg caagcgtgtg ctggatggcg tgaaagcaga acttcacgtt    4380
ctggatgtga aggacgtaga ccctgacgtc atacagacgc acctggacaa gtgtatgaaa    4440
```

```
ctgtataaaa ctttgagtga agtcaaactt gaagtggaaa ctgtgattaa aacaggaaga    4500
catattgtcc agaaacagca aacggacaac ccaaaaggga tggatgagca gctgacttcc    4560
ctgaaggttc tttacaatga cctgggcgca caggtgacag aaggaaaaca ggatctggaa    4620
agagcatcac agttggcccg gaaaatgaag aaagaggctg cttctctctc tgaatggctt    4680
tctgctactg aaactgaatt ggtacagaag tccacttcag aaggtctgct tggtgacttg    4740
gatacagaaa tttcctgggc taaaaatgtt ctgaaggatc tggaaaagag aaaagctgat    4800
ttaaatacca tcacagagag tagtgctgcc ctgcaaaact tgattgaggg cagtgagcct    4860
attttagaag agaggctctg cgtccttaac gctgggtgga gccgagttcg tacctggact    4920
gaagattggt gcaataccct tgatgaaccat cagaaccagc tagaaatatt tgatgggaac    4980
gtggctcaca taagtacctg gctttatcaa gctgaagctc tattggatga aattgaaaag    5040
aaaccaacaa gtaaacagga agaaattgtg aagcgtttag tatctgagct ggatgatgcc    5100
aacctccagg ttgaaaatgt ccgcgatcaa gcccttattt tgatgaatgc ccgtggaagc    5160
tcaagcaggg agcttgtaga accaaagtta gctgagctga ataggaactt tgaaaaggtg    5220
tctcaacata tcaaaagtgc caaattgcta attgctcagg aaccattata ccaatgtttg    5280
gtcaccactg aaacatttga aactggtgtg cctttctctg acttggaaaa attagaaaat    5340
gacatagaaa atatgttaaa atttgtggaa aaacacttgg aatccagtga tgaagatgaa    5400
aagatggatg aggagagtgc ccagattgag gaagttctac aaagaggaga gaaatgttta    5460
catcaaccta tggaagataa taaaaaagaa aagatccgtt tgcaattatt acttttgcat    5520
actagataca acaaaattaa ggcaatccct attcaacaga ggaaaatggg tcaacttgct    5580
tctggaatta gatcatcact tcttcctaca gattatctgg ttgaaattaa caaaatttta    5640 cttttgcatgg atgatgttga attatcgctt aatgttccag agctcaacac tgctatttac    5700
gaagacttct cttttcagga agactctctg aagaatatca aagaccaact ggacaaactt    5760
ggagagcaga ttgcagtcat tcatgaaaaa cagccagatg tcatccttga agcctctgga    5820
cctgaagcca ttcagatcag agatacactt actcagctga atgcaaaatg ggacagaatt    5880
aatagaatgt acagtgatcg gaaaggttgt tttgacaggg caatggaaga atggagacag    5940
ttccattgtg accttaatga cctcacacag tggataacag aggctgaaga attactggtt    6000 gataccgtgtc tccaggtgg cagcctggac ttagagaaag ccaggataca tcagcaggaa    6060
cttgaggtgg gcatcagcag ccaccagccc agttttgcag cactaaaccg aactggggat    6120
gggattgtgc agaaactctc ccaggcagat ggaagcttct tgaaagaaaa actggcaggt    6180
ttaaaccaac gctgggatgc aattgttgca gaagtgaagg ataggcagcc aaggctaaaa    6240
ggagaaagta agcaggtgat gaagtacagg catcagctag atgagattat ctgttggtta    6300
acaaaggctg agcatgctat gcaaaagaga tcaaccaccg aattgggaga aacctgcaa    6360 gaattaagag acttaactca agaaatggaa gtacatgctg aaaaactcaa atggctgaat    6420
agaactgaat tggagatgct ttcagataaa agtctgagtt tacctgaaag ggataaaatt    6480
tcagaaagct taaggactgt aaatatgaca tggaataaga tttgcagaga ggtgcctacc    6540 acctgaagg aatgcatcca ggagcccagt tctgtttcac agacaaggat tgctgctcat    6600
cctaatgtcc aaaaggtggt gctagtatca tctgcgtcag atattcctgt tcagtctcat    6660
cgtacttcgg aaatttcaat tcctgctgat cttgataaaa ctataacaga actagccgac    6720
tggctggtat taatcgacca gatgctgaag tccaacattg tcactgttgg ggatgtagaa    6780
```

```
gagatcaata agaccgtttc ccgaatgaaa attacaaagg ctgacttaga acagcgccat    6840
cctcagctgg attatgtttt tacattggca cagaatttga aaaataaagc ttccagttca    6900
gatatgagaa cagcaattac agaaaaattg gaaagggtca agaaccagtg ggatggcacc    6960
cagcatggcg ttgagctaag acagcagcag cttgaggaca tgattattga cagtcttcag    7020
tgggatgacc ataggagga gactgaagaa ctgatgagaa atatgaggc tcgactctat     7080 attcttcagc aagcccgacg ggatccactc accaaacaaa tttctgataa ccaaatactg    7140
cttcaagaac tgggtcctgg agatggtatc gtcatggcgt tcgataacgt cctgcagaaa    7200
ctcctggagg aatatgggag tgatgacaca aggaatgtga agaaaccac agagtactta     7260 aaaacatcat ggatcaatct caaacaaagt attgctgaca gacagaacgc cttggaggct    7320
gagtggagga cggtgcaggc ctctcgcaga gatctggaaa acttcctgaa gtggatccaa    7380
gaagcagaga ccacagtgaa tgtgcttgtg gatgcctctc atcgggagaa tgctcttcag    7440
gatagtatct tggccaggga actcaaacag cagatgcagg acatccaggc agaaattgat    7500
gcccacaatg acatatttaa aagcattgac ggaaacaggc agaagatggt aaaagctttg    7560
ggaaattctg aagaggctac tatgcttcaa catcgactgg atgatatgaa ccaaagatgg    7620
aatgacttaa aagcaaaatc tgctagcatc agggcccatt tggaggccag cgctgagaag    7680
tggaacaggt tgctgatgtc cttagaagaa ctgatcaaat ggctgaatat gaaagatgaa    7740
gagcttaaga aacaaatgcc tattggagga gatgttccag ccttacagct ccagtatgac    7800
cattgtaagg ccctgagacg ggagttaaag gagaaagaat attctgtcct gaatgctgtc    7860
gaccaggccc gagttttctt ggctgatcag ccaattgagg cccctgaaga gccaagaaga    7920
aacctacaat caaaaacaga attaactcct gaggagagag cccaaaagat tgccaaagcc    7980
atgcgcaaac agtcttctga agtcaaagaa aaatgggaaa gtctaaatgc tgtaactagc    8040
aattggcaaa agcaagtgga caaggcattg gagaaactca gagacctgca gggagctatg    8100
gatgacctgg acgctgacat gaaggaggca gagtccgtgc ggaatggctg gaagcccgtg    8160
ggagacttac tcattgactc gctgcaggat cacattgaaa aaatcatggc atttagagaa    8220
gaaattgcac caatcaactt taaagttaaa acggtgaatg atttatccag tcagctgtct    8280
ccacttgacc tgcatccctc tctaaagatg tctcgccagc tagatgacct taatatgcga    8340
tggaaacttt tacaggtttc tgtggatgat cgccttaaac agcttcagga agcccacaga    8400
gattttggac catcctctca gcattttctc tctacgtcag tccagctgcc gtggcaaaga    8460
tccatttcac ataataaagt gccctattac atcaaccatc aaacacagac cacctgttgg    8520
gaccatccta aaatgaccga actctttcaa tcccttgctg acctgaataa tgtacgtttt    8580
tctgcctacc gtacagcaat caaaatccga agactacaaa aagcactatg tttggatctc    8640
ttagagttga gtacaacaaa tgaaattttc aaacagcaca agttgaacca aaatgaccag    8700
ctcctcagtg ttccagatgt catcaactgt ctgacaacaa cttatgatgg acttgagcaa    8760
atgcataagg acctggtcaa cgttccactc tgtgttgata tgtgtctcaa ttggttgctc    8820
aatgtctatg acacgggtcg aactggaaaa attagagtgc agagtctgaa gattggatta    8880
atgtctctct ccaaaggtct cttggaagaa aaatacagat atctctttaa ggaagttgcg    8940
gggccgacag aaatgtgtga ccagaggcag ctgggcctgt tacttcatga tgccatccag    9000
atcccccggc agctaggtga agtagcagct tttggaggca gtaatattga gcctagtgtt    9060
cgcagctgct tccaacagaa taacaataaa ccagaaataa gtgtgaaaga gtttatagat    9120
tggatgcatt tggaaccaca gtccatggtt tggctcccag ttttacatcg agtggcagca    9180
```

```
gcggagactg caaaacatca ggccaaatgc aacatctgta aagaatgtcc aattgtcggg    9240
ttcaggtata gaagccttaa gcattttaac tatgatgtct gccagagttg tttcttttcg    9300
ggtcgaacag caaaaggtca caaattacat tacccaatgg tggaatattg tatacctaca    9360
acatctgggg aagatgtacg agacttcaca aaggtactta agaacaagtt caggtcgaag    9420
aagtactttg ccaaacaccc tcgacttggt tacctgcctg tccagacagt tcttgaaggt    9480
gacaacttag agactcctat cacactcatc agtatgtggc cagagcacta tgaccoctca    9540 caatctcctc aactgtttca tgatgacacc cattcaagaa tagaacaata tgccacacga    9600
ctggcccaga tggaaaggac taatgggtct tttctcactg atagcagctc caccacagga    9660
agtgtggaag acgagcacgc cctcatccag cagtattgcc aaacactcgg aggagagtcc    9720
ccagtgagcc agccgcagag cccagctcag atcctgaagt cagtagagag gaagaacgt     9780 ggagaactgg agaggatcat tgctgacctg gaggaagaac aaagaaatct acaggtggag    9840
tatgagcagc tgaaggacca gcacctccga agggggctcc ctgtcggttc accgccagag    9900
tcgattatat ctccccatca cacgtctgag gattcagaac ttatagcaga agcaaaactc    9960
ctcaggcagc acaaaggtcg gctggaggct aggatgcaga ttttagaaga tcacaataaa   10020
cagctggagt ctcagctcca ccgcctccga cagctgctgg agcagcctga atctgattcc   10080
cgaatcaatg tgtttcccc atgggcttct cctcagcatt ctgcactgag ctactcgctt    10140
gatccagatg cctccggccc acagttccac caggcagcgg gagaggacct gctggcccca   10200
ccgcacgaca ccagcacgga tctcacggag gtcatggagc agattcacag cacgtttcca   10260
tcttgctgcc caaatgttcc cagcaggcca caggcaatgt ga                      10302

<210> SEQ ID NO 13
<211> LENGTH: 3433
<212> TYPE: PRT
<213> ORGANISM: Homo sapiens

<400> SEQUENCE: 13

Met Ala Lys Tyr Gly Glu His Glu Ala Ser Pro Asp Asn Gly Gln Asn
1               5                   10                  15

Glu Phe Ser Asp Ile Ile Lys Ser Arg Ser Asp Glu His Asn Asp Val
                20                  25                  30

Gln Lys Lys Thr Phe Thr Lys Trp Ile Asn Ala Arg Phe Ser Lys Ser
            35                  40                  45

Gly Lys Pro Pro Ile Asn Asp Met Phe Thr Asp Leu Lys Asp Gly Arg
        50                  55                  60

Lys Leu Leu Asp Leu Leu Glu Gly Leu Thr Gly Thr Ser Leu Pro Lys
65                  70                  75                  80

Glu Arg Gly Ser Thr Arg Val His Ala Leu Asn Val Asn Arg Val
                85                  90                  95

Leu Gln Val Leu His Gln Asn Asn Val Glu Leu Val Asn Ile Gly Gly
            100                 105                 110

Thr Asp Ile Val Asp Gly Asn His Lys Leu Thr Leu Gly Leu Leu Trp
        115                 120                 125

Ser Ile Ile Leu His Trp Gln Val Lys Asp Val Met Lys Asp Val Met
        130                 135                 140

Ser Asp Leu Gln Gln Thr Asn Ser Glu Lys Ile Leu Leu Ser Trp Val
145                 150                 155                 160

Arg Gln Thr Thr Arg Pro Tyr Ser Gln Val Asn Val Leu Asn Phe Thr
                165                 170                 175
```

-continued

```
Thr Ser Trp Thr Asp Gly Leu Ala Phe Asn Ala Val Leu His Arg His
            180                 185                 190

Lys Pro Asp Leu Phe Ser Trp Asp Lys Val Val Lys Met Ser Pro Ile
        195                 200                 205

Glu Arg Leu Glu His Ala Phe Ser Lys Ala Gln Thr Tyr Leu Gly Ile
    210                 215                 220

Glu Lys Leu Leu Asp Pro Glu Asp Val Ala Val Arg Leu Pro Asp Lys
225                 230                 235                 240

Lys Ser Ile Ile Met Tyr Leu Thr Ser Leu Phe Glu Val Leu Pro Gln
                245                 250                 255

Gln Val Thr Ile Asp Ala Ile Arg Glu Val Thr Leu Pro Arg Lys
    260                 265                 270

Tyr Lys Lys Glu Cys Glu Glu Ala Ile Asn Ile Gln Ser Thr Ala
        275                 280                 285

Pro Glu Glu Glu His Glu Ser Pro Arg Ala Glu Thr Pro Ser Thr Val
    290                 295                 300

Thr Glu Val Asp Met Asp Leu Asp Ser Tyr Gln Ile Ala Leu Glu Glu
305                 310                 315                 320

Val Leu Thr Trp Leu Leu Ser Ala Glu Asp Thr Phe Gln Glu Gln Asp
                325                 330                 335

Asp Ile Ser Asp Asp Val Glu Glu Val Lys Asp Gln Phe Ala Thr His
                340                 345                 350

Glu Ala Phe Met Met Glu Leu Thr Ala His Gln Ser Ser Val Gly Ser
            355                 360                 365

Val Leu Gln Ala Gly Asn Gln Leu Ile Thr Gln Gly Thr Leu Ser Asp
    370                 375                 380

Glu Glu Glu Phe Glu Ile Gln Glu Gln Met Thr Leu Leu Asn Ala Arg
385                 390                 395                 400

Trp Glu Ala Leu Arg Val Glu Ser Met Asp Arg Gln Ser Arg Leu His
                405                 410                 415

Asp Val Leu Met Glu Leu Gln Lys Lys Gln Leu Gln Leu Ser Ala
                420                 425                 430

Trp Leu Thr Leu Thr Glu Glu Arg Ile Gln Lys Met Glu Thr Cys Pro
    435                 440                 445

Leu Asp Asp Asp Val Lys Ser Leu Gln Lys Leu Leu Glu Glu His Lys
450                 455                 460

Ser Leu Gln Ser Asp Leu Glu Ala Glu Gln Val Lys Val Asn Ser Leu
465                 470                 475                 480

Thr His Met Val Val Ile Val Asp Glu Asn Ser Gly Glu Ser Ala Thr
                485                 490                 495

Ala Ile Leu Glu Asp Gln Leu Gln Lys Leu Gly Glu Arg Trp Thr Ala
            500                 505                 510

Val Cys Arg Trp Thr Glu Glu Arg Trp Asn Arg Leu Gln Glu Ile Asn
        515                 520                 525

Ile Leu Trp Gln Glu Leu Leu Glu Glu Gln Cys Leu Leu Lys Ala Trp
    530                 535                 540

Leu Thr Glu Lys Glu Glu Ala Leu Asn Lys Val Gln Thr Ser Asn Phe
545                 550                 555                 560

Lys Asp Gln Lys Glu Leu Ser Val Ser Val Arg Arg Leu Ala Ile Leu
                565                 570                 575

Lys Glu Asp Met Glu Met Lys Arg Gln Thr Leu Asp Gln Leu Ser Glu
            580                 585                 590
```

-continued

```
Ile Gly Gln Asp Val Gly Gln Leu Asp Asn Ser Lys Ala Ser Lys
            595                 600                 605
Lys Ile Asn Ser Asp Ser Glu Glu Leu Thr Gln Arg Trp Asp Ser Leu
610                 615                 620
Val Gln Arg Leu Glu Asp Ser Ser Asn Gln Val Thr Gln Ala Val Ala
625                 630                 635                 640
Lys Leu Gly Met Ser Gln Ile Pro Gln Lys Asp Leu Leu Glu Thr Val
                645                 650                 655
Arg Val Arg Glu Gln Ala Ile Thr Lys Ser Lys Gln Glu Leu Pro
            660                 665                 670
Pro Pro Pro Pro Lys Lys Arg Gln Ile His Val Asp Ile Glu Ala
            675                 680                 685
Lys Lys Lys Phe Asp Ala Ile Ser Ala Glu Leu Leu Asn Trp Ile Leu
690                 695                 700
Lys Trp Lys Thr Ala Ile Gln Thr Thr Glu Ile Lys Glu Tyr Met Lys
705                 710                 715                 720
Met Gln Asp Thr Ser Glu Met Lys Lys Lys Leu Lys Ala Leu Glu Lys
                725                 730                 735
Glu Gln Arg Glu Arg Ile Pro Arg Ala Asp Glu Leu Asn Gln Thr Gly
            740                 745                 750
Gln Ile Leu Val Glu Gln Met Gly Lys Glu Gly Leu Pro Thr Glu Glu
            755                 760                 765
Ile Lys Asn Val Leu Glu Lys Val Ser Ser Glu Trp Lys Asn Val Ser
            770                 775                 780
Gln His Leu Glu Asp Leu Glu Arg Lys Ile Gln Leu Gln Glu Asp Ile
785                 790                 795                 800
Asn Ala Tyr Phe Lys Gln Leu Asp Glu Leu Glu Lys Val Ile Lys Thr
                805                 810                 815
Lys Glu Glu Trp Val Lys His Thr Ser Ile Ser Glu Ser Ser Arg Gln
            820                 825                 830
Ser Leu Pro Ser Leu Lys Asp Ser Cys Gln Arg Glu Leu Thr Asn Leu
            835                 840                 845
Leu Gly Leu His Pro Lys Ile Glu Met Ala Arg Ala Ser Cys Ser Ala
850                 855                 860
Leu Met Ser Gln Pro Ser Ala Pro Asp Phe Val Gln Arg Gly Phe Asp
865                 870                 875                 880
Ser Phe Leu Gly Arg Tyr Gln Ala Val Gln Glu Ala Val Glu Asp Arg
                885                 890                 895
Gln Gln His Leu Glu Asn Glu Leu Lys Gly Gln Pro Gly His Ala Tyr
            900                 905                 910
Leu Glu Thr Leu Lys Thr Leu Lys Asp Val Leu Asn Asp Ser Glu Asn
            915                 920                 925
Lys Ala Gln Val Ser Leu Asn Val Leu Asn Asp Leu Ala Lys Val Glu
930                 935                 940
Lys Ala Leu Gln Glu Lys Lys Thr Leu Asp Glu Ile Leu Glu Asn Gln
945                 950                 955                 960
Lys Pro Ala Leu His Lys Leu Ala Glu Glu Thr Lys Ala Leu Glu Lys
                965                 970                 975
Asn Val His Pro Asp Val Glu Lys Leu Tyr Lys Gln Glu Phe Asp Asp
            980                 985                 990
Val Gln Gly Lys Trp Asn Lys Leu  Lys Val Leu Val Ser  Lys Asp Leu
            995                1000                1005
His Leu  Leu Glu Glu Ile Ala  Leu Thr Leu Arg Ala  Phe Glu Ala
```

-continued

```
                1010                1015                1020

Asp Ser Thr Val Ile Glu Lys Trp Met Asp Gly Val Lys Asp Phe
    1025                1030                1035

Leu Met Lys Gln Gln Ala Ala Gln Gly Asp Asp Ala Gly Leu Gln
    1040                1045                1050

Arg Gln Leu Asp Gln Cys Ser Ala Phe Val Asn Glu Ile Glu Thr
    1055                1060                1065

Ile Glu Ser Ser Leu Lys Asn Met Lys Glu Ile Glu Thr Asn Leu
    1070                1075                1080

Arg Ser Gly Pro Val Ala Gly Ile Lys Thr Trp Val Gln Thr Arg
    1085                1090                1095

Leu Gly Asp Tyr Gln Thr Gln Leu Glu Lys Leu Ser Lys Glu Ile
    1100                1105                1110

Ala Thr Gln Lys Ser Arg Leu Ser Glu Ser Gln Glu Lys Ala Ala
    1115                1120                1125

Asn Leu Lys Lys Asp Leu Ala Glu Met Gln Glu Trp Met Thr Gln
    1130                1135                1140

Ala Glu Glu Glu Tyr Leu Glu Arg Asp Phe Glu Tyr Lys Ser Pro
    1145                1150                1155

Glu Glu Leu Glu Ser Ala Val Glu Glu Met Lys Arg Ala Lys Glu
    1160                1165                1170

Asp Val Leu Gln Lys Glu Val Arg Val Lys Ile Leu Lys Asp Asn
    1175                1180                1185

Ile Lys Leu Leu Ala Ala Lys Val Pro Ser Gly Gly Gln Glu Leu
    1190                1195                1200

Thr Ser Glu Leu Asn Val Val Leu Glu Asn Tyr Gln Leu Leu Cys
    1205                1210                1215

Asn Arg Ile Arg Gly Lys Cys His Thr Leu Glu Glu Val Trp Ser
    1220                1225                1230

Cys Trp Ile Glu Leu Leu His Tyr Leu Asp Leu Glu Thr Thr Trp
    1235                1240                1245

Leu Asn Thr Leu Glu Glu Arg Met Lys Ser Thr Glu Val Leu Pro
    1250                1255                1260

Glu Lys Thr Asp Ala Val Asn Glu Ala Leu Glu Ser Leu Glu Ser
    1265                1270                1275

Val Leu Arg His Pro Ala Asp Asn Arg Thr Gln Ile Arg Glu Leu
    1280                1285                1290

Gly Gln Thr Leu Ile Asp Gly Gly Ile Leu Asp Asp Ile Ile Ser
    1295                1300                1305

Glu Lys Leu Glu Ala Phe Asn Ser Arg Tyr Glu Asp Leu Ser His
    1310                1315                1320

Leu Ala Glu Ser Lys Gln Ile Ser Leu Glu Lys Gln Leu Gln Val
    1325                1330                1335

Leu Arg Glu Thr Asp Gln Met Leu Gln Val Leu Gln Glu Ser Leu
    1340                1345                1350

Gly Glu Leu Asp Lys Gln Leu Thr Thr Tyr Leu Thr Asp Arg Ile
    1355                1360                1365

Asp Ala Phe Gln Val Pro Gln Glu Ala Gln Lys Ile Gln Ala Glu
    1370                1375                1380

Ile Ser Ala His Glu Leu Thr Leu Glu Glu Leu Arg Arg Asn Met
    1385                1390                1395

Arg Ser Gln Pro Leu Thr Ser Pro Glu Ser Arg Thr Ala Arg Gly
    1400                1405                1410
```

-continued

```
Gly Ser Gln Met Asp Val Leu Gln Arg Lys Leu Arg Glu Val Ser
1415                1420                1425

Thr Lys Phe Gln Leu Phe Gln Lys Pro Ala Asn Phe Glu Gln Arg
1430                1435                1440

Met Leu Asp Cys Lys Arg Val Leu Asp Gly Val Lys Ala Glu Leu
1445                1450                1455

His Val Leu Asp Val Lys Asp Val Asp Pro Asp Val Ile Gln Thr
1460                1465                1470

His Leu Asp Lys Cys Met Lys Leu Tyr Lys Thr Leu Ser Glu Val
1475                1480                1485

Lys Leu Glu Val Glu Thr Val Ile Lys Thr Gly Arg His Ile Val
1490                1495                1500

Gln Lys Gln Gln Thr Asp Asn Pro Lys Gly Met Asp Glu Gln Leu
1505                1510                1515

Thr Ser Leu Lys Val Leu Tyr Asn Asp Leu Gly Ala Gln Val Thr
1520                1525                1530

Glu Gly Lys Gln Asp Leu Glu Arg Ala Ser Gln Leu Ala Arg Lys
1535                1540                1545

Met Lys Lys Glu Ala Ala Ser Leu Ser Glu Trp Leu Ser Ala Thr
1550                1555                1560

Glu Thr Glu Leu Val Gln Lys Ser Thr Ser Glu Gly Leu Leu Gly
1565                1570                1575

Asp Leu Asp Thr Glu Ile Ser Trp Ala Lys Asn Val Leu Lys Asp
1580                1585                1590

Leu Glu Lys Arg Lys Ala Asp Leu Asn Thr Ile Thr Glu Ser Ser
1595                1600                1605

Ala Ala Leu Gln Asn Leu Ile Glu Gly Ser Glu Pro Ile Leu Glu
1610                1615                1620

Glu Arg Leu Cys Val Leu Asn Ala Gly Trp Ser Arg Val Arg Thr
1625                1630                1635

Trp Thr Glu Asp Trp Cys Asn Thr Leu Met Asn His Gln Asn Gln
1640                1645                1650

Leu Glu Ile Phe Asp Gly Asn Val Ala His Ile Ser Thr Trp Leu
1655                1660                1665

Tyr Gln Ala Glu Ala Leu Leu Asp Glu Ile Glu Lys Lys Pro Thr
1670                1675                1680

Ser Lys Gln Glu Glu Ile Val Lys Arg Leu Val Ser Glu Leu Asp
1685                1690                1695

Asp Ala Asn Leu Gln Val Glu Asn Val Arg Asp Gln Ala Leu Ile
1700                1705                1710

Leu Met Asn Ala Arg Gly Ser Ser Ser Arg Glu Leu Val Glu Pro
1715                1720                1725

Lys Leu Ala Glu Leu Asn Arg Asn Phe Glu Lys Val Ser Gln His
1730                1735                1740

Ile Lys Ser Ala Lys Leu Leu Ile Ala Gln Glu Pro Leu Tyr Gln
1745                1750                1755

Cys Leu Val Thr Thr Glu Thr Phe Glu Thr Gly Val Pro Phe Ser
1760                1765                1770

Asp Leu Glu Lys Leu Glu Asn Asp Ile Glu Asn Met Leu Lys Phe
1775                1780                1785

Val Glu Lys His Leu Glu Ser Ser Asp Glu Asp Glu Lys Met Asp
1790                1795                1800
```

-continued

```
Glu Glu Ser Ala Gln Ile Glu Val Leu Gln Arg Gly Glu Glu
    1805                1810                1815

Met Leu His Gln Pro Met Glu Asp Asn Lys Lys Glu Lys Ile Arg
    1820                1825                1830

Leu Gln Leu Leu Leu Leu His Thr Arg Tyr Asn Lys Ile Lys Ala
    1835                1840                1845

Ile Pro Ile Gln Gln Arg Lys Met Gly Gln Leu Ala Ser Gly Ile
    1850                1855                1860

Arg Ser Ser Leu Leu Pro Thr Asp Tyr Leu Val Glu Ile Asn Lys
    1865                1870                1875

Ile Leu Leu Cys Met Asp Asp Val Glu Leu Ser Leu Asn Val Pro
    1880                1885                1890

Glu Leu Asn Thr Ala Ile Tyr Glu Asp Phe Ser Phe Gln Glu Asp
    1895                1900                1905

Ser Leu Lys Asn Ile Lys Asp Gln Leu Asp Lys Leu Gly Glu Gln
    1910                1915                1920

Ile Ala Val Ile His Glu Lys Gln Pro Asp Val Ile Leu Glu Ala
    1925                1930                1935

Ser Gly Pro Glu Ala Ile Gln Ile Arg Asp Thr Leu Thr Gln Leu
    1940                1945                1950

Asn Ala Lys Trp Asp Arg Ile Asn Arg Met Tyr Ser Asp Arg Lys
    1955                1960                1965

Gly Cys Phe Asp Arg Ala Met Glu Glu Trp Arg Gln Phe His Cys
    1970                1975                1980

Asp Leu Asn Asp Leu Thr Gln Trp Ile Thr Glu Ala Glu Glu Leu
    1985                1990                1995

Leu Val Asp Thr Cys Ala Pro Gly Gly Ser Leu Asp Leu Glu Lys
    2000                2005                2010

Ala Arg Ile His Gln Gln Glu Leu Glu Val Gly Ile Ser Ser His
    2015                2020                2025

Gln Pro Ser Phe Ala Ala Leu Asn Arg Thr Gly Asp Gly Ile Val
    2030                2035                2040

Gln Lys Leu Ser Gln Ala Asp Gly Ser Phe Leu Lys Glu Lys Leu
    2045                2050                2055

Ala Gly Leu Asn Gln Arg Trp Asp Ala Ile Val Ala Glu Val Lys
    2060                2065                2070

Asp Arg Gln Pro Arg Leu Lys Gly Glu Ser Lys Gln Val Met Lys
    2075                2080                2085

Tyr Arg His Gln Leu Asp Glu Ile Ile Cys Trp Leu Thr Lys Ala
    2090                2095                2100

Glu His Ala Met Gln Lys Arg Ser Thr Thr Glu Leu Gly Glu Asn
    2105                2110                2115

Leu Gln Glu Leu Arg Asp Leu Thr Gln Glu Met Glu Val His Ala
    2120                2125                2130

Glu Lys Leu Lys Trp Leu Asn Arg Thr Glu Leu Glu Met Leu Ser
    2135                2140                2145

Asp Lys Ser Leu Ser Leu Pro Glu Arg Asp Lys Ile Ser Glu Ser
    2150                2155                2160

Leu Arg Thr Val Asn Met Thr Trp Asn Lys Ile Cys Arg Glu Val
    2165                2170                2175

Pro Thr Thr Leu Lys Glu Cys Ile Gln Glu Pro Ser Ser Val Ser
    2180                2185                2190

Gln Thr Arg Ile Ala Ala His Pro Asn Val Gln Lys Val Val Leu
```

```
              2195                2200                2205
Val  Ser  Ser  Ala  Ser  Asp  Ile  Pro  Val  Gln  Ser  His  Arg  Thr  Ser
     2210                2215                2220

Glu  Ile  Ser  Ile  Pro  Ala  Asp  Leu  Asp  Lys  Thr  Ile  Thr  Glu  Leu
     2225                2230                2235

Ala  Asp  Trp  Leu  Val  Leu  Ile  Asp  Gln  Met  Leu  Lys  Ser  Asn  Ile
     2240                2245                2250

Val  Thr  Val  Gly  Asp  Val  Glu  Glu  Ile  Asn  Lys  Thr  Val  Ser  Arg
     2255                2260                2265

Met  Lys  Ile  Thr  Lys  Ala  Asp  Leu  Glu  Gln  Arg  His  Pro  Gln  Leu
     2270                2275                2280

Asp  Tyr  Val  Phe  Thr  Leu  Ala  Gln  Asn  Leu  Lys  Asn  Lys  Ala  Ser
     2285                2290                2295

Ser  Ser  Asp  Met  Arg  Thr  Ala  Ile  Thr  Glu  Lys  Leu  Glu  Arg  Val
     2300                2305                2310

Lys  Asn  Gln  Trp  Asp  Gly  Thr  Gln  His  Gly  Val  Glu  Leu  Arg  Gln
     2315                2320                2325

Gln  Gln  Leu  Glu  Asp  Met  Ile  Ile  Asp  Ser  Leu  Gln  Trp  Asp  Asp
     2330                2335                2340

His  Arg  Glu  Glu  Thr  Glu  Glu  Leu  Met  Arg  Lys  Tyr  Glu  Ala  Arg
     2345                2350                2355

Leu  Tyr  Ile  Leu  Gln  Gln  Ala  Arg  Arg  Asp  Pro  Leu  Thr  Lys  Gln
     2360                2365                2370

Ile  Ser  Asp  Asn  Gln  Ile  Leu  Leu  Gln  Glu  Leu  Gly  Pro  Gly  Asp
     2375                2380                2385

Gly  Ile  Val  Met  Ala  Phe  Asp  Asn  Val  Leu  Gln  Lys  Leu  Leu  Glu
     2390                2395                2400

Glu  Tyr  Gly  Ser  Asp  Asp  Thr  Arg  Asn  Val  Lys  Glu  Thr  Thr  Glu
     2405                2410                2415

Tyr  Leu  Lys  Thr  Ser  Trp  Ile  Asn  Leu  Lys  Gln  Ser  Ile  Ala  Asp
     2420                2425                2430

Arg  Gln  Asn  Ala  Leu  Glu  Ala  Glu  Trp  Arg  Thr  Val  Gln  Ala  Ser
     2435                2440                2445

Arg  Arg  Asp  Leu  Glu  Asn  Phe  Leu  Lys  Trp  Ile  Gln  Glu  Ala  Glu
     2450                2455                2460

Thr  Thr  Val  Asn  Val  Leu  Val  Asp  Ala  Ser  His  Arg  Glu  Asn  Ala
     2465                2470                2475

Leu  Gln  Asp  Ser  Ile  Leu  Ala  Arg  Glu  Leu  Lys  Gln  Gln  Met  Gln
     2480                2485                2490

Asp  Ile  Gln  Ala  Glu  Ile  Asp  Ala  His  Asn  Asp  Ile  Phe  Lys  Ser
     2495                2500                2505

Ile  Asp  Gly  Asn  Arg  Gln  Lys  Met  Val  Lys  Ala  Leu  Gly  Asn  Ser
     2510                2515                2520

Glu  Glu  Ala  Thr  Met  Leu  Gln  His  Arg  Leu  Asp  Asp  Met  Asn  Gln
     2525                2530                2535

Arg  Trp  Asn  Asp  Leu  Lys  Ala  Lys  Ser  Ala  Ser  Ile  Arg  Ala  His
     2540                2545                2550

Leu  Glu  Ala  Ser  Ala  Glu  Lys  Trp  Asn  Arg  Leu  Leu  Met  Ser  Leu
     2555                2560                2565

Glu  Glu  Leu  Ile  Lys  Trp  Leu  Asn  Met  Lys  Asp  Glu  Glu  Leu  Lys
     2570                2575                2580

Lys  Gln  Met  Pro  Ile  Gly  Gly  Asp  Val  Pro  Ala  Leu  Gln  Leu  Gln
     2585                2590                2595
```

-continued

```
Tyr Asp His Cys Lys Ala Leu Arg Arg Glu Leu Lys Glu Lys Glu
2600                2605                2610

Tyr Ser Val Leu Asn Ala Val Asp Gln Ala Arg Val Phe Leu Ala
2615                2620                2625

Asp Gln Pro Ile Glu Ala Pro Glu Glu Pro Arg Arg Asn Leu Gln
2630                2635                2640

Ser Lys Thr Glu Leu Thr Pro Glu Glu Arg Ala Gln Lys Ile Ala
2645                2650                2655

Lys Ala Met Arg Lys Gln Ser Ser Glu Val Lys Glu Lys Trp Glu
2660                2665                2670

Ser Leu Asn Ala Val Thr Ser Asn Trp Gln Lys Gln Val Asp Lys
2675                2680                2685

Ala Leu Glu Lys Leu Arg Asp Leu Gln Gly Ala Met Asp Asp Leu
2690                2695                2700

Asp Ala Asp Met Lys Glu Ala Glu Ser Val Arg Asn Gly Trp Lys
2705                2710                2715

Pro Val Gly Asp Leu Leu Ile Asp Ser Leu Gln Asp His Ile Glu
2720                2725                2730

Lys Ile Met Ala Phe Arg Glu Glu Ile Ala Pro Ile Asn Phe Lys
2735                2740                2745

Val Lys Thr Val Asn Asp Leu Ser Ser Gln Leu Ser Pro Leu Asp
2750                2755                2760

Leu His Pro Ser Leu Lys Met Ser Arg Gln Leu Asp Asp Leu Asn
2765                2770                2775

Met Arg Trp Lys Leu Leu Gln Val Ser Val Asp Asp Arg Leu Lys
2780                2785                2790

Gln Leu Gln Glu Ala His Arg Asp Phe Gly Pro Ser Ser Gln His
2795                2800                2805

Phe Leu Ser Thr Ser Val Gln Leu Pro Trp Gln Arg Ser Ile Ser
2810                2815                2820

His Asn Lys Val Pro Tyr Tyr Ile Asn His Gln Thr Gln Thr Thr
2825                2830                2835

Cys Trp Asp His Pro Lys Met Thr Glu Leu Phe Gln Ser Leu Ala
2840                2845                2850

Asp Leu Asn Asn Val Arg Phe Ser Ala Tyr Arg Thr Ala Ile Lys
2855                2860                2865

Ile Arg Arg Leu Gln Lys Ala Leu Cys Leu Asp Leu Leu Glu Leu
2870                2875                2880

Ser Thr Thr Asn Glu Ile Phe Lys Gln His Lys Leu Asn Gln Asn
2885                2890                2895

Asp Gln Leu Leu Ser Val Pro Asp Val Ile Asn Cys Leu Thr Thr
2900                2905                2910

Thr Tyr Asp Gly Leu Glu Gln Met His Lys Asp Leu Val Asn Val
2915                2920                2925

Pro Leu Cys Val Asp Met Cys Leu Asn Trp Leu Leu Asn Val Tyr
2930                2935                2940

Asp Thr Gly Arg Thr Gly Lys Ile Arg Val Gln Ser Leu Lys Ile
2945                2950                2955

Gly Leu Met Ser Leu Ser Lys Gly Leu Leu Glu Glu Lys Tyr Arg
2960                2965                2970

Tyr Leu Phe Lys Glu Val Ala Gly Pro Thr Glu Met Cys Asp Gln
2975                2980                2985
```

```
Arg Gln Leu Gly Leu Leu Leu His Asp Ala Ile Gln Ile Pro Arg
    2990                2995                3000

Gln Leu Gly Glu Val Ala Ala Phe Gly Gly Ser Asn Ile Glu Pro
    3005                3010                3015

Ser Val Arg Ser Cys Phe Gln Asn Asn Asn Lys Pro Glu Ile
    3020                3025                3030

Ser Val Lys Glu Phe Ile Asp Trp Met His Leu Glu Pro Gln Ser
    3035                3040                3045

Met Val Trp Leu Pro Val Leu His Arg Val Ala Ala Ala Glu Thr
    3050                3055                3060

Ala Lys His Gln Ala Lys Cys Asn Ile Cys Lys Glu Cys Pro Ile
    3065                3070                3075

Val Gly Phe Arg Tyr Arg Ser Leu Lys His Phe Asn Tyr Asp Val
    3080                3085                3090

Cys Gln Ser Cys Phe Phe Ser Gly Arg Thr Ala Lys Gly His Lys
    3095                3100                3105

Leu His Tyr Pro Met Val Glu Tyr Cys Ile Pro Thr Thr Ser Gly
    3110                3115                3120

Glu Asp Val Arg Asp Phe Thr Lys Val Leu Lys Asn Lys Phe Arg
    3125                3130                3135

Ser Lys Lys Tyr Phe Ala Lys His Pro Arg Leu Gly Tyr Leu Pro
    3140                3145                3150

Val Gln Thr Val Leu Glu Gly Asp Asn Leu Glu Thr Pro Ile Thr
    3155                3160                3165

Leu Ile Ser Met Trp Pro Glu His Tyr Asp Pro Ser Gln Ser Pro
    3170                3175                3180

Gln Leu Phe His Asp Asp Thr His Ser Arg Ile Glu Gln Tyr Ala
    3185                3190                3195

Thr Arg Leu Ala Gln Met Glu Arg Thr Asn Gly Ser Phe Leu Thr
    3200                3205                3210

Asp Ser Ser Ser Thr Thr Gly Ser Val Glu Asp Glu His Ala Leu
    3215                3220                3225

Ile Gln Gln Tyr Cys Gln Thr Leu Gly Gly Glu Ser Pro Val Ser
    3230                3235                3240

Gln Pro Gln Ser Pro Ala Gln Ile Leu Lys Ser Val Glu Arg Glu
    3245                3250                3255

Glu Arg Gly Glu Leu Glu Arg Ile Ile Ala Asp Leu Glu Glu Glu
    3260                3265                3270

Gln Arg Asn Leu Gln Val Glu Tyr Glu Gln Leu Lys Asp Gln His
    3275                3280                3285

Leu Arg Arg Gly Leu Pro Val Gly Ser Pro Pro Glu Ser Ile Ile
    3290                3295                3300

Ser Pro His His Thr Ser Glu Asp Ser Glu Leu Ile Ala Glu Ala
    3305                3310                3315

Lys Leu Leu Arg Gln His Lys Gly Arg Leu Glu Ala Arg Met Gln
    3320                3325                3330

Ile Leu Glu Asp His Asn Lys Gln Leu Glu Ser Gln Leu His Arg
    3335                3340                3345

Leu Arg Gln Leu Leu Glu Gln Pro Glu Ser Asp Ser Arg Ile Asn
    3350                3355                3360

Gly Val Ser Pro Trp Ala Ser Pro Gln His Ser Ala Leu Ser Tyr
    3365                3370                3375

Ser Leu Asp Pro Asp Ala Ser Gly Pro Gln Phe His Gln Ala Ala
```

```
                   3380                3385                3390

Gly Glu  Asp Leu Leu Ala Pro  Pro His Asp Thr Ser  Thr Asp Leu
        3395                3400                3405

Thr Glu  Val Met Glu Gln Ile  His Ser Thr Phe Pro  Ser Cys Cys
        3410                3415                3420

Pro Asn  Val Pro Ser Arg Pro  Gln Ala Met
        3425                3430

<210> SEQ ID NO 14
<211> LENGTH: 20
<212> TYPE: DNA
<213> ORGANISM: Mus musculus

<400> SEQUENCE: 14
tgggaaaatc ggactctttg                                         20

<210> SEQ ID NO 15
<211> LENGTH: 20
<212> TYPE: DNA
<213> ORGANISM: Mus musculus

<400> SEQUENCE: 15
agtaaccacc atgggctttg                                         20

<210> SEQ ID NO 16
<211> LENGTH: 20
<212> TYPE: DNA
<213> ORGANISM: Mus musculus

<400> SEQUENCE: 16
tcccaagacc cattcaaccc                                         20

<210> SEQ ID NO 17
<211> LENGTH: 22
<212> TYPE: DNA
<213> ORGANISM: Mus musculus

<400> SEQUENCE: 17
tggatagtca gtgtttggtt cc                                      22
```

THERAPEUTIC AND DIAGNOSTIC METHODS INVOLVING BIGLYCAN AND UTROPHIN

CROSS-REFERENCE TO RELATED APPLICATIONS

This application is a United States National Stage Application filing under 35 U.S.C. § 371 of International Application No. PCT/US11/67432 filed on Dec. 27, 2011, which claims the benefit of U.S. Provisional Application No. 61/427,468, filed Dec. 27, 2010. The entire teachings of the referenced application are expressly incorporated herein by reference. International Application No. PCT/US11/67432 was published under PCT Article 21(2) in English.

GOVERNMENT GRANTS

This invention was made with government support under Grants HD023924, AR057698, RR015578, NS064295, P20 RR018757, KO8 HL072332, AR048871 and EY 013862 awarded by the National Institutes of Health. The government has certain rights in the invention.

SEQUENCE LISTING

The instant application contains a Sequence Listing which has been submitted in ASCII format via EFS-Web and is hereby incorporated by reference in its entirety. Said ASCII copy, created on Jun. 21, 2013, is named BURF013301.txt and is 59,266 bytes in size.

BACKGROUND OF THE INVENTION

The dystrophin-associated protein complex (DAPC) links the cytoskeleton to the extracellular matrix and is necessary for maintaining the integrity of the muscle cell/plasma membrane. The core DAPC consists of the cytoskeletal scaffolding molecule dystrophin and the dystroglycan and sarcoglycan transmembrane subcomplexes. The DAPC also serves to localize key signaling molecules to the cell surface, at least in part through its associated syntrophins (Brenman, et al. (1996) *Cell.* 84: 757-767; Bredt, et al. (1998), *Proc Natl Acad Sci USA.* 95: 14592). Mutations in either dystrophin or any of the sarcoglycans result in muscular dystrophies characterized by breakdown of the muscle cell membrane, loss of myofibers, and fibrosis (Hoffman, et al. 1987. *Cell.* 51: 919; Straub, and Campbell (1997) *Curr Opin Neurol.* 10: 168). Moreover, mutations in the extracellular matrix protein laminin-α2, which associates with the DAPC on the cell surface, is the basis of a major congenital muscular dystrophy (Helbling-Leclerc, et al. (1995) *Nat Genet.* 11: 216).

The α-/β-dystroglycan subcomplex forms a critical structural link in the DAPC. The transmembrane β-dystroglycan and the wholly extracellular α-dystroglycan arise by proteolytic cleavage of a common precursor (Ibraghimov, et al. (1992) *Nature* 355: 696; Bowe, et al. (1994) *Neuron* 12: 1173). The cytoplasmic tail of β-dystroglycan binds dystrophin, while the highly glycosylated, mucin-like α-dystroglycan binds to several ECM elements including agrin, laminin, and perlecan (Ervasti and Campbell, (1993) *J Cell Biol.* 122: 809; Bowe, et al. (1994) *Neuron.* 12: 1173; Gee, et al. (1994) *Cell* 77: 675; Hemler, (1999) *Cell* 97: 543). This binding to matrix proteins appears to be essential for assembly of basal lamina, since mice deficient in dystroglycan fail to form these structures and die very early in development (Henry, M. D. and K. P. Campbell (1998) *Cell.* 95: 859). β-Dystroglycan can bind the signaling adapter molecule Grb2 and associates indirectly with p125FAK (Yang, et al. (1995) *J. Biol. Chem.* 270: 11711; Cavaldesi, et al. (1999), *J. Neurochem.* 72: 01648). These binding properties suggest that dystroglycan may also serve to localize signaling molecules to the cell surface.

Several lines of evidence suggest that dystroglycan may also function in neuromuscular junction formation, in particular, in postsynaptic differentiation. For purposes of clarity, the components of the neuromuscular junction are summarized here. The major structural features of the neuromuscular junction (NMJ) or nerve-muscle synapse are the pre- and post-synaptic specializations of the motor neuron and muscle, respectively, the intervening synaptic basal lamina, and the specialized Schwann cell cap (Salpeter, et al (1987) *The Vertebrate Neuromuscular Junction.* New York, Alan R. Liss). The presynaptic apparatus is marked by ordered arrays of synaptic vesicles, a subset of which are poised to fuse with the plasma membrane at the active zones, and release acetylcholine that is recognized by acetylcholine receptors (AChRs) on the muscle, and ultimately results in electrical activation and contraction of the muscle (Heuser, et al. (1981) *J. Cell Biol.* 88: 564). Immediately across the 50 nm synaptic cleft from these zones are the crests of the postjunctional folds. These crests bristle with AChRs, which can reach densities of >10,000 molecules/$\mu m^2$ (Fertuck, et al. (1976) *J. Cell. Biol.* 69: 144). The localized and tightly regulated secretion of acetylcholine into the narrow synaptic cleft, coupled with the high AChR density in the postsynaptic membrane, ensures rapid and reliable synaptic transmission between neuron and muscle. Perturbations of these specializations, such as the decrease in the number of functional AChRs seen in myasthenia gravis, can lead to debilitating and often fatal clinical outcomes (Oosterhuis, et al. (1992) *Neurology & Neurosurgery* 5: 638).

The synaptic basal lamina (SBL) is interposed between the pre- and post-synaptic membranes and contains molecules important for the structure, function, and regulation of the neuromuscular junction (Bowe, M. A & Fallon, J. R., (1995) *Ann. Rev. Neurosci.* 18: 443; Sanes, et al. (1999) *Ann. Rev. Neurosci.* 22: 389). It consists of a distinct set of extracellular matrix molecules including specialized laminins, proteoglycans and collagens (Hall, et al. (1993) *Neuron* 10: (Suppl.) 99). The SBL also contains molecules essential for the regulation of synaptic structure and function including AChE, neuregulins, and agrin. The SBL thus serves both as a specialized structure for maintaining the localized differentiation of the synapse as well as a repository for essential regulatory molecules.

The molecular composition of the postsynaptic membrane is known in considerable detail. As noted above, the most abundant membrane protein is the AChR. The cytosolic AChR associated protein rapsyn (formerly known as the 43 kD protein) is present at stoichiometric levels with the receptor and is likely to form a key link between the cytosolic domain of the AChR and the cytoskeleton (Froehner, et al (1995) *Nature* 377: 195; Gautam, et al. (1995) *Nature* 377: 232). The postsynaptic membrane is also enriched in erbB2-4, some or all of which serve as neuregulin receptors (Altiok, et al. (1995) *EMBO J.* 14: 4258; Zhu, et al. (1995) *EMBO J.* 14: 5842), AChR and other molecules essential for nerve-muscle communication. The cytoskeletal elements can be broadly grouped into two subsets. Dystrophin and utrophin are members of the DAPC, and are linked to the synaptic basal lamina via the transmembrane heteromer α-/β-dystroglycan. The postsynaptic cytoskeleton is also enriched in several focal adhesion-associated molecules including α-actinin, vinculin, talin, paxillin, and filamin (Sanes, et al. (1999) *Ann. Rev. Neurosci.* 22: 389). The latter proteins probably communicate, directly or indirectly, with the extracellular matrix through integrins, some of which are enriched at synapses (Martin, et al. (1996) *Dev. Biol.* 174: 125). Actin is associated with both sets of cytoskeletal molecules (Rybakova et al. (1996) *J. Cell Biol.* 135: 661; Amann, et al. (1998) *J. Biol. Chem.* 273: 28419-23; Schoenwaelder et al. (1999) *Curr. Opin. Cell. Biol.* 11: 274). The functions of these specialized sets of proteins are considered below.

α-Dystroglycan binds the synapse organizing molecule agrin (Bowe, et al. (1994) *Neuron.* 12: 1173; Campanelli, et al. (1994) *Cell.* 77: 663; Gee, et al. (1994) *Cell.* 77: 675; Sugiyama, et al. (1994) *Neuron.* 13: 103; O'Toole, et al. (1996) *Proc Natl Acad Sci USA.* 93: 7369) (reviewed in Fallon and Hall, (1994) *Trends Neurosci.* 17: 469), and β-dystroglycan binds to the AChR-associated protein rapsyn (Cartaud, et al. (1998) *J Biol Chem.* 273: 11321). Further, agrin-induced AChR clustering on the postsynaptic membrane is markedly decreased in muscle cells expressing reduced levels of dystroglycan (Montanaro, et al. (1998) *J Neurosci.* 18: 1250). The precise role of dystroglycan in this process is unknown. Currently available evidence suggests that dystroglycan is not part of the primary agrin receptor, but rather may play a structural role in the organization of postsynaptic specializations (Gesemann, et al. (1995) *Biol.* 128: 625; Glass, et al. (1996) *Cell.* 85: 513; Jacobson, et al. (1998) *J Neurosci.* 18: 6340).

Another molecule that plays an important role in neuromuscular junction formation is the tyrosine kinase receptor MuSK, which becomes phosphorylated in response to agrin. However, agrin does not bind to MuSK and it is unclear how agrin stimulates MuSK. The existence of a co-receptor had been suggested. Activation of MuSK by antibody cross-linking is sufficient to induce the clustering of AChRs on cultured myotubes (Xie et al. (1997) *Nat. Biotechnol.* 15:768 and Hopf and Hoch (1998) *J. Biol. Chem.* 273: 6467) and a constitutively active MuSK can induce postsynaptic differentiation in vivo (Jones et al. (1999) *J. Neurosci.* 19:3376). However, MuSK phosphorylation is necessary but not sufficient for agrin-induced AChR clustering.

The realm of dystroglycan function ranges far beyond muscle. As noted above, mice defective in dystroglycan die long before muscle differentiation. In a surprising development, α-dystroglycan in non-muscle cells has been shown to function as a receptor for Lassa Fever and choriomeningitis fever viruses (Cao, W., et al., 1998, *Science.* 282: 2079), and on Schwann cells as a co-receptor for *Mycobacterium leprae* (Rambukkana, et al. (1998) *Science.* 282: 2076). Dystroglycan is also abundant in brain, but its function there is not understood (Gorecki, et al. (1994) *Hum Mol Genet.* 3: 1589; Smalheiser and Kim (1995) *J Biol Chem.* 270: 15425).

α-Dystroglycan comprises three known domains. An amino-terminal domain folds into an autonomous globular configuration (Brancaccio, et al. (1995) *Febs Lett.* 368: 139). The middle third of the protein is serine- and threonine-rich, and is highly glycosylated (Brancaccio, et al. (1997) *Eur J Biochem.* 246: 166). Indeed, the core molecular weight of α-dystroglycan is ~68 kDa, but the native molecule migrates on SDS-PAGE as a polydisperse band whose size ranges from 120-190 kDa, depending upon the species and tissue source (Ervasti and Campbell (1993) *J Cell Biol.* 122: 809; Bowe, et al. (1994) *Neuron.* 12: 1173; Gee, et al. (1994) *Cell.* 77: 675; Matsumura, et al. (1997) *J Biol Chem.* 272: 13904). Glycosylation of α-dystroglycan, probably in this middle third, is essential for its laminin- and agrin-binding properties.

It is clear that dystroglycan and the DAPC play crucial roles in a variety of processes in muscle as well as in other tissues. There is a need to develop diagnostic and therapeutic agents and methods which modulate functions of dystroglycan and/or the DAPC.

SUMMARY OF THE INVENTION

In certain aspects, the present disclosure provides a method of predicting a patient's response to biglycan therapy, comprising determining whether the patient has a decreased utrophin protein level or activity compared to a reference level, wherein a utrophin protein level or activity that is not decreased relative to the reference level indicates that the patient will likely respond to biglycan therapy.

In certain aspects, the present disclosure provides a method of monitoring an effect of biglycan therapy, comprising measuring the amount of membrane-associated utrophin in a patient receiving biglycan therapy, wherein an increased level of membrane-associated utrophin indicates that the biglycan therapy is effective.

In certain aspects, the present disclosure provides a method of adjusting a patient's dosage of a biglycan polypeptide, comprising administering a first dose of a biglycan polypeptide to a patient, measuring an amount of membrane-associated utrophin in the patient, comparing the amount of membrane-associated utrophin to a predetermined target level, and adjusting the dosage of the biglycan polypeptide responsive to a difference between the measured level and the target level.

In certain aspects, the present disclosure provides a method of measuring the activity of a biglycan polypeptide, comprising administering the biglycan polypeptide to a test cell that expresses utrophin and comparing an amount of membrane-associated utrophin in the test cell with an amount of membrane-associated utrophin in a control cell that did not receive biglycan polypeptide, wherein an increased amount of membrane-associated utrophin in the test cell is indicative of biglycan activity.

In certain aspects, the present disclosure provides a method of identifying a therapeutic for a biglycan-related condition, comprising administering a test compound to a test cell that expresses utrophin and comparing an amount of membrane-associated utrophin in the test cell with an amount of membrane-associated utrophin in a control cell that did not receive the test compound, wherein an increased amount of membrane-associated utrophin in the test cell indicates that the compound is a therapeutic for a biglycan-related condition.

The biglycan-related condition may be, for example, muscular dystrophy, a neuromuscular disease, a neurological disease, or a condition characterized by an abnormal neuromuscular junction or synapse. The muscular dystrophy may be, for example Duchenne's Muscular Dystrophy, Becker's Muscular Dystrophy, Congenital Muscular Dystrophy, Limb-girdle Muscular Dystrophy, or mytonic dystrophy. The test cell may be a muscle cell.

In certain aspects, the present disclosure provides a therapeutic composition comprising a biglycan polypeptide and a utrophin polypeptide.

In some embodiments, the composition of claim 21, wherein the utrophin polypeptide is at least 90% identical to SEQ ID NO: 13, or a fragment thereof.

In certain aspects, the present disclosure provides a therapeutic composition comprising a biglycan polypeptide and one or more of an anti-inflammatory agent, an agent that increases muscle mass, an agent that increases utrophin mRNA levels, an agent that increases utrophin protein levels, an agent that increases activity of the nNOS system, an agent that promotes repair of the muscle cell membrane, an agent that increases muscle regeneration, an agent that decreases fibrosis, and an antisense agent that promotes exon skipping in dystrophin.

In certain aspects, the present disclosure provides a method of treating a biglycan-related condition, comprising conjointly administering to a patient in need thereof an effective amount of a composition comprising a biglycan polypeptide and a utrophin polypeptide.

In certain aspects, the present disclosure provides a method of treating a biglycan-related condition, comprising conjointly administering to a patient in need thereof an effective amount of: (i) a composition comprising a biglycan polypeptide and (ii) one or more of an anti-inflammatory agent, an agent that increases muscle mass, an agent that increases utrophin mRNA levels, an agent that increases utrophin protein levels, an agent that increases activity of the nNOS system, an agent that promotes repair of the muscle cell membrane, an agent that increases muscle regeneration, an agent that decreases fibrosis, and an antisense agent that promotes exon skipping in dystrophin.

The anti-inflammatory agent may be, for example, Rofecoxibm or Celecoxib. The agent that increases muscle mass may be, for example, ACE-031, AMG-745, or MYO-029. The agent that increases utrophin mRNA levels may be, for example, BMN-195. The agent that increases utrophin protein levels may be, for example, SMT C1100. The agent that increases activity of the nNOS system may be, for example, Tadalafil, Vardenafil, or Sildenafil citrate. The agent that promotes repair of the muscle cell membrane may be, for example, dysferlin, MG53, or Cav3. The agent that increases muscle regeneration may be, for example, ACE-031 or AMG-745. The agent that decreases fibrosis may be, for example, a profibrotic factor antagonist or anti-fibrotic agent. The agent that promotes exon skipping may be, for example, AVI-4658, PRO51, or PRO44.

In certain aspects, the present disclosure provides method of treating a biglycan-related condition, comprising administering 0.5 mg/kg to 100 mg/kg of a biglycan polypeptide to a human patient in need thereof every 1 to 4 weeks. In some embodiments, the biglycan polypeptide is administered every 1-2 weeks, every 2-3 weeks, or every 3-4 weeks. In some embodiments, 1 mg/kg-100 mg/kg of biglycan polypeptide is administered. In some embodiments, 5 mg/kg-100 mg/kg of biglycan polypeptide is administered. In some embodiments, 10 mg/kg-100 mg/kg of biglycan polypeptide is administered. In some embodiments, 20 mg/kg-100 mg/kg of biglycan polypeptide is administered. In some embodiments, 50 mg/kg-100 mg/kg of biglycan polypeptide is administered. In some embodiments, 100 mg/kg/200 mg/kg of biglycan polypeptide is administered.

In certain aspects, the present disclosure provides method of treating a biglycan-related condition, comprising administering 0.1 mg/kg-100 mg/kg of a biglycan polypeptide to a human patient in need thereof every 1 to 4 weeks. For instance, the amount of biglycan may be 0.1 mg/kg-1.5 mg/kg. In some embodiments, the biglycan polypeptide is administered every 1-2 weeks, every 2-3 weeks, or every 3-4 weeks.

In some embodiments, the biglycan-related condition is muscular dystrophy, a neuromuscular disease, a neurological disease, or a condition characterized by an abnormal neuromuscular junction or synapse. The muscular dystrophy may be, for example, Duchenne's Muscular Dystrophy, Becker's Muscular Dystrophy, Congenital Muscular Dystrophy, Limb-girdle Muscular Dystrophy, or mytonic dystrophy.

In some embodiments, the biglycan polypeptide comprises an amino acid sequence which is at least 90% identical to SEQ ID NO: 9, or a fragment thereof. In some embodiments, the biglycan polypeptide comprises the amino acid sequence of SEQ ID NO: 9. In some embodiments, the biglycan polypeptide comprises an amino acid sequence which is at least 90% identical to SEQ ID NO: 10, or a fragment thereof. In some embodiments, the biglycan polypeptide comprises the amino acid sequence of SEQ ID NO: 10. In some embodiments, the biglycan polypeptide comprises an amino acid sequence which is at least 90% identical to SEQ ID NO: 11, or a fragment thereof. In some embodiments, the biglycan comprises the amino acid sequence of SEQ ID NO: 11.

The disclosure contemplates all combinations of any of the foregoing aspects and embodiments, as well as combinations with any of the embodiments set forth in the detailed description and examples.

BRIEF DESCRIPTION OF THE FIGURES

FIG. 10A-B. RhBGN fails to counter dystrophic pathology in mdx:utrn−/− double KO animals. (A) Mutant mice lacking both dystrophin and utrophin (mdx:utrn−/−) were injected at P19 with recombinant rhBGN or vehicle. Diaphragms were isolated 3 wk later, sectioned, and stained with H&E. Characteristic extensive muscle pathology of these double KO animals—areas of mononuclear cell infiltration and foci of necrosis/regeneration and centrally nucleated myofibers—was comparable in rhBGN- and vehicle-injected animals. (Scale bar=50 μm.) (B) RhBGN administration does not decrease CNFs in mdx:utrn−/− mice. Percentages of centrally nucleated muscle fibers were determined from the H&E-stained diaphragm sections from rhBGN and vehicle injected mdx:utrn−/− (n=2 vehicle-injected and 3 rhBGN-injected mice; unpaired Student t test, P=0.45).

FIG. 19A-B shows that S5A-S10 biglycan decreases muscle damage in mdx mice. (a) P18 Mdx mice were injected weekly intraperitoneally for two weeks with either vehicle or S5A-S10 biglycan and the levels of serum Creatine Kinase (sCK) were measured. The levels of sCK were reduced over 2-fold in the biglycan-injected animals. (p<0.01; n=4). (b) Mdx mice were injected at P18 and P25 with the indicated amounts of his-tagged S5A-S10A recombinant human biglycan (T2-rhBGN). Serum was harvested at P32. (ANOVA p=0.002; *post-hoc pairwise comparison p<0.05.)

FIG. 20 shows the functional efficacy of S5A-S10A rhBGN. Mdx mice were dosed with 10 mg/kg SA-rhBGN for 3 months at the intervals indicated. Eccentric contraction measurements were made on isolated muscle.

FIGS. 22 A and B show that the administration of biglycan to muscle tissue of a biglycan-null mouse restores collagen VI levels. A. Injected recombinant biglycan localizes to the surface of muscle cells. This image shows two fields of view showing immunolabeling of right quadriceps muscle from a biglycan null mouse with a biglycan antibody, four days post injection with 50 µg of purified recombinant biglycan proteoglycan. Light microscopy of the field showing deposits of India ink is shown in the upper panels. Injected purified recombinant biglycan proteoglycan was detected with the antibody 2A5. The lower panels show biglycan immunofluorescence in the same fields as the upper panels, and show that the injected biglycan persists in the muscle and localizes to the muscle fiber membranes. Similar results were observed in 6 animals. B. Injected recombinant biglycan upregulates collagen VI levels in vivo. This image shows two fields of view showing immunolabeling of right quadriceps muscle from a biglycan null mouse with an antibody to collagen VI shown four days after injection with 50 µg of purified recombinant biglycan proteoglycan. Light microscopy of the same field shows deposits of India ink (identifying the injection site). The lower panels show collagen immunofluorescence in the same fields as the upper panels, and show that injected purified recombinant biglycan proteoglycan upregulates collagen VI expression at the muscle fiber membranes. Similar results were observed in six animals.

FIG. 23 depicts the results of lectin blotting assays of recombinant NG, PG and SA forms of biglycan. Top panel, Ponceau staining and lectin blotting images. Bottom panel, summary of results.

FIG. 24 depicts the results of N-linked glycosylation analysis of the NG and SA forms of biglycan. The sequence "(R)MIEN@GSLSFLPTLR(E)", not including the two residues in parentheses, corresponds to residues 267-280 of SEQ ID NO: 9. The sequence "(K)LLQVVYLHSNN@ITK (V)", not including the two residues in parentheses, corresponds to residues 301-314 of SEQ ID NO: 9. An @ indicates the site of N-glycosylation.

DETAILED DESCRIPTION OF THE INVENTION

I. Overview

Figure 1:
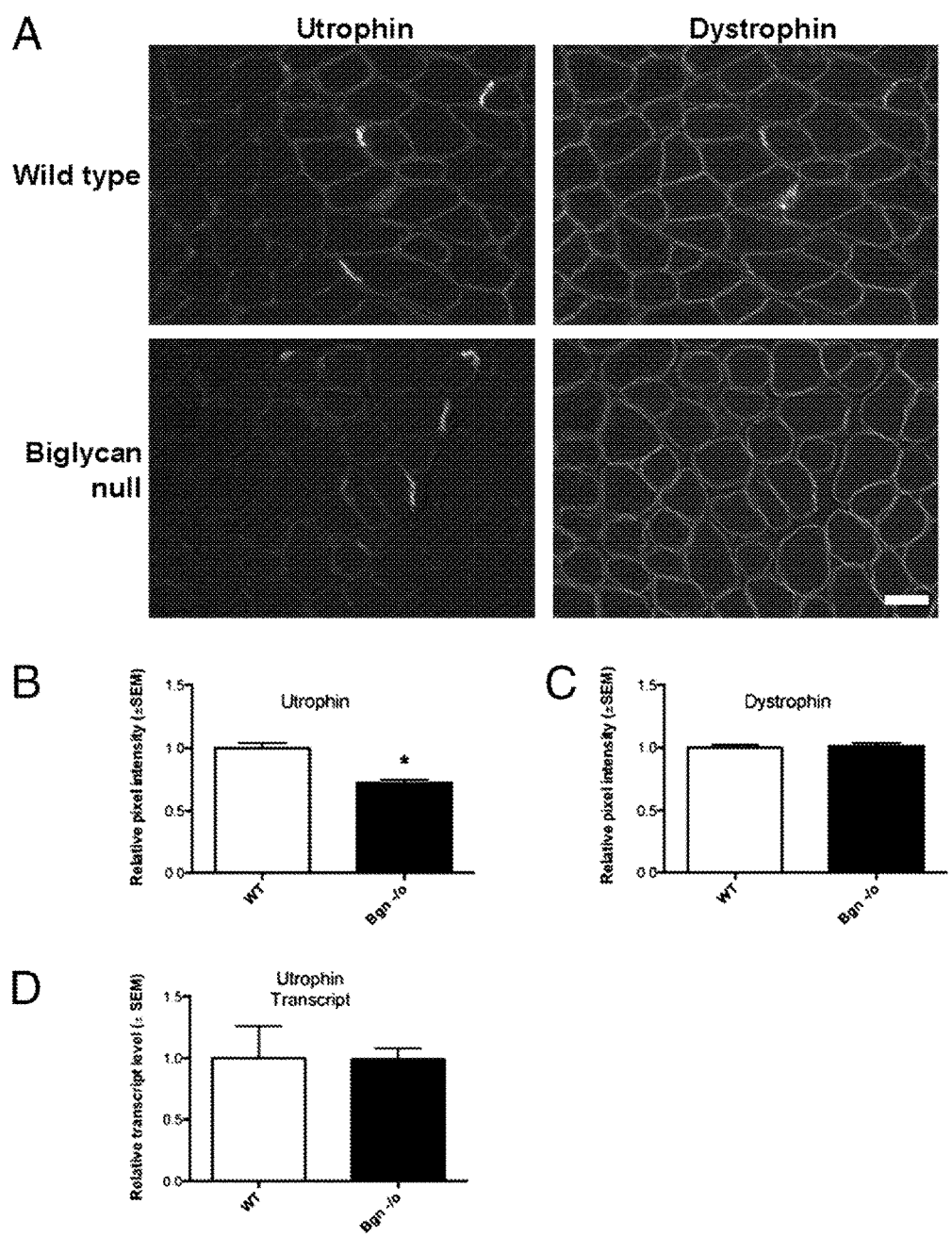
FIG. 1A-D show utrophin levels and localization in wild-type and biglycan null mice. Utrophin is reduced at the sarcolemma of immature bgn–/o mice. (A) Quadriceps muscles from congenic P14 WT (Upper Panels) DJS and bgn–/o (Lower Panels) mice were harvested, sectioned, mounted on the same slides, and immunostained for dystrophin and utrophin. Utrophin expression is decreased in these developing biglycan null mice compared with WT mice, whereas dystrophin expression is not detectably altered. (Scale bar=25 µm.) (B) Quantification of sarcolemmal utrophin expression. Images of utrophinstained muscle sections as prepared in A were acquired and the levels of utrophin immunostaining at the perijunctional sarcolemma were measured as described in Materials and Methods. A total of 50 sarcolemmal segments from each of three animals from each genotype were analyzed. Utrophin immunoreactivity was decreased 28% in sections from bgn–/o mice compared with WT (Bgn–/o: 0.72±0.03, WT: 1.0±0.04, unpaired Student t test, P<0.0001; n=150 sarcolemmal segments from three mice of each genotype). (C) Quantification of perijunctional sarcolemmal dystrophin. Dystrophin-stained sections were imaged and measured as in B. Dystrophin immunoreactivity was equivalent in P14 WT and bgn–/o sections (Bgn–/o: 1.01±0.03, WT: 1.00±0.03, unpaired Student t test, P=0.76). (D) Quantitative real-time PCR analysis of utrophin transcripts in P14 WT and bgn–/o mice. Total RNA was extracted from quadriceps muscles from WT and bgn–/o mice and used for cDNA synthesis. Expression of utrophin mRNA was indistinguishable in WT and Bgn–/o muscles (WT: 1.0±0.26, Bgn–/o: 0.99±0.09, n=3 animals from each genotype).

The instant disclosure provides biglycan-containing compositions and methods for treating and/or preventing diseases or conditions associated with a dysfunctional DAPC, an unstable cellular structure, a defect in neuromuscular junctions or synapses, or a collagen VI deficiency. Such diseases include, but are not limited to, muscular dystrophies, such as Duchenne, Limb-girdle, other myopathies, neuromuscular disorders, and neurological disorders.

Certain aspects of the disclosure are based on the novel discovery that a biglycan therapeutic promotes proper utrophin localization to the cell membrane, and that a lack of utrophin reduces the efficacy of a biglycan therapeutic. Consequently, this disclosure provides methods for determining whether a biglycan therapy is likely to be successful, in particular by assaying utrophin levels, localization, or function.

Furthermore, in view of the wide tissue distribution of DAPCs and dystroglycans, biglycan is likely to play a role in regulating signaling through the cytoplasmic membrane and/or maintaining the integrity of cytoplasmic membranes of cells other than muscle cells. For example, dystroglycan or other DAPC components are abundant in brain, kidney, and heart. Thus, the instant disclosure provides, more generally, biglycan-containing compositions and predictive methods for diseases or disorders associated with an abnormality of a membrane protein complex with which the biglycan polypeptide interacts, e.g., the DAPC or MuSK receptor.

Since dystroglycan is known to be a receptor used by microorganisms for entering cells (e.g., Lassa Fever and choriomeningitis fever viruses), the biglycan-containing therapeutics and predictive methods described herein can be used with respect to infections by such microorganisms. Without wanting to be limited to a specific mechanism of action, biglycan therapeutics may hinder or inhibit binding of the microorganism to dystroglycan.

Both human biglycan (e.g., in Fischer et al. as "bone small proteoglycan" J. Biol. Chem. 264: 4571 (1996); GenBank Accession No. J04599; SEQ ID NO: 9) and DAG-125 isolated from Torpedo electric organ have been shown to interact with DAPC components. Based on sequence homologies between the two proteins and similar biological activities (further described herein), it is believed that the human biglycan (SEQ ID NO: 9) may be the human ortholog of the Torpedo DAG-125. Alternatively, the human ortholog of the Torpedo DAG-125 may be a protein that is highly related to human biglycan. For purposes of clarity, the term "biglycan" as used herein is intended to include the human biglycan (SEQ ID NO: 9) and Torpedo DAG-125, as well as their homologs.

Duchenne muscular dystrophy (DMD) is a hereditary disease that affects ~1:3,500 boys, the majority of whom will die by their mid twenties (1). DMD is caused by mutations in dystrophin that result in the faulty assembly and function of an ensemble of structural and signaling molecules at the muscle cell surface, termed the dystrophin-associated protein complex (DAPC) (2-4). There are currently no treatments that target the primary pathology of DMD.

One attractive therapeutic approach for DMD is the stabilization of the muscle cell membrane through up-regulation of utrophin, a dystrophin homolog. Transgenic overexpression of utrophin rescues dystrophic pathology and restores function in the dystrophin-deficient mdx mouse (5-7). In mature muscle, utrophin expression is restricted to the neuromuscular and myotendinous junctions. However, utrophin is expressed over the entire myofiber in developing and regenerating muscle (8-10). These observations raise the possibility that marshalling pathways that normally regulate utrophin expression in developing muscle could be a productive approach for developing DMD treatments.

The extracellular matrix protein biglycan plays an important role in developing muscle. In both humans and mice, biglycan is most highly expressed in immature and regenerating muscle (11, 12). Biglycan is a component of the DAPC, where it binds to α-dystroglycan (13) and α- and γ-sarcoglycan (14). Biglycan regulates the expression of the sarcoglycans as well as dystrobrevins, syntrophins, and nNOS, particularly in immature muscle. Finally, biglycan is important for timely muscle regeneration (11).

Locally delivered recombinant human biglycan (rhBGN) incorporates into the extracellular matrix of bgn-/o muscle where it persists for at least 2 wk and rescues the expression of several DAPC components (15). These results suggest that rhBGN will enhance function in muscle that lacks dystrophin. Here we show that utrophin is down-regulated in immature biglycan null (bgn-/o) mice and that rhBGN up-regulates membrane-associated utrophin in cultured myotubes. Importantly, rhBGN can be delivered systemically to dystrophin-deficient mdx mice, where it up-regulates utrophin and other DAPC components at the sarcolemma, ameliorates muscle pathology, and improves function. Several lines of evidence indicate that biglycan acts by recruiting utrophin to the plasma membrane. Thus, rhBGN may be used as a therapeutic for DMD.

II. Definitions

For convenience, the meaning of certain terms and phrases employed in the specification, examples, and appended claims are provided below.

"GAGs" refers to glycosaminoglycans, used interchangeably herein with "mucopolysaccharides," which are long, unbranched polysaccharide chains composed of repeating disaccharide units. One of the two sugars is always an amino sugar (N-acetylglucosamine or N-acetylgalactosamine). Glycosaminoglycans are covalently linked to a serine residue of a core protein, to form a proteoglycan molecule.

The term "glycoprotein" refers to a protein which contains one or more carbohydrate groups covalently attached to the polypeptide chain. Typically, a glycoprotein contains from 1% to 60% carbohydrate by weight in the form of numerous, relatively short, branched oligosaccharide chains of variable composition. In contrast to glycoproteins, proteoglycans are much larger (up to millions of daltons), and they contain 90% to 95% carbohydrate by weight in the form of many long, unbranched glycosaminoglycan chains.

The term "biglycan" refers to polypeptides having at least one biological activity of human biglycan or Torpedo DAG-125. Preferred biglycans include Torpedo DAG-125 (comprising at least one of SEQ ID NOs: 1-3), human biglycan (SEQ ID NO: 9), as well as homologs and fragments thereof. Preferred homologs are proteins or peptides having at least about 70% identity, at least about 75% identity, at least about 80% identity, at least about 85% identity, at least about 90% identity, at least about 95% identity, and even more preferably, at least about 98 or 99% identity. Even more preferred homologs are those which have a certain percentage of homology (or identity) with human biglycan or Torpedo DAG-125 and have at least one biological activity of these molecules. The term biglycan is not limited to the full length biglycan, but includes also fragments (portions) having at least one activity of biglycan. Biglycan, as the term is used herein, refers to forms of the polypeptide both with and without the GAG side chains.

The term "wild-type human biglycan" refers to the protein described in Fischer et al. J. Biol. Chem. 264: 4571 (1989), having GenBank Accession No. J04599, and the amino acid sequence set forth in SEQ ID NO: 9. A cDNA sequence encoding the wild-type human biglycan protein is set forth in SEQ ID NO: 7, and the open reading frame thereof as SEQ ID NO: 8.

The term "biglycan-related polypeptide" refers to certain polypeptides having at least one activity of biglycan, and the term does not include wild-type biglycan. Wild-type biglycan and biglycan-related polypeptides are both encompassed within the term "biglycan therapeutic".

The term "biglycan core" refers to a biglycan that does not include GAG chains.

As described herein, the term "biglycan-related therapeutic" refers to a biglycan-like polypeptide in which the two amino acid residues corresponding to the two glycanated serine residues of a wildtype biglycan protein (e.g., Torpedo DAG-125 or a mammalian, preferably human, biglycan) are deleted or replaced by another amino acid (preferably glycine or an amino acid with an alkyl side chain, such as alanine) such that the polypeptide lacks glycosaminoglycan (GAG) side chains (i.e., because it lacks the wild-type glycanation sites). In addition, a biglycan-related therapeutic has one or more of the characteristics and biological activities of a wildtype biglycan. For example, a biglycan-related therapeutic may have one or more of the following characteristics: a molecular weight of between about 35 and about 55 kDa; an amino acid sequence at least 80%, 85%, 90%, 95%, or 99% identical to one or more of SEQ ID NOs: 1-6 or to residues 38-365 of SEQ ID NO: 9, 10, or 11; and one of more biological activities of biglycan, as listed infra, under the corresponding definition. A number of biglycan-related therapeutics are described in International Application WO 2011/146480, which is herein incorporated by reference. A biglycan-related therapeutic is a type of biglycan therapeutic.

The term "biglycan therapeutic" further includes portions of the biglycan polypeptides described herein and which have at least one biological activity of a wildtype biglycan. The term "biglycan therapeutic" also includes a peptidomimetic or derivative thereof, or a nucleic acid encoding a biglycan-like polypeptide.

A "biological activity of biglycan" is intended to refer to one or more of: the ability to maintain the integrity of a plasma membrane; the ability to stabilize DAPCs on plasma membranes; the ability to bind to one or more components of DAPCs; e.g., binding to α-dystroglycan (in the case of certain biglycans such as wild-type human biglycan), binding to a sarcoglycan component, such as α-sarcoglycan or γ-sarcoglycan; binding to MuSK; binding to collagen VI; stimulating the formation of neuromuscluar junctions, such as by stimulating postsynaptic differentiation; potentiation of AChR aggregation, e.g., agrin-induced AChR aggregation; phosphorylation of DAPC components, e.g., sarcoglycans; stimulation MuSK phosphorylation or potentiating agrin-induced MuSK phosphorylation; elevating utrophin levels, and promoting utrophin localization to the cell membrane. In certain embodiments, the biglycan binds to MuSK, α-sarcoglycan, γ-sarcoglycan, and collagen VI, but does not bind to α-dystroglycan.

The term "biglycan nucleic acid" refers to a nucleic acid encoding a biglycan protein, e.g., a nucleic acid encoding a protein having SEQ ID NO: 9.

The term "abnormal" is used interchangeably herein with "aberrant" and refers to a molecule, or activity with differs from the wild type or normal molecule or activity.

The term "DAPC" refers to "dystrophin-associated protein complex", a membrane complex which comprises dystrophin, α- and β-dystroglycans, and the sarcoglycan transmembrane complex.

"Sarcoglycans" exit in different forms including α-, β-, γ-, δ-, and ε-sarcoglycans. Certain sarcoglycans are specific for certain tissues, e.g., α- and δ-sarcoglycans are skeletal muscle specific.

"Dystrophin-associated proteins" includes proteins or glycoproteins, such as α-dystroglycan, dystrobrevin, sarcospan and the syntrophins.

The term "AChR" refers to acetylcholine receptor.

The term "SLRP" refers to small leucine rich repeat proteoglycan.

The term "MuSK" used interchangeably herein with "muscle specific kinase," refers to a protein tyrosine kinase that is expressed in normal and denervated muscle, as well as other tissues including heart, spleen, ovary or retina (See Valenzuela, D., et al., 1995, *Neuron* 15: 573-584). The tyrosine kinase has alternatively been referred to as "Dmk" for "denervated muscle kinase." Thus, the terms MuSK and Dmk may be used interchangeably. The protein appears to be related to the Trk family of tyrosine kinases, and is further described in U.S. Pat. No. 5,814,478.

The term "MuSK activating molecule" as used herein refers to a molecule which is capable of inducing phosphorylation of the MuSK receptor in the context of a differentiated muscle cell. One such activating molecule is agrin.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

A "myoblast" is a cell that by fusion with other myoblasts, gives rise to myotubes that eventually develop into skeletal muscle fibres. The term is sometimes used for all the cells recognisable as immediate precursors of skeletal muscle fibres. Alternatively, the term is reserved for those postmitotic cells capable of fusion, others being referred to as presumptive myoblasts.

"Myofibril" is a long cylindrical organelle of striated muscle, composed of regular arrays of thick and thin filaments, and constituting the contractile apparatus.

"Myotubes" are elongated multinucleate cells (three or more nuclei) that contain some peripherally located myofibrils. They are formed in vivo or in vitro by the fusion of myoblasts and eventually develop into mature muscle fibres that have peripherally located nuclei and most of their cytoplasm filled with myofibrils.

"Utrophin" (dystrophin associated protein) is an autosomal homologue of dystrophin (of size 395 kD) localized near the neuromuscular junction in adult muscle, though in the absence of dystrophin (i.e., in Duchenne muscular dystrophy), utrophin is also located on the cytoplasmic face of the sarcolemma. A human mRNA sequence of utrophin is provided as SEQ ID NO: 12, and a polypeptide sequence of human utrophin is provided as SEQ ID NO: 13. SEQ ID NOS: 12 and 13 may be found under Genbank Accession Number X69086.1.

As used herein, the term "transfection" means the introduction of a nucleic acid, e.g., an expression vector, into a recipient cell by nucleic acid-mediated gene transfer. The term "transduction" is generally used herein when the transfection with a nucleic acid is by viral delivery of the nucleic acid. "Transformation", as used herein, refers to a process in which a cell's genotype is changed as a result of the cellular uptake of exogenous DNA or RNA, and, for example, the transformed cell expresses a recombinant form of a polypeptide or, in the case of anti-sense expression from the transferred gene, the expression of a naturally-occurring form of the recombinant protein is disrupted.

As used herein, the term "transgene" refers to a nucleic acid sequence which has been introduced into a cell. Daughter cells deriving from a cell in which a transgene has been introduced are also said to contain the transgene (unless it has been deleted). A transgene can encode, e.g., a polypeptide, partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene). Alternatively, a transgene can also be present in an episome. A transgene can include one or more transcriptional regulatory sequences and any other nucleic acid, (e.g., intron), that may be necessary for optimal expression of a selected coding sequence.

As used herein, the term "vector" refers to a nucleic acid molecule capable of transporting another nucleic acid to which it has been linked. One type of vector is an episome, i.e., a nucleic acid capable of extra-chromosomal replication. Appropriate vectors are those capable of autonomous replication and/or expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops which, in their vector form are not bound to the chromosome. In the present specification, "vector", unless otherwise specified, signifies "plasmid", as the plasmid is the most commonly used form of vector. However, the disclosure also provides such other forms of expression vectors which serve equivalent functions and which become known in the art subsequently hereto.

"Derived from" as that phrase is used herein indicates a peptide or nucleotide sequence selected from within a given sequence. A peptide or nucleotide sequence derived from a named sequence may contain a small number of modifications relative to the parent sequence, in most cases representing deletion, replacement or insertion of less than about 15%, preferably less than about 10%, and in many cases less than about 5%, of amino acid residues or base pairs present in the parent sequence. In the case of DNAs, one DNA molecule is also considered to be derived from another if the two are capable of selectively hybridizing to one another.

The terms "chimeric", "fusion" and "composite" are used to denote a protein, peptide domain or nucleotide sequence or molecule containing at least two component portions which are mutually heterologous in the sense that they are not, otherwise, found directly (covalently) linked in nature. More specifically, the component portions are not found in the same continuous polypeptide or gene in nature, at least not in the same order or orientation or with the same spacing present in the chimeric protein or composite domain. Such materials contain components derived from at least two different proteins or genes or from at least two non-adjacent portions of the same protein or gene. Composite proteins, and DNA sequences which encode them, are recombinant in the sense that they contain at least two constituent portions which are not otherwise found directly linked (covalently) together in nature.

The term "modulate" refers to inhibiting or stimulating.

The terms "activating a postsynaptic membrane" refers to the stimulation of the transfer of a signal at neuromuscular junction, generally, from a nerve cell to a mucle cell. Activation usually includes the stimulation of aggregation of AChR on the cell membrane at the neuromuscular junction; and/or the phosphorylation of MuSK. Activation results in induction of postsynaptic differentiation.

The term "treating" with regard to a subject, refers to improving at least one symptom of the subject's disease or disorder. Treating can be curing the disease or condition or improving it, but reducing at least certain symptoms of it.

III. Biglycan Therapeutic Polypeptides

The methods and compositions disclosed herein may use wild-type or mutant biglycan therapeutics. Such therapeutics may be used, for example, in maintaining the integrity of plasma cell membranes, in particular, biglycan therapeutics which stabilize dystrophin associated protein complexes (DAPC) in these membranes, thereby preventing the disintegration of the membranes. The biglycan therapeutics may also stimulate neuromuscular junction formation, such as by stimulating postsynaptic membrane differentiation, and more generally biglycan therapeutics which stimulate synapse formation.

In certain embodiments, the biglycan therapeutic is a wild-type biglycan polypeptide or fragment thereof. For instance, the polypeptide may comprise the sequence of SEQ ID NO: 9 or an active portion thereof. In some embodiments, the polypeptide comprises SEQ ID NO: 9. In some embodiments, the biglycan polypeptide does not comprise any glycosaminoglycan (GAG) side chain.

In some embodiments, the biglycan therapeutic polypeptide comprises an amino acid sequence at least 80%, 90%, 95%, 98, or 99% identical to amino acids 38-365 of SEQ ID NO: 9. In some embodiments, the biglycan therapeutic polypeptide comprises the amino acid sequence identical to amino acids 38-365 of SEQ ID NO: 9. In some embodiments, the biglycan therapeutic polypeptide is encoded by a nucleic acid which hybridizes under stringent conditions to SEQ ID NO: 8.

In certain other embodiments, the biglycan polypeptide is a biglycan polypeptide such as a biglycan mutant polypeptide which comprises at least two amino acid residue substitutions at two serine residues (e.g., at residues 42 and 47 of SEQ ID NO: 9) such that the biglycan polypeptide does not comprise any glycosaminoglycan (GAG) side chain. For example, the biglycan mutant polypeptide may comprise the amino acid sequence of SEQ ID NO: 10, or a fragment thereof. SEQ ID NO: 10 is a consensus sequence, wherein residues 42 and 47 can each independently be absent or can be any amino acid except serine or threonine. In certain embodiments, residues 42 and 47 of SEQ ID NO: 10 are both present. In certain embodiments, the biglycan mutant polypeptide comprises the amino acid sequence of SEQ ID NO: 11, or a fragment thereof. SEQ ID NO: 11 is similar to SEQ ID NO: 9, but includes the mutations S42A and S47A.

In some embodiments, the biglycan therapeutic polypeptide comprises an amino acid sequence which is at least 80%, 90%, 95%, 98, or 99% identical to SEQ ID NO: 9, or a fragment thereof. In some embodiments, the two serine residues are at positions corresponding to residues 42 and 47 of SEQ ID NO: 9. In some embodiments, the biglycan therapeutic polypeptide comprises the amino acid sequence of SEQ ID NO: 10, or a fragment thereof. In some embodiments, the biglycan therapeutic polypeptide comprises the amino acid sequence of SEQ ID NO: 11, or a fragment thereof. In some embodiments, the biglycan therapeutic polypeptide comprises one or more LRRs in SEQ ID NO: 9.

The biglycan therepautic may have one or more useful biological activities. In preferred embodiments, the biglycan therapeutic polypeptide increases utrophin association with the cell membrane. In preferred embodiments, the biglycan therapeutic upregulates utrophin protein levels. In some embodiments, the biglycan therapeutic does not upregulate utrophin mRNA levels. In certain embodiments, the biglycan therapeutic polypeptide activates muscle specific kinase (MuSK) on the cell. In some embodiments, the biglycan therapeutic polypeptide potentiates agrin-induced phosphorylation of MuSK. In some embodiments, the biglycan therapeutic polypeptide binds to MuSK. In some embodiments, the biglycan therapeutic polypeptide binds to a α-sarcoglycan and/or γ-sarcoglycan. In some embodiments, the biglycan therapeutic polypeptide induces phosphorylation of sarcoglycans. In some embodiments, the biglycan therapeutic polypeptide potentiates agrin-induced clustering of acetylcholine receptors (AChR).

The subject biglycan polypeptides may be produced using any suitable technique. Numerous such techniques are well known in the art. For example, modification of the biglycan-encoding DNA sequence may be achieved by altering one or more nucleotides employing site-directed mutagenesis. In general, the technique of site specific mutagenesis is well known in the art as exemplified by publications (Carter et al., 1986, Biochem J., 237(1): 1-7; Sambrook, et al., 1989, Molecular Cloning: A Laboratory Manual, 2nd Ed., Cold Spring Harbor Laboratory, Cold Spring Harbor, N.Y.). As will be appreciated, the technique typically employs a phagemid vector which exists in both a single stranded and double stranded form. Alternatively, mutants may be generated by using PCR™. Typical vectors useful in site-directed mutagenesis include vectors such as the M13 phage (Messing et al., 1981) or pUC 119. These vectors are readily commercially available and their use is generally well known to those skilled in the art. Alternatively, methods of site-directed mutagenesis employing double stranded plasmids or phagemids and the like are also well known in the art and may also be used.

In a particular embodiment, a biglycan polypeptide binds to one or more components of the DAPC. In preferred embodiments, the biglycan polypeptide promotes proper utrophin localization to the cell membrane. The biglycan therapeutic also preferably binds to a sarcoglycan component, such as α-sarcoglycan. In an even more preferred embodiment, the biglycan therapeutic binds to a component of the sarcoglycan complex, e.g., selected from α-sarcoglycan, γ-sarcoglycan and δ-sarcoglycan. The component of the sarcoglycan to which the biglycan polypeptide binds is preferably α-sarcoglycan. Generally, biglycan therapeutic peptides contact one or more components of the DAPC, e.g., to thereby stabilize the complex and reduce destabilization of the plasma membrane resulting from an abnormal DAPC complex, such as those seen in muscular dystrophies.

In certain embodiments, the biglycan therapeutic binds to MuSK, α-sarcoglycan, γ-sarcoglycan, and collagen VI, but does not bind to α-dystroglycan. Even in embodiments where the biglycan is unable to bind α-dystroglycan, there are still mechanisms by which biglycan could influence α-dystroglycan indirectly. The following mechanisms should be considered non-binding theories: 1) biglycan may bind collagen VI and recruit other ligands for alpha-DG; this mechanism could occur in muscle or non-muscle tissues, 2) biglycan could bind to MuSK and thus indirectly recruit α-dystroglycan, and 3) since biglycan is known to dimerize, mutant biglycan incapable of binding α-dystroglycan might heterodimerize with the endogenous biglycan proteoglycan and thus recruit α-dystroglycan.

In other embodiments, biglycan therapeutics bind to the receptor tyrosine kinase MuSK. Such compounds can bind to MuSK and/or a component of the sarcoglycan complex, e.g., α-sarcoglycan. In preferred embodiments, a biglycan therapeutic activates MuSK and induces phosphorylation of a and/or γ-sarcoglycan.

The subject biglycan therapeutics preferably bind specifically to one or more of the above-cited molecules, i.e., they do not significantly or at a detectable level bind to other molecules to produce an undesirable effect in the cell. The biglycan therapeutics preferably bind to one or more of the above-cited molecules with a dissociation constant of $10^{-6}$ or less, and even more preferably with a dissociation constant of $10^{-7}$, $10^{-8}$, $10^{-9}$, $10^{-10}$, $10^{-11}$, $10^{-12}$, or $10^{-13}$ M or less. The dissociation constant can be determined according to methods well known in the art.

Binding assays for determining the level of binding of a biglycan therapeutic to a component of the DAPC or to MuSK or for identifying members of, e.g., a library of compounds which bind to these molecules are known in the art and are also further described herein. Methods for preparing DAPC components or MuSK for use in such assays are also known. Such components can be isolated from tissue or, when they are proteins, can be prepared recombinantly or synthetically. Their nucleotide and amino acid sequences are publicly available, e.g., from GenBank, or from publications.

In other preferred embodiments, biglycan therapeutics have one or more biological activities of biglycan, in addition to, or instead of, being able to bind one or more components of the DAPC and/or MuSK. For example, a biglycan therapeutic can stimulate neuromuscular junction formation, in particular, postsynaptic membrane differentiation, including inducing aggregation of AChRs and/or stimulating agrin-induced tyrosine phorphorylation of MusK.

In certain embodiments, a biglycan therapeutic potentiates agrin-induced clustering of AChR in a biphasic manner, with a potentiation at low concentrations and a depotentiation at higher levels. Optionally, the biglycan therapeutic does not inhibit agrin-induced clustering of AChR at high concentrations.

In certain embodiments, a biglycan therapeutic decreases muscle damage in vivo.

The biglycan therapeutic can be a protein or derivative thereof, a peptidomimetic or derivative thereof, or a nucleic acid (e.g., a nucleic acid encoding a biglycan mutant polypeptide). Peptidomimetics can be prepared, e.g., based on the structure of the biglyan. Generally, the biglycan therapeutic has the required characteristics, e.g., binding to α-sarcoglycan and/or other DAPC components.

In certain embodiments, the biglycan therapeutic comprises one or more of the following amino acid sequence: IQAIEFEDL (SEQ ID NO: 1); LGLGFNEIR (SEQ ID NO: 2); and TSYHGISLFNNPVNYWDVL (SEQ ID NO: 3), or amino acid sequences related thereto, such as amino acid sequences from the mammalian ortholog of the Torpedo protein from which these amino acid sequences were obtained. The biglycan therapeutic preferably contain all three of these sequences or sequences related thereto. For example, the biglycan therapeutic can comprise one or more of the following amino acid sequences, which are part of human biglycan: IQAIELEDL (SEQ ID NO: 4); LGLGHNQIR (SEQ ID NO: 5); and AYYNGISLFNNPVPYWEVQ (SEQ ID NO: 6).

Although compositions including, and methods using, Torpedo DAG-125 are within the scope of the present disclosure, preferred compositions and methods are those relating to mammalian, including vertebrate, homologs of Torpedo DAG-125, referred to herein as orthologs of Torpedo DAG-125. Preferred orthologs of Torpedo DAG-125 are human, rodent, murine, canine, feline, ovine, and bovine orthologs. The mammalian ortholog of DAG-125 is biglycan.

Other mammalian orthologs of Torpedo DAG-125 can be isolated by screening libraries with probes containing nucleotide sequences encoding one or more of SEQ ID NOs: 1-3. Numerous other methods are available for cloning mammalian orthologs of Torpedo DAG-125. For example, antibodies to Torpedo DAG-125 can be produced and used to screen mammalian expression libraries. The identification of the cloned proteins as mammalian ortholgogs of Torpedo DAG-125 can be established by performing the same biological assays as those described in the Examples employing Torpedo DAG-125.

Thus, the polypeptides provided herein can also be members of the family of small leucine-rich proteoglycans (SLRP), also referred to as "nonaggregating or small dermatan-sulfate proteoglycans" because of their inability to interact with hyaluronan, or because of their type of glycosaminoglycans, respectively. SLRPs are organized into three classes based on their protein and genomic organization. All SLRPs are characterized by a central domain containing leucine rich repeats (LRR) flanked at either side by small cysteine clusters. The SLRPs are described, e.g., in Iozzo et al. (1998) *Ann. Rev. Biochem.* 67:609, specifically incorporated herein by reference.

SLRP protein cores range from ~35-45 kD with one or two GAG chains attached at the extreme N-terminus. The general structure of the SLRP protein core consists of a tandem array of 6-10 leucine-rich repeats (LRR) flanked by domains with conserved, disulfide-bonded cysteines. Depending upon the extent of glycosylation and number of GAG chains, the native molecular weight ranges from ~100-250 kD. On the basis of their sequence homology, Iozzo, supra, has proposed that SLRPs be grouped into three classes consisting of: 1) biglycan and decorin; 2) fibromodulin, lumican, keratocan, PREPLP, and osteoadherin; and 3) epiphycan and osteoglycin. The most compelling feature of the SLRP protein core are the LRRs. Such repeats (24 aa each in the SLRPs) mediate protein-protein interactions in a wide variety of intracellular, transmembrane, and extracellular contexts (Kobe & Deisenhofer, (1994) *Trends Biochem. Sci.* 19: 415-21). The neurotrophin binding site on trkB, for example, is an LRR (Windisch et al., (1995) *Biochemistry* 34: 11256-63). The repeats are thought to have a general structure of an α-helix followed by beta-sheet in an anti-parallel array, although sequence analysis has suggested that this order might be reversed in the SLRPs (Hocking et al., (1998) *Matrix Biol.* 17: 1-19). It is likely that the conserved residues of each repeat dictate their secondary structure, while the intervening amino acids determine specificity of ligand binding.

SLRPs suitable for use in the methods and compositions herein include mutants of Class I SLRPs, such as biglycan and decorin. The partial amino acid sequences of DAG-125, the Torpedo proteoglycan which was shown to bind to α-dystroglycan (see, for example, U.S. Pat. No. 6,864,236) shows strong homology to human biglycan: a 78% identity was found in a total of 37 amino acid long sequence. Biglycan from rodent, pig and human are >95% identical. Decorin and biglycan from human are only 55% identical. Such homology is consistent with decorin and biglycan having both shared and unique functions. Thus, although Torpedo DAG-125 has amino acid sequence that more closely resemble that of human biglycan, based on the similarity of structure and function between biglycan and decorin, the latter proteoglycan and derivatives thereof may also be used to practice the methods herein.

Nucleotide and amino acid sequences of biglycan and decorin genes and proteins from various species are publically available, such as in GenBank. For example, human biglycan can be found under GenBank Accession No. J04599 (human hPGI encoding bone small proteoglycan I (biglycan), described in Fisher et al. (1989) J. Biol. Chem. 264: 4571; SEQ ID Nos: 7-9) and M65154; cow biglycan can be found under GenBank Accession No. L07953; rat biglycan can be found under GenBank Accession No. U17834, mouse biglycan can be found under GenBank Accession No. L20276 and X53928; ovis biglycan can be found under GenBank Accession No. AF034842; human decorin can be found at GenBank Accession No. M14219; rabbit decorin can be found at GenBank Accession No. 147020; chick decorin can be found at GenBank Accession No. P28675; Equus decorin can be found at GenBank Accession No. AF038; bovine decorin can be found at GenBank Accession No. P21793; ovis decorin can be found at GenBank Accession No. AF125041; and rat decorin can be found at GenBank Accession No. Q01129. Sequences of biglycan and decorin and other SLRPs can be found in GenBank.

Decorin and biglycan have one and two glycosaminoglycan (GAG) chains, respectively. Their composition is tissue specific and can be regulated at a number of levels (Hocking et al., (1998) *Matrix Biol* 17: 1-19). For example, the biglycan GAG from skin and cartilage is predominantly dermatan sulfate, while biglycan synthesized in bone is a chondroitin sulfate proteoglycan. Heparan sulfate side chains have not been reported. Both the protein core and the cell type contribute to the distinct glycosylation of these SLRPs.

In certain specific embodiments, biglycan therapeutics include fusion proteins. For example, a biglycan polypeptide or a portion thereof can be fused to an immunoglobulin portion. Alternatively, the fusion protein may be a combination between two or more portions of proteoglycans, e.g., a portion of a biglycan molecule fused to a portion of a decorin molecule.

In certain specific embodiments, biglycan therapeutics include portions and fragments of biglycan. A portion is typically at least 5, 10, 15, or 20 amino acids long. Preferred portions are sufficient for exerting a biological activity, such as interacting with a DAPC component. Portions can comprise or consist of one or more specific domain of a protein. Domains of biglycan and decorin include two cysteine-rich regions (included in the N- and C-terminal 40-50 amino acids of mature biglycan) and leucine-rich repeats (LRRs). The "LRR region" refers to the region of biglycan containing the repeats, and consists essentially of amino acids 81-314. Each individual repeat is referred to herein as an "LRR." LRRs are believed to mediate protein:protein interactions and may thus be sufficient for stabilzing DAPCs and postsynaptic membranes. Based at least on the observation that biglycan binds to MuSK, it is believed that the LRRs are involved in mediating the interaction of biglycan with MuSK and may be involved in mediating MuSK phosphorylation.

In specific embodiments, the present disclosure provides a biglycan therapeutic which consists of a portion of biglycan that is capable of binding to a sarcoglycan. It has been shown that the α-sarcoglycan binding domain of human biglycan is located in the N-terminal domain of the mature biglycan protein, i.e., amino acids 38-80, and more specifically, amino acids 38-58 of SEQ ID NO: 9. It has also been shown that the C-terminal cysteine-rich domain mediates interaction with γ-sarcoglycan. Accordingly, a biglycan therapeutic may include portions (fragments) of biglycan consisting of the N-terminal or the C-terminal cysteine-rich domain, i.e., amino acids 38-80 and 315-368 of SEQ ID NO: 9. Combinations of certain domains of biglycan are also disclosed herein. For example, fragments of biglycan may consist of at least about 20, 30, 40, 50, 60, 70, 80, 90, 100, 150, or 200 amino acids. Short portions of biglycan therapeutics are termed "mini-biglycan therapeutics."

Wild-type human biglycan consists of 368 amino acids (SEQ ID NO: 9), of which amino acids 1-19 constitute a signal peptide (GenBank Accession No. NP_001702 and Fisher et al., supra). Thus wild-type human biglycan without a signal peptide consists of amino acids 20-368 of SEQ ID NO: 9. The mature biglycan protein consists of amino acids 38-368 of SEQ ID NO: 9, since amino acids 1-37, being a pre-propeptide, are cleaved during processing. Amino acids 38-80 correspond to the N-terminal cysteine-rich region. About amino acids 81-314 corresponds to the leucine rich repeat region, containing 10 repeats of about 24 or 23 amino acids. The open reading frame in the cDNA encoding human biglycan corresponds to nucleotides 121-1227 of SEQ ID NO: 7 and is represented as SEQ ID NO: 8. The nucleotide sequence encoding a mature form of biglycan consists in nucleotides 232-1227 of SEQ ID NO: 7.

The biglycan therapeutic can be related to a mature form of the biglycan core, i.e., deprived of the signal peptide, or the full length biglycan with the signal peptide, provided that the two glycanated serines of the biglycan core are deleted or replaced by other amino acids as described herein.

Methods for determining whether a compound has a biological activity of a wild-type biglycan protein are known in the art. A biological activity of a wild-type biglycan protein is intended to refer to one or more of: the ability to promote localization of utrophin to the cell membrane; the ability to maintain the integrity of a plasma membrane; the ability to stabilize DAPCs on plasma membranes; the ability to bind to one or more components of DAPCs; e.g., binding to α-dystroglycan, binding to a sarcoglycan component, such as α-sarcoglycan; phosphorylation of α-sarcoglycan; binding to MuSK; binding to collagen VI stimulating the formation of neuromuscular junctions, such as by stimulating postsynaptic differentiation; stimulating AChR aggregation; stimulation of MuSK phosphorylation and potentiation of agrin-induced MuSK phosphorylation. Such methods can further be adapted for screening libraries of compounds for identifying compounds having one or more of the above-described activities.

Breakdown of cytoplasmic membranes, e.g., the presence of "leaky membranes" can be determined by assays which measure the release of creatine kinase or the absorption of Evans Blue dye, as described, e.g., in Tinsley et al. (1996) *Nature* 384: 349 and Straub et al. (1997) *J. Cell Biol.* 139: 375).

The biglycan therapeutics can also be tested in a variety of animal models, in particular the mdx mice, which are dystrophin negative (see, e.g., U.S. Pat. No. 7,612,038).

Preferred biglycan therapeutics are encoded by nucleotide sequences which are at least about 70%, preferably at least about 80%, even more preferably at least about 85%, at least about 90%, at least about 95%, at least about 98%, or even more preferably at least about 99% identical to the nucleotide sequence of an SLRP, e.g., biglycan, or ortholog thereof, or portion thereof.

Preferred nucleic acids disclosed herein include those encoding a polypeptide comprising an amino acid sequence which is at least about 70%, preferably at least about 80%, even more preferably at least about 85%, at least about 90%, at least about 95%, at least about 98%, and even more preferably at least about 99% identical to the nucleotide sequence of an SLRP, e.g., biglycan (e.g., SEQ ID NO: 7 or 8 encoding human biglycan) or DAG-125 or ortholog thereof, portion thereof, provided that the two glycanated serines of the biglycan core are deleted or replaced by other amino acids as described herein. In one embodiment, the nucleic acid encodes a polypeptide containing one or more of SEQ ID NOs: 1-3 or SEQ ID NOs: 4-6 or 9.

Another aspect of the present disclosure provides a nucleic acid which hybridizes under stringent conditions to a nucleic acid encoding a biglycan therapeutic, e.g., a polypeptide having one or more of SEQ ID NOS: 1 to 6 or 9, or complement thereof. Appropriate stringency conditions which promote DNA hybridization, for example, 6.0× sodium chloride/sodium citrate (SSC) at about 45° C., followed by a wash of 2.0×SSC at 50° C., are known to those skilled in the art or can be found in Current Protocols in Molecular Biology, John Wiley & Sons, N.Y. (1989), 6.3.1-6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature of salt concentration may be held constant while the other variable is changed. In preferred embodiments, a nucleic acid encoding a biglycan polypeptide will bind to a nucleic acid encoding one of SEQ ID NOS 1 to 6 or complement thereof or nucleic acid encoding a SLRP under moderately stringent conditions, for example at about 2.0×SSC and about 40° C. In a particularly preferred embodiment, a nucleic acid according to the present disclosure will hybridize to a nucleotide sequence encoding one of SEQ ID NOS: 1 to 6 or 9, such as a nucleic acid having SEQ ID NO: 7 or 8, or a complement thereof under high stringency conditions.

Various methods for preparing the polypeptides and nucleic acids disclosed herein are well known in the art. For instance, the polypeptide or nucleic acid can be isolated from a tissue or the compound can be recombinantly or synthetically produced. The proteins isolated from tissue are preferably at least about 70%, preferably at least about 80%, at least about 85%, at least about 90%, at least about 95%, at least about 98% and most preferably, at least about 99% pure. Accordingly, preferred polypeptides may contain less than about 1%, and even more preferably less than about 0.1% of material from which the polypeptide was extracted.

The biglycan therapeutic polypeptide can also be produced recombinantly. Typically, a gene encoding the protein is inserted into a plasmid or vector, and the resulting construct is then transfected into appropriate cells, in which the protein is then expressed, and from which the protein is ultimately purified. Methods of producing and purifying biglycans are discussed in Mercado et al. ("Biglycan regulates the expression and sarcolemmal localization of dystrobrevin, syntrophin, and nNOS." Faseb J. 2006). Biglycan polypeptides may also be purified according to the method of Example 12. In some embodiments, the method of Example 12 is combined with further purification steps. These steps may utilize, for example, ion exchange resins.

Accordingly, the present disclosure further pertains to methods of producing the disclosed proteins. For example, a host cell transfected with an expression vector encoding a protein of interest can be cultured under appropriate conditions to allow expression of the protein to occur. The protein may be secreted, by inclusion of a secretion signal sequence, and isolated from a mixture of cells and medium containing the protein. Alternatively, the protein may be retained cytoplasmically and the cells harvested, lysed and the protein isolated. A cell culture includes host cells, media and (typically) cell byproducts. Suitable media for cell culture are well known in the art. The proteins can be isolated from cell culture medium, host cells, or both. Techniques are known in the art for purifying proteins, including ion-exchange chromatography, gel filtration chromatography, ultrafiltration, electrophoresis, and immunoaffinity purification with antibodies specific for particular epitopes of the protein.

Thus, a coding sequence for a biglycan therapeutic polypeptide can be used to produce a recombinant form of the protein via microbial or eukaryotic cellular processes. Ligating the polynucleotide sequence into a gene construct, such as an expression vector, and transforming or transfecting into hosts, either eukaryotic (yeast, avian, insect or mammalian) or prokaryotic (bacterial cells), are standard procedures.

Expression vehicles for production of a recombinant protein include plasmids and other vectors. For instance, suitable vectors for the expression of the instant fusion proteins include plasmids of the types: pBR322-derived plasmids, pEMBL-derived plasmids, pEX-derived plasmids, pBTac-derived plasmids and pUC-derived plasmids for expression in prokaryotic cells, such as *E. coli*.

A number of vectors exist for the expression of recombinant proteins in yeast. For instance, YEP24, YIPS, YEP51, YEP52, pYES2, and YRP17 are cloning and expression vehicles useful in the introduction of genetic constructs into *S. cerevisiae* (see, for example, Broach et al., (1983) in Experimental Manipulation of Gene Expression, ed. M. Inouye Academic Press, p. 83, incorporated by reference herein). These vectors can replicate in *E. coli* due the presence of the pBR322 ori, and in *S. cerevisiae* due to the replication determinant of the yeast 2 micron plasmid. In addition, drug resistance markers such as ampicillin can be used.

The protein can be produced either in eukaryotic cells, e.g., mammalian cells, yeast cells, insect cell (baculovirus system) or in prokaryotic cells.

Cells that can be used for producing a biglycan therapeutic can further be modified to increase the level and/or activity of an enzyme that catalyzes posttranslational modifications, e.g., glycosylations or sulfonations. For example, a cell can be transformed or cotransfected with an expression construct encoding a sulfotransferase, e.g., a chondroitin sulfotransferase, e.g., a chondroitin-6-sulfotransferase (C6ST; Fukuta et al. (1995) *J. Biol. Chem.* 270: 18575), or a nervous system involved sulfotransferase (NSIST), described in Nastuk et al. (1998) *J. Neuroscience* 18: 7167.

In a preferred embodiment, a recombinant protein as described herein, such as biglycan or utrophin, is produced as epitope-tagged, which facilitates co-immunoprecipitation and binding studies. For example, a protein as described herein can be produced in a eukaryotic cell using the vaccinia virus/T7 bacteriophage expression system. A recombinant vaccinia virus, vBGN4 encoding the biglycan polypeptide, e.g., a mature biglycan protein, can be expressed as a polyhistidine fusion protein under control of the T7 phage promoter and expressed, e.g., in HT-1080 cells and UMR106 cells, as described in Hocking et al. (1996) *J Biol Chem* 271: 19571-7.

Immortalized cell lines, e.g., muscle cell lines, such as biglycan negative cell lines, can be obtained as described in Jat et al., *PNAS* (1991) 88: 5096-100; Noble et al., (1992) *Brain Pathology* 2: 39-46. In one embodiment, a H-2K$^b$/tsA58 transgenic mouse is used. This mouse is a heterozygote harboring a thermolabile immortalizing gene (the tsA58 mutant of SV40 large T antigen) under the control of an interferon-inducible promoter (this mouse is available at Charles River). When cells containing this gene are cultured, they proliferate indefinitely at 33° C. in the presence of interferon. However, when the temperature is raised to 39° C. (at which temperature the tsA58 antigen is non-functional) and interferon is removed, the cells cease dividing.

This method has been used for growing a wide variety of cell types, including astrocytes, osteoclasts, trabecular network, and colon epithelial cells (Chambers et al., (1993) *PNAS* 90: 5578-82; Groves et al., (1993) *Dev. Biol.* 159: 87-104; Whitehead et al., (1993) *PNAS* 90: 587-91; Noble et al., (1995) *Transgenic Res.* 4: 215-25; Tamm et al., (1999) *Invest. Ophtamol. Vis. Sci.* 40: 1392-403. This technique is well suited for the production of muscle cell lines. For example, in one study alone, 65 separate muscle cell lines were derived from animals ranging in age from neonates to four weeks (Morgan et al., (1994) *Dev. Biol.* 162 486-98). These lines were maintained for upwards of 80 generations. Remarkably, they not only formed myotubes when shifted to non-permissive conditions in culture, but also formed muscle when implanted into host mice. The H-2K$^b$/tsA58 transgenic method was also used by D. Glass and colleagues to produce a MuSK$^{-/-}$ muscle cell line (Sugiyama et al., (1997) *J. Cell Biol.* 139: 181-91).

To produce conditionally immortalized cell lines, mice having a specific mutation, e.g., a deficiency in biglycan or MuSK, can be crossed with heterozygote H-2K$^b$/tsA58 transgenic mice. The crosses are straightforward since only one copy of the gene is required for full activity. Muscle cells from neonatal animals can then be plated out and grown under permissive conditions (33° C. with interferon). Proliferating cells can then be cloned and samples from each line shifted to the non-permissive temperature and tested for their ability to form myotubes. Wild type; decorin$^{-/-}$; biglycan$^{-/o}$; and decorin$^{-/-}$ biglycan$^{-/o}$ cell lines are examples of cell lines which can be obtained using this technique.

Certain methods for treating subjects with a biglycan therapeutic comprise the administration of the proteins described herein to the subject. However, the proteins can also be produced in a subject, by gene therapy techniques. Thus, for example, a subject can receive an injection in a muscle (e.g., where the subject has a muscle dystrophy) of a vector encoding a biglycan therapeutic protein, such that the vector is capable of entering muscle cells and being expressed therein. Alternatively, the vector can be a viral vector, which is provided with the viral capside and the virus infects the cells, e.g., muscle cells, and thereby deliver the vector. Methods and vectors for gene therapy are well known in the art. Illustrative methods are set forth below.

Preferred mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. Examples of other viral (including retroviral) expression systems can be found below in the description of gene therapy delivery systems. The various methods employed in the preparation of the plasmids and transformation of host organisms are well known in the art. For other suitable expression systems for both prokaryotic and eukaryotic cells, as well as general recombinant procedures, see Molecular Cloning: A Laboratory Manual, 2nd Ed., ed. by Sambrook, Fritsch and Maniatis (Cold Spring Harbor Laboratory Press, 1989) Chapters 16 and 17. In some instances, it may be desirable to express the recombinant fusion proteins by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

In yet other embodiments, the subject expression constructs are derived by insertion of the subject gene into viral vectors including recombinant retroviruses, adenovirus, adeno-associated virus, and herpes simplex virus-1, or recombinant bacterial or eukaryotic plasmids. As described in greater detail below, such embodiments of the subject expression constructs are specifically contemplated for use in various in vivo and ex vivo gene therapy protocols.

Retrovirus vectors and adeno-associated virus vectors are generally understood to be the recombinant gene delivery system of choice for the transfer of exogenous genes in vivo, particularly into humans. These vectors provide efficient delivery of genes into cells, and the transferred nucleic acids are stably integrated into the chromosomal DNA of the host. A major prerequisite for the use of retroviruses is to ensure the safety of their use, particularly with regard to the possibility of the spread of wild-type virus in the cell population. The development of specialized cell lines (termed "packaging cells") which produce only replication-defective retroviruses has increased the utility of retroviruses for gene therapy, and defective retroviruses are well characterized for use in gene transfer for gene therapy purposes (for a review see Miller, A. D. (1990) Blood 76:271). Thus, recombinant retrovirus can be constructed in which part of the retroviral coding sequence (gag, pol, env) has been replaced by nucleic acid encoding a biglycan protein, rendering the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in Current Protocols in Molecular Biology, Ausubel, F. M. et al., (eds.) Greene Publishing Associates, (1989), Sections 9.10-9.14 and other standard laboratory manuals. Examples of suitable retroviruses include pLJ, pZIP, pWE and pEM which are well known to those skilled in the art. Examples of suitable packaging virus lines for preparing both ecotropic and amphotropic retroviral systems include CRIP, Cre, ψ2 and Am. Retroviruses have been used to introduce a variety of genes into many different cell types, including neural cells, epithelial cells, endothelial cells, lymphocytes, myoblasts, hepatocytes, bone marrow cells, in vitro and/or in vivo (see for example Eglitis et al., (1985) Science 230:1395-1398; Danos and Mulligan, (1988) PNAS USA 85:6460-6464; Wilson et al., (1988) PNAS USA 85:3014-3018; Armentano et al., (1990) PNAS USA 87:6141-6145; Huber et al., (1991) PNAS USA 88:8039-8043; Ferry et al., (1991) PNAS USA 88:8377-8381; Chowdhury et al., (1991) Science 254:1802-1805; van Beusechem et al., (1992) PNAS USA 89:7640-7644; Kay et al., (1992) Human Gene Therapy 3:641-647; Dai et al., (1992) PNAS USA 89:10892-10895; Hwu et al., (1993) J. Immunol. 150:4104-4115; U.S. Pat. No. 4,868,116; U.S. Pat. No. 4,980,286; PCT Application WO 89/07136; PCT Application WO 89/02468; PCT Application WO 89/05345; and PCT Application WO 92/07573).

Furthermore, it has been shown that it is possible to limit the infection spectrum of retroviruses and consequently of retroviral-based vectors, by modifying the viral packaging proteins on the surface of the viral particle (see, for example PCT publications WO93/25234, WO94/06920, and WO94/11524). For instance, strategies for the modification of the infection spectrum of retroviral vectors include: coupling antibodies specific for cell surface antigens to the viral env protein (Roux et al., (1989) PNAS USA 86:9079-9083; Julan et al., (1992) J. Gen Virol 73:3251-3255; and Goud et al., (1983) Virology 163:251-254); or coupling cell surface ligands to the viral env proteins (Neda et al., (1991) J. Biol. Chem. 266:14143-14146). Coupling can be in the form of the chemical cross-linking with a protein or other variety (e.g., lactose to convert the env protein to an asialoglycoprotein), as well as by generating fusion proteins (e.g., single-chain antibody/env fusion proteins). This technique, while useful to limit or otherwise direct the infection to certain tissue types, and can also be used to convert an ecotropic vector in to an amphotropic vector.

Another viral gene delivery system utilizes adenovirus-derived vectors. The genome of an adenovirus can be manipulated such that it encodes a gene product of interest, but is inactivate in terms of its ability to replicate in a normal lytic viral life cycle (see, for example, Berkner et al., (1988) BioTechniques 6:616; Rosenfeld et al., (1991) Science 252:431-434; and Rosenfeld et al., (1992) Cell 68:143-155). Suitable adenoviral vectors derived from the adenovirus strain Ad type 5 dl324 or other strains of adenovirus (e.g., Ad2, Ad3, Ad7 etc.) are well known to those skilled in the art. Recombinant adenoviruses can be advantageous in certain circumstances in that they are not capable of infecting nondividing cells and can be used to infect a wide variety of cell types, including airway epithelium (Rosenfeld et al., (1992) cited supra), endothelial cells (Lemarchand et al., (1992) PNAS USA 89:6482-6486), hepatocytes (Herz and Gerard, (1993) PNAS USA 90:2812-2816) and muscle cells (Quantin et al., (1992) PNAS USA 89:2581-2584). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al., supra; Haj-Ahmand and Graham (1986) J. Virol. 57:267). Most replication-defective adenoviral vectors currently in use and therefore favored for use in the methods described herein are deleted for all or parts of the viral E1 and E3 genes but retain as much as 80% of the adenoviral genetic material (see, e.g., Jones et al., (1979) Cell 16:683; Berkner et al., supra; and Graham et al., in Methods in Molecular Biology, E. J. Murray, Ed. (Humana, Clifton, N.J., 1991) vol. 7. pp. 109-127). Expression of the inserted chimeric gene can be under control of, for example, the E1A promoter, the major late promoter (MLP) and associated leader sequences, the viral E3 promoter, or exogenously added promoter sequences.

Yet another viral vector system useful for delivery of the genes disclosed herein is the adeno-associated virus (AAV). Adeno-associated virus is a naturally occurring defective virus that requires another virus, such as an adenovirus or a herpes virus, as a helper virus for efficient replication and a productive life cycle. (For a review, see Muzyczka et al., Curr. Topics in Micro. and Immunol. (1992) 158:97-129). It is also one of the few viruses that may integrate its DNA into non-dividing cells, and exhibits a high frequency of stable integration (see for example Flotte et al., (1992) Am. J. Respir. Cell. Mol. Biol. 7:349-356; Samulski et al., (1989) J. Virol. 63:3822-3828; and McLaughlin et al., (1989) J. Virol. 62:1963-1973). Vectors containing as little as 300 base pairs of AAV can be packaged and can integrate. Space for exogenous DNA is limited to about 4.5 kb. An AAV vector such as that described in Tratschin et al., (1985) Mol. Cell. Biol. 5:3251-3260 can be used to introduce DNA into cells. A variety of nucleic acids have been introduced into different cell types using AAV vectors (see for example Hermonat et al., (1984) PNAS USA 81:6466-6470; Tratschin et al., (1985) Mol. Cell. Biol. 4:2072-2081; Wondisford et al., (1988) Mol. Endocrinol. 2:32-39; Tratschin et al., (1984) J. Virol. 51:611-619; and Flotte et al., (1993) J. Biol. Chem. 268:3781-3790).

Other viral vector systems that may have application in gene therapy have been derived from herpes virus, vaccinia virus, and several RNA viruses. In particular, herpes virus vectors may provide a unique strategy for persistence of the recombinant gene in cells of the central nervous system and ocular tissue (Pepose et al., (1994) Invest Ophthalmol V is Sci 35:2662-2666).

In addition to viral transfer methods, such as those illustrated above, non-viral methods can also be employed to cause expression of a biglycan therapeutic protein in the tissue of an animal. Most nonviral methods of gene transfer rely on normal mechanisms used by mammalian cells for the uptake and intracellular transport of macromolecules. In certain embodiments, non-viral gene delivery systems rely on endocytic pathways for the uptake of the gene by the targeted cell. Exemplary gene delivery systems of this type include liposomal derived systems, poly-lysine conjugates, and artificial viral envelopes.

In a representative embodiment, a gene encoding a protein of interest can be entrapped in liposomes bearing positive charges on their surface (e.g., lipofectins) and (optionally) which are tagged with antibodies against cell surface antigens of the target tissue (Mizuno et al., (1992) No Shinkei Geka 20:547-551; PCT publication WO91/06309; Japanese patent application 1047381; and European patent publication EP-A-43075). For example, lipofection of muscle, neural or cardiac cells can be carried out using liposomes tagged with monoclonal antibodies against specific tissue-associated antigens (Mizuno et al., (1992) Neurol. Med. Chir. 32:873-876).

In yet another illustrative embodiment, the gene delivery system comprises an antibody or cell surface ligand which is cross-linked with a gene binding agent such as poly-lysine (see, for example, PCT publications WO93/04701, WO92/22635, WO92/20316, WO92/19749, and WO92/06180). For example, any of the subject gene constructs can be used to transfect specific cells in vivo using a soluble polynucleotide carrier comprising an antibody conjugated to a polycation, e.g., poly-lysine (see U.S. Pat. No. 5,166,320). It will also be appreciated that effective delivery of the subject nucleic acid constructs via endocytosis can be improved using agents which enhance escape of the gene from the endosomal structures. For instance, whole adenovirus or fusogenic peptides of the influenza HA gene product can be used as part of the delivery system to induce efficient disruption of DNA-containing endosomes (Mulligan et al., (1993) Science 260-926; Wagner et al., (1992) PNAS USA 89:7934; and Christiano et al., (1993) PNAS USA 90:2122).

Nucleic acids encoding biglycan polypeptide can also be administered to a subject as "naked" DNA, as described, e.g., in U.S. Pat. No. 5,679,647 and related patents by Carson et al., in WO 90/11092 and Felgner et al. (1990) Science 247: 1465.

In clinical settings, the gene delivery systems can be introduced into a patient by any of a number of methods. For instance, a pharmaceutical preparation of the gene delivery system can be introduced systemically, e.g., by intravenous injection, and specific transduction of the construct in the target cells occurs predominantly from specificity of transfection provided by the gene delivery vehicle, cell-type or tissue-type expression due to the transcriptional regulatory sequences controlling expression of the gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g. Chen et al., (1994) PNAS USA 91: 3054-3057).

The gene encoding the biglycan therapeutic peptide can be under the control of a constitutive or inducible promoter. These are well known in the art.

IV. Utrophin Proteins and Transcripts

Utrophin is a dystrophin homolog expressed at high levels in developing muscle. It localizes near the neuromuscular junction in adult muscle, though in the absence of dystrophin (i.e., in Duchenne muscular dystrophy), utrophin is also located on the cytoplasmic face of the sarcolemma. Transgenic overexpression of utrophin rescues dystrophic pathology and restores function in the dystrophin-deficient mdx mouse (5-7). In mature muscle, utrophin expression is restricted to the neuromuscular and myotendinous junctions. However, utrophin is expressed over the entire myofiber in developing and regenerating muscle (8-10).

Human utrophin is a protein of 3433 amino acids with a highly conserved C-terminal cysteine-rich region. Utrophin contains a WW domain, EF hand and ZZ domains (Hnia K et al. "ZZ domain of dystrophin and utrophin: topology and mapping of a beta-dystroglycan interaction site" Biochem J. 2007 Feb. 1; 401(3):667-77). The WW domain is a protein-protein interaction domain containing two conserved tryptophan residues. The ZZ domain comprises a predicted zinc finger motif.

In some embodiments, the utrophin polypeptide is human utrophin. In some embodiments, the utrophin polypeptide comprises SEQ ID NO: 13 or an active fragment thereof. In some embodiments, the utrophin polypeptide comprises a sequence at least 80%, 90%, 95%, 97%, 99% identity to SEQ ID NO: 13, or an active fragment thereof. In certain embodiments, the utrophin polypeptide has an intact ZZ domain, and intact EF hand domain, and/or an intact WW domain.

A human mRNA sequence of utrophin is provided as SEQ ID NO: 12, and a polypeptide sequence of human utrophin is provided as SEQ ID NO: 13. SEQ ID NOS: 12 and 13 may also be found under GenBank Accession Number X69086.1 (7 Oct. 2008). Human utrophin sequences may also be found under Accession Number CAA48829 (7 Oct. 2008). The genomic DNA sequence encoding human utrophin is also available in a publically accessible database, for instance Entrez Gene on chromosome 6 location 6q24 (locus tag RP11-352E13.1). The utrophin sequences of model organisms may be readily determined by one of skill in the art. Several model organism utrophin sequences are available in publicly accessible databases. For instance, the *Mus musculus* utrophin sequence is available under accession number NP_035812.

One of skill in the art can determine whether a patient has a utrophin deficiency using the disclosures herein in combination with the state of the art. First, utrophin mRNA or protein levels can be determined. For instance, utrophin mRNA levels can be measured by quantitative reverse transcriptase-PCR, microarray, dot blot, or Southern blot. The utrophin mRNA sequence is provided herein as SEQ ID NO: 12, and one of skill in the art can readily design primers or probes to this sequence. In addition, utrophin protein levels can be measured by Western blot, ELISA, or protein microarray. Utrophin antibodies are available, for instance as described in Mercado M L, et al. (2006) "Biglycan regulates the expression and sarcolemmal localization of dystrobrevin, syntrophin, and nNOS" FASEB. Other utrophin antibodies may be made, and numerous techniques for making antibodies are known in the art. Methods of determining the levels of utrophin mRNA and protein are discussed in Example 4.

In addition, one can determine the DNA sequence of the utrophin gene in a patient to identify mutations. For instance, one can use Sanger sequencing, dye-terminator methods, various high throughput sequencing techniques such as massively parallel signature sequencing, 454 pyrosequencing, Illumina (Solexa) sequencing, and SOLiD sequencing. One can also assay the DNA sequence by hybridization techniques, for instance using probes that contain known utrophin SNPs, deletions, or insertions. One can also use primer extension approaches using primers that terminate in a known utrophin SNPs, deletions, or insertions.

In some embodiments, the assay for utrophin deficiency includes assaying whether a patient has a specific, previously known lesion in the utrophin locus. An exemplary genetic lesion in the utrophin locus is disclosed in Tabet A C et al. ("Molecular characterization of a de novo 6q24.2q25.3 duplication interrupting UTRN in a patient with arthrogryposis." Am J Med Genet A. 2010 July; 152A (7):1781-8).

Several assays of utrophin functionality are known. For instance, utrophin may be assayed for binding to dystroglycan. Another utrophin functional assay examines association of utrophin with Na(v)1.5 via syntrophin proteins (Albesa M et al., "Regulation of the cardiac sodium channel Nav1.5 by utrophin in dystrophin-deficient mice." Cardiovasc Res. 2010 Nov. 3. [Epub ahead of print]). In addition, utrophin may be assayed for binding to the cell polarity-regulating kinase, PAR-1b (Yamashita K et al. "The 8th and 9th tandem spectrin-like repeats of utrophin cooperatively form a functional unit to interact with polarity-regulating kinase PAR-1b." Biochem Biophys Res Commun. 2010 Jan. 1; 391(1): 812-7).

VI. Methods of Treatment

The present disclosure provides therapeutic and prophylactic methods of treatment of disorders including muscular, neuromuscular, neurological, and collagen VI-related disorders. Therapeutic methods are intended to eliminate or at least reduce at least one symptom of a disease or disorder, and preferably cure the disease or disorder. Prophylactic methods include those intended to prevent the appearance of a disease or disorder, i.e., a method which is intended to combat the appearance of the disease or disorder.

Wild-type biglycan was shown to bind to α-dystroglycan and to sarocoglycans, and thereby functions as a link between various components of DAPCs. Furthermore, biglycan levels were found to be high in muscle cells of mice lacking dystrophin (mdx mice, which are a model of muscular dystrophy). Since the absence of dystrophin in muscle cells is known to destabilize the cytoplasmic membrane, the upregulation of biglycan in dystrophin negative muscle cells may be a compensatory mechanism for the absence of dystrophin. Accordingly, in certain embodiments, the present disclosure provides for methods for preventing and treating diseases or disorders that are associated with plasma membrane instability or organization, in particular, an instability resulting from an abnormal DAPC on the plasma membrane. Since the DAPC is found on the membrane of muscle cells, diseases that can be treated using the methods herein include diseases of the muscle, such as muscular dystrophies and muscle atrophy.

In that regard, one promising path for treatment and potentially a cure for muscular dystrophy the activation of an endogenous compensatory mechanism based upon the regulated expression of utrophin. Utrophin is a homolog of dystrophin which shares numerous structural and functional properties with it. However, in both normal and in Duchenne's muscle, utrophin is only expressed at a fraction of the muscle membrane: the neuromuscular junction and the myotendinous junction. The bulk of the membrane has no utrophin. However, in animal models it has been shown that forced expression of utrophin in muscle lacking dystrophin leads to restoration of the DAPC in the muscle membrane and to rescue of the dystrophic phenotype. Since the utrophin gene is often normal in Duchenne patients, a method to activate its expression in muscle and/or to target it to the muscle membrane could serve to restore the DAPC to the membrane and thus promote the health of the muscle cells. Conversely, in patients in which utrophin expression is completely disrupted, biglycan therapy is not predicted to be as effective. However, in patients with abnormally low levels of active utrophin, biglycan therapy can be effective by increasing utrophin levels and/or normalizing its localization. Furthermore, in some embodiments, a test showing that patients have a low level of utrophin indicates that the patient should be treated with a combination of a biglycan therapeutic and a utrophin therapeutic.

Several lines of evidence, many of them arising from observations made by the inventors, indicate that the small leucine-rich repeat proteoglycan biglycan could be used in a method for regulating utrophin expression and localization. It has been demonstrated that the protein agrin can cause an upregulation of utrophin expression and direct it to be localized to specific domains on the cell surface. The signaling receptor for agrin is the receptor tyrosine kinase MuSK. It has been observed that agrin can also induce the tyrosine phosphorylation of α- and γ-sarcoglycan in cultured myotubes. It was also observed that biglycan can also regulate the tyrosine phosphorylation of α- and γ-sarcoglycan. Moreover, the receptor tyrosine kinase MuSK is required for this biglycan-induced tyrosine phosphorylation of these proteins. Further, biglycan can bind to MuSK. These observations indicate that biglycan can act directly to organize the DAPC, including utrophin, on the muscle cell surface.

Thus the present application provides the treatment of these disorders with biglycan therapeutics which upregulate utrophin, normalize utrophin localization, activate MuSK and/or induce phosphorylation of sarcoglycans.

Merely to illustrate, biglycan therapeutics (e.g., polypeptides, peptides or peptidomimetics) can be delivered to patients with muscular dystrophy, a muscle atrophy, or other conditions, to upregulate the endogenous utrophin gene expression and/or to promote the localization of utrophin to the muscle membrane. In such embodiments, the biglycan therapeutic polypeptide may be delivered in the form of a polypeptide in and of itself, or as part of a fusion protein, e.g., fused to a humanized antibody sequence or similar carrier entity. Biglycan therapeutic polypeptides can be delivered by nucleic acid-based methods including as plasmid DNA, in viral vectors, or other modalities where the nucleic acid sequences encoding the biglycan therapeutic polypeptides are introduced into patients. The delivery of a biglycan therapeutic can serve to heal the muscle fibers from within by directing the increased expression and regulated localization of utrophin to the muscle cell surface with concomitant restoration of the remainder of the dystrophin-associated protein complex.

Furthermore, since DAPCs are also found on other cell types, the present disclosure also provides methods for treating diseases associated with any abnormal DAPC. For example, DAPC are present in the brain, and since, in addition, agrin has been found in senile plaques in patients with Alzheimers's disease, neurological diseases can also be treated or prevented according to the methods described herein. A further indication that neurological disorders can be treated or prevented according to the methods described herein is based on the observation that patients with muscular dystrophy often also suffer from peripheral and central nervous system disorder. Accordingly, about one third of patients with Duchenne Muscular Dystrophy have a mental affliction, in particular, mental retardation. Thus, dystrophin, and hence, DAPCs, are believed to play a role in the nervous system.

Patients with Duchenne's Muscular Dystrophy also have diaphragm problems, indicating a role for dystrophin, and possibly DAPCs in diaphragms. Thus, compositions and methods described herein would also find an application in disorders associated with diaphragm abnormalities.

The present application discloses methods to predict a patient's response to biglycan, wherein the patient has one or more of several diseases. Such disease include not only those in which biglycan is abnormal, but more generally any disease or condition that is associated with a defect that can be improved or cured by biglycan. In particular, the diseases may be characterized by a defect or an abnormality in any component of the DAPC or component associated therewith, thereby resulting, e.g., in an unstable plasma membrane, provided that the biglycan therapeutics can at least partially cure the defect resulting from the deficient component. In particular, diseases include any disease associated with an unstable DAPC, which can be rendered more stable by the presence of a biglycan therapeutic.

Furthermore, since biglycan was shown to bind to, and phosphorylates MuSK, a receptor which is known for mediating agrin-induced stimulation of neuromuscular junction formation, in particular postsynaptic membrane differentiation, to potentiate agrin-induced AChR aggregation, and to correct a defective agrin-induced AChR aggregation in myotubes of biglycan negative mice by its addition to the myotubes, the present disclosure also provides methods relating to diseases or disorders of neuromuscular junctions, such as neuromuscular disorders. For instance, these diseases may be treated with one of the biglycan combination therapeutics disclosed herein. In addition, one may determine whether a patient will respond to biglycan therapy for a diseases or disorders of neuromuscular junctions, such as neuromuscular disorders using an assay for utrophin.

A. Exemplary Diseases and Disorders

The compositions and methods herein may be used with a wide variety of biglycan-related disorders. In particular, one can use the methods herein to predict a patient's response to biglycan therapy, wherein the patient has any suitable disease treatable with a biglycan therapy. Numerous examples of such diseases, including muscular dystrophies and motor neuron diseases, are provided herein.

Diseases or disorders that are characterized by a destabilization or improper organization of the plasma membrane of specific cell types include muscular dystrophies (MDs), a group of genetic degenerative myopathies characterized by weakness and muscle atrophy without nervous system involvement. The three main types are pseudohypertrophic (Duchenne, Becker), limb-girdle, and facioscapulohumeral. For example, muscular dystrophies and muscular atrophies are characterized by a breakdown of the muscle cell membrane, i.e., they are characterized by leaky membranes, which are believed to result from a mutation in a component of the DAPC, i.e., dystrophin. Mutations in the sarcoglycans are also known to result in muscular dystrophies and leaky membranes. Accordingly, the present disclosure provides methods for predicting a patient's response to a biglycan therapeutic with respect to diseases associated with mutations in dystrophin and/or in sarcoglycans or other component of DAPCs, in particular muscular dystrophies. The present disclosure also provides methods for using the combination therapeutics herein to treat diseases diseases associated with mutations in dystrophin and/or in sarcoglycans or other component of DAPCs, in particular muscular dystrophies.

Dystrophin abnormalities are responsible for both the milder Becker's Muscular Dystrophy (BMD) and the severe Duchenne's Muscular Dystrophy (DMD). In BMD, dystrophin is made, but it is abnormal in either size and/or amount. The patient is mild to moderately weak. In DMD no protein is made and the patient is wheelchair-bound by age 13 and usually dies by age 20.

Another type of dystrophy includes congenital muscular dystrophy (CMD), a very disabling muscle disease of early clinical onset, is the most frequent cause of severe neonatal hypotonia. Its manifestations are noticed at birth or in the first months of life and consist of muscle hypotonia, often associated with delayed motor milestones, severe and early contractures and joint deformities. Serum creatine kinase is raised, up to 30 times the normal values, in the early stage of the disease, and then rapidly decreases. The histological changes in the muscle biopsies consist of large variation in the size of muscle fibers, a few necrotic and regenerating fibers, marked increase in endomysial collagen tissue, and no specific ultrastructural features. The diagnosis of CMD has been based on the clinical picture and the morphological changes in the muscle biopsy, but it cannot be made with certainty, as other muscle disorders may present with similar clinico-pathological features. Within the group of diseases classified as CMD, various forms have been individualized. The two more common forms are the occidental and the Japanese, the latter being associated with severe mental disturbances, and usually referred to as Fukuyama congenital muscular dystrophy (FCMD).

One form of congenital muscular dystrophy (CMD) has recently been characterized as being caused by mutations in the laminin alpha 2-chain gene. Laminin is a protein that associates with DAPCs. Thus, the present disclosure also provides methods for predicting the effect of biglycan therapy on diseases that are associated with abnormal molecules which normally associate with DAPCs. The present disclosure also provides methods for using the combination therapeutics herein to treat diseases that are associated with abnormal molecules which normally associate with DAPCs.

Other muscular dystrophies include limb-girdle muscular dystrophy (LGMD), which represents a clinically and genetically heterogeneous class of disorders. These dystrophies are inherited as either autosomal dominant or recessive traits. An autosomal dominant form, LGMD1A, was mapped to 5q31-q33 (Speer, M. C. et al., Am. J. Hum. Genet. 50:1211, 1992; Yamaoka, L. Y. et al., Neuromusc. Disord. 4:471, 1994), while six genes involved in the autosomal recessive forms were mapped to 15q15.1 (LGMD2A) (Beckmann, J. S. et al., C. R. Acad. Sci. Paris 312:141, 1991), 2p16-p13 (LGMD2B) (Bashir, R. et al., Hum. Mol. Genet. 3:455, 1994), 13q12 (LGMD2C) (Ben Othmane, K. et al., Nature Genet. 2:315, 1992; Azibi, K. et al., Hum. Mol. Genet. 2:1423, 1993), 17q12-q21.33 (LGMD2D) (Roberds, S. L. et al., Cell 78:625, 1994; McNally, E. M., et. al., Proc. Nat. Acad. Sci. U.S.A. 91:9690, 1994), 4q12 (LG1MD2E) (Lim, L. E., et. al., Nat. Genet. 11:257, 1994; Bonnemann, C. G. et al. Nat. Genet. 11:266, 1995), and most recently to 5q33-q34 (LGMD2F) (Passos-Bueno, M. R., et. al., Hum. Mol. Genet. 5:815, 1996). Patients with LGMD2C, 2D and 2E have a deficiency of components of the sarcoglycan complex resulting from mutations in the genes encoding gamma-, alpha-, and beta-sarcoglycan, respectively. The gene responsible for LGMD2A has been identified as the muscle-specific calpain, whereas the genes responsible for LGMD1A, 2B and 2F are still unknown.

Yet other types of muscular dystrophies include Welander distal myopathy (WDM), which is an autosomal dominant myopathy with late-adult onset characterized by slow progression of distal muscle weakness. The disorder is considered a model disease for hereditary distal myopathies. The disease is linked to chromosome 2p13. Another muscular dystrophy is Miyoshi myopathya, which is a distal muscular dystrophy that is caused by mutations in the recently cloned gene dysferlin, gene symbol DYSF (Weiler et al. (1999) *Hum Mol Genet.* 8: 871-7). Yet other dystrophies include Hereditary Distal Myopathy, Benign Congenital Hypotonia, Central Core disease, Nemaline Myopathy, and Myotubular (centronuclear) myopathy.

Other diseases that can be treated or prevented using biglycan therapeutics include those characterized by tissue atrophy, e.g., muscle atrophy, other than muscle atrophy resulting from muscular dystrophies, provided that the atrophy is stopped or slowed down upon treatment with a biglycan therapeutic. Furthermore, the present disclosure also provides methods for reversing tissue atrophies, e.g., muscle atrophies. This can be achieved, e.g., by treating the patient with a biglycan therapeutic and a utrophin therapeutic, such as by providing to the atrophied tissue a composition comprising a biglycan therapeutic and a utrophin therapeutic, or separate compositions comprising these therapeutics individually.

Muscle atrophies can result from denervation (loss of contact by the muscle with its nerve) due to nerve trauma; degenerative, metabolic or inflammatory neuropathy (e.g., Guillian-Barré syndrome), peripheral neuropathy, or damage to nerves caused by environmental toxins or drugs. In another embodiment, the muscle atrophy results from denervation due to a motor neuronopathy. Such motor neuronopathies include, but are not limited to: adult motor neuron disease, including Amyotrophic Lateral Sclerosis (ALS or Lou Gehrig's disease); infantile and juvenile spinal muscular atrophies, and autoimmune motor neuropathy with multifocal conduction block. In another embodiment, the muscle atrophy results from chronic disuse. Such disuse atrophy may stem from conditions including, but not limited to: paralysis due to stroke, spinal cord injury; skeletal immobilization due to trauma (such as fracture, sprain or dislocation) or prolonged bed rest. In yet another embodiment, the muscle atrophy results from metabolic stress or nutritional insufficiency, including, but not limited to, the cachexia of cancer and other chronic illnesses, fasting or rhabdomyolysis, endocrine disorders such as, but not limited to, disorders of the thyroid gland and diabetes.

Since muscle tissue atrophy and necrosis are often accompanied by fibrosis of the affected tissue, the reversal or the inhibition of atrophy or necrosis can also result in an inhibition or reversal of fibrosis.

In addition, the biglycan therapeutics may be of use in the treatment of acquired (toxic or inflammatory) myopathies. Myopathies which occur as a consequence of an inflammatory disease of muscle, include, but not limited to polymyositis and dermatomyositis. Toxic myopathies may be due to agents, including, but are not limited to adiodarone, chloroquine, clofibrate, colchicine, doxorubicin, ethanol, hydroxychloroquine, organophosphates, perihexyline, and vincristine.

Neuromuscular dystrophies include myotonic dystrophy. Myotonic dystrophy (DM; or Steinert's disease) is an autosomal dominant neuromuscular disease which is the most common form of muscular dystrophy affecting adults. The clinical picture in DM is well established but exceptionally variable (Harper, P. S., Myotonic Dystrophy, 2nd ed., W. B. Saunders Co., London, 1989). Although generally considered a disease of muscle, with myotonia, progressive weakness and wasting, DM is characterized by abnormalities in a variety of other systems. DM patients often suffer from cardiac conduction defects, smooth muscle involvement, hypersomnia, cataracts, abnormal glucose response, and, in males, premature balding and testicular atrophy (Harper, P. S., Myotonic Dystrophy, 2nd ed., W. B. Saunders Co., London, 1989). The mildest form, which is occasionally difficult to diagnose, is seen in middle or old age and is characterized by cataracts with little or no muscle involvement. The classical form, showing myotonia and muscle weakness, most frequently has onset in early adult life and in adolescence. The most severe form, which occurs congenitally, is associated with generalized muscular hypoplasia, mental retardation, and high neonatal mortality. This disease and the gene affected is further described in U.S. Pat. No. 5,955,265.

Another neuromuscular disease is spinal muscular atrophy ("SMA"), which is the second most common neuromuscular disease in children after Duchenne muscular dystrophy. SMA refers to a debilitating neuromuscular disorder which primarily affects infants and young children. This disorder is caused by degeneration of the lower motor neurons, also known as the anterior horn cells of the spinal cord. Normal lower motor neurons stimulate muscles to contract. Neuronal degeneration reduces stimulation which causes muscle tissue to atrophy (see, e.g., U.S. Pat. No. 5,882,868).

The above-described muscular dystrophies and myopathies are skeletal muscle disorders. However, the present disclosure also pertains to disorders of smooth muscles, e.g., cardiac myopathies, including hypertrophic cardiomyopathy, dilated cardiomyopathy and restrictive cardiomyopathy. At least certain smooth muscles, e.g., cardiac muscle, are rich in sarcoglycans. Mutations in sarcoglycans can result in sarcolemmal instability at the myocardial level (see, e.g., Melacini (1999) *Muscle Nerve* 22: 473). For example, animal models in which a sarcoglycan is mutated show cardiac creatine kinase elevation. In particular, it has been shown that delta-sarcoglycan (Sgcd) null mice develop cardiomyopathy with focal areas of necrosis as the histological hallmark in cardiac and skeletal muscle. The animals also showed an absence of the sarcoglycan-sarcospan (SG-SSPN) complex in skeletal and cardiac membranes. Loss of vascular smooth muscle SG-SSPN complex was associated with irregularities of the coronary vasculature. Thus, disruption of the SG-SSPN complex in vascular smooth muscle perturbs vascular function, which initiates cardiomyopathy and exacerbates muscular dystrophy (Coral-Vazquez et al. (1999) *Cell* 98: 465).

Similarly to delta-sarcoglycan negative mice, mice lacking γ-sarcoglycan showed pronounced dystrophic muscle changes in early life (Hack et al. (1998) *J Cell Biol* 142: 1279). By 20 wk of age, these mice developed cardiomyopathy and died prematurely. Furthermore, apoptotic myonuclei were abundant in skeletal muscle lacking γ-sarcoglycan, suggesting that programmed cell death contributes to myofiber degeneration. Vital staining with Evans blue dye revealed that muscle lacking γ-sarcoglycan developed membrane disruptions like those seen in dystrophin-deficient muscle. It was also shown that the loss of γ-sarcoglycan produced secondary reduction of beta- and delta-sarcoglycan with partial retention of α- and ε-sarcoglycan, indicating that β-, γ-, and δ-sarcoglycan function as a unit. Since the other components of the cytoplasmic membrane complex were functional, the complex could be stabilized by the presence of a biglycan therapeutic.

In addition to animal models, certain cardiomyopathies in humans have been linked to mutations in dystrophin, dystroglycans or sarcoglycans. For example, dystrophin has been identified as the gene responsible for X-linked dilated cardiomyopathy (Towbin J. A. (1998) *Curr Opin Cell Biol* 10: 131, and references therein). In this case, the dystrophin gene contained a 5'-mutation which results in cardiomyopathy without clinically-apparent skeletal myopathy (Bies et al. (1997) *J Mol Cell Cardiol* 29: 3175.

Furthermore, cardiomyopathy was also found in subjects having Duchenne's Muscular Dystrophy (associated with a mutated dystrophin), or other types of muscular dystrophies, such as Limb Girdle Muscular Dystrophy. For example, dilated cardiomyopathy was present in one autosomal dominant case and in three advanced autosomal recessive or sporadic patients, of whom two were found to have α-sarcoglycan deficiency. Two of these three patients and three other cases showed ECG abnormalities known to be characteristic of the dystrophinopathies. A strong association between the absence of alpha sarcoglycan and the presence of dilated cardiomyopathy was found. In six autosomal dominant cases, there were atrioventricular (AV) conduction disturbances, increasing in severity with age and in concomitant presence of muscle weakness. Pacemaker implantation was necessary in certain of these patients (see van der Kooi (1998) *Heart* 79: 73).

Biglycan therapeutics can also be used to treat or prevent cardiomyopathy, e.g., dilated cardiomyopathy, of viral origin, e.g., resulting from an enterovirus infection, e.g., a Coxsackievirus B3. It has been shown that purified Coxsackievirus protease 2A cleaves dystrophin in vitro and during Coxsackievirus infection of cultured myocytes and in infected mouse hearts, leading to impaired dystrophin function (Badorff et al. (1999) *Nat Med* 5: 320. Cleavage of dystrophin results in disruption of the dystrophin-associated glycoproteins α-sarcoglycan and β-dystroglycan. Thus, cardiomyopathy could be prevented or reversed by administration of a biglycan therapeutic to a subject having been infected with a virus causing cardiomyopathy, e.g., by disruption of dystrophin or a protein associated therewith. Administration of a combination biglycan and utrophin therapeutic could restabilize or reorganize the cytoplasmic membrane of affected cardiac cells.

In some embodiments, the biglycan therapeutics can be used to treat myasthenia gravis, a neuromuscular disorder.

Thus, biglycan therapeutics can also be used to prevent or to treat smooth muscle disorders, such as cardiac myopathies, and to stop atrophy and/or necrosis of cardiac smooth muscle tissue. The treatment can also be used to promote survival of myocytes. Thus, the methods herein may be used to predict a patient's response to biglycan therapy with respect to smooth muscle and cardiac muscle disorders.

Neurological disorders that can be treated with a biglycan therapeutic include polymyositis, and neurogenic disorders. Another neurological disease that can be treated is Alzheimers' disease.

Other diseases that can be treated according to the methods herein include those in which a proteoglycan is present at abnormal levels, or has an abnormal activity, relative to that in normal subjects. For example, a disease or disorder could be caused by a lower level of biglycan, resulting in, e.g., unstable cytoplasmic membranes. Alternatively, a disease or disorder could result from an abnormally high level or activity of biglycan, resulting in, e.g., overstimulation of MuSK or over-aggregation of AChRs (see below).

Yet other diseases or disorders that may be treated or evaluated for biglycan-responsiveness with the methods herein include those that are associated with an abnormal interaction between a proteoglycan and another molecule (other than those of the DAPC or MuSK), e.g., a complement factor, such as C1q. For example, it has been shown that C1q interacts with biglycan (Hocking et al. (1996) *J. Biol. Chem.* 271: 19571). It is also known that binding of C1q to cell surfaces mediates a number of biological activities including enhancement of phagocytosis and stimulation of superoxide production. Thus, since biglycan binds to C1q, a biglycan therapeutic may be used to inhibit the binding of C1q to its receptor on cell surfaces to inhibit one or more of such biological activities. In addition, a biglycan therapeutic which inhibits the interaction between C1q or other complement component and a cell surface can also be used to inhibit complement mediated necrosis of the cells and tissues containing such cells.

Furthermore, this application provides methods for preventing or inhibiting infections of cells by microorganisms, e.g., viruses. For example, it has been shown that dystroglycan is a receptor via which certain microorganisms enter eukaryotic cells (*Science* (1998) 282: 2079). Thus, by administrating to a subject a compound which, directly or indirectly, causes the site on dystroglycan molecules to which the microorganism binds to be unavailable, entering of the microorganism into the cell can be inhibited. This method can be used, e.g., to prevent or inhibit Lassa Fever virus and lymphocytic choriomeningitis virus (LCMV) infection, as well as infection by other arenaviruses, including Oliveros and Mobala. Soluble α-dystroglycan was shown to block both LCMV and LFV infection (*Science* (1998) 282: 2079). Thus, the biglycan combination therapeutics disclosed herein may be used to treat biglycan-related infectious diseases.

In addition to cell cultures, e.g., established from patients having, e.g., a muscular dystrophy, various animal models can be used to select the most appropriate biglycan therapeutic for treating a disease. In particular, to identify a therapeutic for use in preventing or treating a muscular dystrophy or cardiomyopathy associated with a mutated or absent DAPC component or, mice having mutated versions of these proteins, or having null mutations in the genes encoding these proteins, can be used. For example, mice having a disrupted sarcoglycan, such as delta-sarcoglycan, can be used. Such mice are described, e.g., Coral-Vazquez et al. (1999) *Cell* 98: 465. Alternatively, mice deficient in dystrophin (mdx mice), or in α- or γ-sarcoglycans can be used. Such mice have been described herein and in the literature. Additional mice can be made according to known methods in the art. In an illustrative embodiment to identify therapeutics, different therapeutics are administered to δ-sarcoglycan null mice, and the effect of the therapeutics are evaluated by studying cardiac function. Another animal model that can be used for this purpose is the cardiomyopathic hamster that does not express δ-sarcoglycan due to a genomic deletion. This rat is an animal model for autosomal recessive cardiomyopathy, and is further described in Sakamoto et al. *FEBS Lett* 1999 (1999) 44: 124.

Biglycan therapeutics may also be used to treat collagen VI disorders, as discussed in U.S. Pat. No. 7,759,314. In U.S. Pat. No. 7,759,314, it was shown that biglycan null mice exhibited a striking reduction in collagen VI levels, as determined by immunofluorescence. As shown in Example 11, administration of biglycan to a mouse with a collagen VI deficiency resulted in increased levels of collagen VI in muscle. Therefore, the biglycan combination therapeutics described herein may also be used to elevate collagen VI levels, thereby treating collagen VI disorders. Furthermore, one may use the methods herein to predict a patient's response to a biglycan therapy for a collagen VI disorder.

In general, the collagen VI disorder is one in which the subject produces a low, non-zero level or activity of collagen VI. In some embodiments, the disorder is characterized by a mutation that reduces, but does not completely eliminate, collagen VI activity. In some embodiments, the disorder is characterized by a reduction in collagen VI stability. In certain embodiments, the disorder is characterized by low, non-zero levels of collagen VI protein. For example, a heterozygous mutation (e.g., a haploinsufficiency) may result in reduced levels of collagen VI. Administration of a biglycan therapeutic is expected to increase the level of collagen VI, thereby treating the collagen VI disorder.

Thus, specific collagen VI disorders that may be treated according to methods disclosed herein include the following. Bethlem's myopathy is caused, at least in part, by mutations in collagen VI genes. In some embodiments, Bethlem's myopathy is caused by a haploinsufficiency (Pepe G et al., "COL6A1 genomic deletions in Bethlem myopathy and Ullrich muscular dystrophy." Ann Neurol. 2006 January; 59(1):190-5; Baker et al. "Molecular consequences of dominant Bethlem myopathy collagen VI mutations" Ann Neurol. 2007 October; 62(4):390-405). Collagen VI function is also compromised in Ullrich Congenital Muscular Dystrophy. Like Bethlem myopathy, UCMD patients can have a wild-type copy of collagen VI (Jimenez-Mallebrera et al., "A comparative analysis of collagen VI production in muscle, skin and fibroblasts from 14 Ullrich congenital muscular dystrophy patients with dominant and recessive COL6A mutations" Neuromuscul Disord. 2006 October; 16(9-10):571-82). In certain embodiments, a collagen VI-related disorder may be treated by administering a biglycan therapeutic as described herein.

VI. Effective Dose and Administration of Therapeutic Compositions

The above-described diseases or disorders can be treated or ameliorated in a subject by administering to the subject a pharmaceutically effective amount of a biglycan or bigylcan-related therapeutic conjointly with a second therapeutic, such as a utrophin therapeutic. "Conjoint administration", as used herein, refers to a therapeutic regimen in which two agents are administered to a patient such that both agents are present at an effective amount in the tissue being treated at the same time. The two agents may be administered simultaneously (e.g., in the same composition or in separate compositions), or at separate times (in either order), and can even be administered by different modes of administration. For instance, administraion of a biglycan therapeutic may precede or follow administration of the second therapeutic (e.g., a utrophin therapeutic) by intervals ranging from minutes to days. In certain such embodiments, a biglycan therapeutic and a second therapeutic (such as a utrophin therapeutic) may be administered within about 1 minute, about 5 minutes, about 10 minutes, about 30 minutes, about 60 minutes, about 2 hours, about 4 hours, about 6 hours, 8 hours, about 10 hours, about 12 hours, about 18 hours, about 24 hours, about 36 hours, or about 48 hours or more of one another. Because biglycan can be detected in mouse muscle tissue two weeks after administration (see Example 3), in some embodiments biglycan can be administered at least two weeks before a second therapeutic and still be present at an effective level when the second therapeutic is administered. In some embodiments, administration of a biglycan therapeutic and a second therapeutic will be within about 1 minute, about 5 minutes, about 30 minutes, or even about 60 minutes of one another.

In certain embodiments, a biglycan therapeutic and a second therapeutic (such as a utrophin therapeutic) may be administered according to different dosing regimen (e.g., a biglycan therapeutic, for example, is administered only once every 1 to 4 weeks while a second therapeutic is administered daily; alternatively, the biglycan therapeutic may be administered once a day while a second therapeutic may be administered only once every three weeks) such that in some instances administration of a biglycan therapeutic and a second therapeutic will be within about 60 minutes of one another, while in other instances, administration of a biglycan therapeutic and a second therapeutic will be within days of one another.

Depending on whether the disease is caused by higher levels or activity or by lower levels or activity of biglycan, an agonist or an antagonist biglycan therapeutic is administered to a subject having the disease. Although a person of skill in the art will be able to predict which therapeutic to administer for treating any of the diseases herein, tests can be performed to determine the appropriate therapeutic to administer. Such tests can use, for example, animal models of the disease. Alternatively, in cases where diseases are due to a mutation in, for example, biglycan or utrophin, in vitro tests can be undertaken to determine the effect of the mutation. This will allow the determination of what type of therapeutic should be administered to a subject having this type of mutation.

Another manner of administering a biglycan therapeutic to a subject is by preparing cells expressing and secreting the biglycan therapeutic protein of interest, inserting the cells into a matrix and administering this matrix to the subject at the desired location. Thus, cells engineered in accordance with this disclosure may also be encapsulated, e.g., using conventional biocompatible materials and methods, prior to implantation into the host organism or patient for the production of a therapeutic protein. See e.g., Hguyen et al., Tissue Implant Systems and Methods for Sustaining viable High Cell Densities within a Host, U.S. Pat. No. 5,314,471 (Baxter International, Inc.); Uludag and Sefton, 1993, J. Biomed. Mater. Res. 27(10):1213-24 (HepG2 cells/hydroxyethyl methacrylate-methyl methacrylate membranes); Chang et al., 1993, Hum Gene Ther 4(4):433-40 (mouse Ltk– cells expressing hGH/immunoprotective perm-selective alginate microcapsules; Reddy et al., 1993, J Infect Dis 168(4):1082-3 (alginate); Tai and Sun, 1993, FASEB J 7(11):1061-9 (mouse fibroblasts expressing hGH/alginate-poly-L-lysine-alginate membrane); Ao et al., 1995, Transplanataion Proc. 27(6):3349, 3350 (alginate); Rajotte et al., 1995, Transplantation Proc. 27(6):3389 (alginate); Lakey et al., 1995, Transplantation Proc. 27(6):3266 (alginate); Korbutt et al., 1995, Transplantation Proc. 27(6):3212 (alginate); Dorian et al, U.S. Pat. No. 5,429,821 (alginate); Emerich et al., 1993, Exp Neurol 122(1):37-47 (polymer-encapsulated PC12 cells); Sagen et al, 1993, J Neurosci 13(6):2415-23 (bovine chromaffin cells encapsulated in semipermeable polymer membrane and implanted into rat spinal subarachnoid space); Aebischer et al., 1994, Exp Neurol 126(2):151-8 (polymer-encapsulated rat PC12 cells implanted into monkeys; see also Aebischer, WO 92/19595); Savelkoul et al., 1994, J Immunol Methods 170(2):185-96 (encapsulated hybridomas producing antibodies; encapsulated transfected cell lines expressing various cytokines); Winn et al., 1994, PNAS USA 91(6):2324-8 (engineered BHK cells expressing human nerve growth factor encapsulated in an immunoisolation polymeric device and transplanted into rats); Emerich et al., 1994, Prog Neuropsychopharmacol Biol Psychiatry 18(5):935-46 (polymer-encapsulated PC12 cells implanted into rats); Kordower et al., 1994, PNAS USA 91(23):10898-902 (polymer-encapsulated engineered BHK cells expressing hNGF implanted into monkeys) and Butler et al WO 95/04521 (encapsulated device). The cells may then be introduced in encapsulated form into an animal host, preferably a mammal and more preferably a human subject in need thereof. Preferably the encapsulating material is semipermeable, permitting release into the host of secreted proteins produced by the encapsulated cells. In many embodiments the semipermeable encapsulation renders the encapsulated cells immunologically isolated from the host organism in which the encapsulated cells are introduced. In those embodiments, the cells to be encapsulated may express one or more therapeutic proteins of the host species and/or from viral proteins or proteins from species other than the host species.

Alternatively, the biglycan therapeutic is a nucleic acid encoding the biglycan therapeutic protein. Thus, a subject in need thereof may receive a dose of viral vector encoding the protein of interest, which may be specifically targeted to a specific tissue, e.g., a dystrophic tissue. The vector can be administered in naked form, or it can be administered as a viral particle (further described herein). For this purpose, various techniques have been developed for modification of target tissue and cells in vivo. A number of viral vectors have been developed, such as described above, which allow for transfection and, in some cases, integration of the virus into the host. See, for example, Dubensky et al. (1984) Proc. Natl. Acad. Sci. USA 81, 7529-7533; Kaneda et al., (1989) Science 243, 375-378; Hiebert et al. (1989) Proc. Natl. Acad. Sci. USA 86, 3594-3598; Hatzoglu et al. (1990) J. Biol. Chem. 265, 17285-17293 and Ferry, et al. (1991) Proc. Natl. Acad. Sci. USA 88, 8377-8381. The vector may be administered by injection, e.g., intravascularly or intramuscularly, inhalation, or other parenteral mode. Non-viral delivery methods such as administration of the DNA via complexes with liposomes or by injection, catheter or biolistics may also be used.

In yet another embodiment, cells are obtained from a subject, modified ex vivo, and introduced into the same or a different subject. Additional methods of administration of the therapeutic compounds are set forth below.

In certain embodiments, a biglycan therapeutic is administered to a dose equivalent to the 2, 5, and 10 mg/kg doses that were effective in mice (see Examples 13 and 14). One measure for converting an animal dose to a human dose is based on body surface area and is described in Guidance for Industry Reviewers: Estimating the Safe Starting Dose in Clinical Trials for Therapeutics in Adult Healthy Volunteers, on the world wide web at fda.gov/ohrms/dockets/98fr/02d-0492-gd10001-vol1.pdf. This publication recommends dividing a murine dose by 12.3 to arrive at a human dose. Using this conversion factor, human doses corresponding to 2, 5, and 10 mg/kg murine doses are 0.16 mg/kg, 0.41 mg/kg, and 0.81 mg/kg. Thus, in some embodiments, the administered dose of a biglycan polypeptide is between 0.16 and 0.81 mg/kg. In some embodiments, the dose of the biglycan polypeptide is 0.1-1.5 mg/kg, 0.1-1.2 mg/kg, 0.1-1.0 mg/kg, 0.1-0.5 mg/kg, 0.2-1.0 mg/kg, or 0.5-1.5 mg/kg. In preferred embodiments, the dose is 0.1-1.2 mg/kg. These doses may be administered, e.g., every 1-4 weeks, every 1-2 weeks, every 2-3 weeks, or every 3-4 weeks.

A. Toxicity

Example 8 shows rhBRN to have low toxicity in mice. The assay of Example 8 can also be used to determine the toxicity of other biglycan therapeutics. Toxicity and therapeutic efficacy of biglycan therapeutics can be determined by standard pharmaceutical procedures in cell cultures or experimental animals, e.g., for determining the $LD_{50}$ (the dose lethal to 50% of the population of model organisms) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. In particular, where the therapeutic is administered for potentiating AChR aggregation, it is desirable to establish the dose that will result in stimulation, if desired, or inhibition, if desired. Tests can then be continued in medical tests. The dosage of such compounds lies preferably within a range of circulating concentrations that include the $ED_{50}$ with little or no toxicity. The dosage may vary within this range depending upon the dosage form employed and the route of administration utilized. For any compound used in the methods herein, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

B. Pharmaceutical Compositions

Pharmaceutical compositions for use in accordance with the present disclosure may be formulated in conventional manner using one or more physiologically acceptable carriers or excipients. Thus, the therapeutics and their physiologically acceptable salts and solvates may be formulated for administration by, for example, injection, inhalation or insufflation (either through the mouth or the nose) or oral, buccal, parenteral or rectal administration.

For such therapy, the biglycan combination therapeutics can be formulated for a variety of loads of administration, including systemic and topical or localized administration. Techniques and formulations generally may be found in Remmington's Pharmaceutical Sciences, Meade Publishing Co., Easton, Pa. For systemic administration, injection may be used, including intramuscular, intravenous, intraperitoneal, and subcutaneous. For injection, the biglycan therapeutics can be formulated in liquid solutions, for instance in physiologically compatible buffers such as Hank's solution or Ringer's solution. In addition, the compounds may be formulated in solid form and redissolved or suspended immediately prior to use. Lyophilized forms are also included.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated. Methods of coating tablets are well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound. For buccal administration the compositions may take the form of tablets or lozenges formulated in conventional manner. For administration by inhalation, the biglycan therapeutics are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays or using suppositories. For topical administration, the biglycan therapeutics are formulated into ointments, salves, gels, or creams as generally known in the art. A wash solution can be used locally to treat an injury or inflammation to accelerate healing.

In clinical settings, a gene delivery system for the therapeutic gene encoding a biglycan and/or utrophin as described herein can be introduced into a patient by any of a number of methods, each of which is familiar in the art. For instance, a pharmaceutical preparation of the gene delivery system can be introduced systemically, e.g., by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g., Chen et al. (1994) *PNAS* 91: 3054-3057). A gene encoding a biglycan protein can be delivered in a gene therapy construct by electroporation using techniques described, for example, by Dev et al. ((1994) *Cancer Treat Rev* 20:105-115).

Modes of delivering DNA to muscle cells include using recombinant adeno-associated virus vectors, such as those described in U.S. Pat. No. 5,858,351. Alternatively, genes have been delivered to muscle by direct injection of plasmid DNA, such as described by Wolff et al. (1990) *Science* 247:1465-1468; Acsadi et al. (1991) *Nature* 352:815-818; Barr and Leiden (1991) *Science* 254:1507-1509. However, this mode of administration generally results in sustained but generally low levels of expression. Low but sustained expression levels are expected to be effective for practicing the methods herein.

The pharmaceutical preparation of the gene therapy construct or polypeptide can consist essentially of the gene delivery system or polypeptide in an acceptable diluent, or can comprise a slow release matrix in which the gene delivery vehicle or compound is imbedded. Alternatively, where the complete gene delivery system can be produced intact from recombinant cells, e.g., retroviral vectors, the pharmaceutical preparation can comprise one or more cells which produce the gene delivery system.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

VII. Additional Exemplary Uses for the Biglycan Combination Therapeutics

Biglycan therapeutics can also be used as a supplement to a cell or tissue culture (e.g., system for growing organs) in combination with a second therapeutic such as a eutrophin polypeptide. Any cell type may benefit from these supplements. The amount of compound to be added to the cultures can be determined in small scale experiments, by, e.g., incubating the cells or organs with increasing amounts of a specific biglycan. Preferred cells include eukaryotic cells, e.g., muscle cells or neuronal cells.

Other preferred tissues include atrophic tissue. Thus, such tissue can be incubated in vitro with effective amounts of a biglycan therapeutic and a second therapeutic such as a eutrophin therapeutic to reverse tissue atrophy. In one embodiment, atrophic tissue is obtained from as subject, the tissue is cultured ex vivo with a biglycan therapeutic and a second therapeutic such as utrophin in an amount and for a time sufficient to reverse the tissue atrophy, and the tissue can then be readminstered to the same or a different subject.

Alternatively, the biglycan therapeutic and second therapeutic can be added to in vitro cultures of cells or tissue obtained from a subject having a muscular dystrophy, or other disease that can be treated with a biglycan therapeutic, to improve their growth or survival in vitro. The ability to maintain cells, such as brain cells or muscle cells from subjects having a muscular dystrophy or other disease, is useful, for, e.g., developing therapeutics for treating the disease.

VIII. Combination Therapeutics

In certain embodiments, biglycan is combined with a second therapeutic. In some embodiments, the second therapeutic is a utrophin polypeptide. In some embodiments, the therapeutic is an an anti-inflammatory agent, an agent that increases muscle mass, an agent that increases utrophin mRNA levels, an agent that increases utrophin protein levels, an agent that increases activity of the nNOS system, an agent that promotes repair of the muscle cell membrane, an agent that increases muscle regeneration, an agent that decreases fibrosis, and an antisense agent that promotes exon skipping in dystrophin.

The biglycan therapeutic can be combined with any appropriate anti-inflammatory agent. Exemplary anti-inflammatory agents include Rofecoxib (Vioxx) and Celecoxib (Celebrex). Other anti-inflammatory agents and classes of anti-inflammatory agents include adrenocortical steroids (cortisol, cortisone, fludrocortisone, prednisone, prednisolone, 6U-methylprednisolone, triamcinolone, betamethasone, and dexamethasone), non-steroidal agents and prodrugs (salicylic acid derivatives, i.e., aspirin); para-aminophenol derivatives, i.e., acetominophen; indole and indene acetic acids (indomethacin, sulindact and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, and gold compounds (auranofin, aurothioglucose, gold sodium thiomalate).

The biglycan therapeutic can be combined with any appropriate agent that increases muscle mass. The agent may be, for example, an antibody that inhibits myostatin, such as MYO-29 (Pfizer) or an analog or homolog thereof. Other exemplary agents that increase muscle mass include ACE-031 (Acceleron), AMG-745 (Amgen), and analogs thereof, and other agents that neutralize myostatin and related TGFl3 family members.

The biglycan therapeutic can be combined with any appropriate agent that increases utrophin mRNA levels. Exemplary agents that increase utrophin mRNA levels include SMT C1100 (Summit Corp.) which is also named BMN-195 (BioMarin) and an exogenous nucleic acid encoding utrophin.

The biglycan therapeutic can be combined with any appropriate agent that increases utrophin protein levels. Exemplary agents that increase utrophin protein levels SMT C1100 (also called BMN-195), L-arginine, and molsidomine.

The biglycan therapeutic can be combined with any appropriate agent that increases activity of the nNOS system. Exemplary agents that increase activity of the nNOS system include Tadalafil (Clalis), Vardenafil (Levitra), Sildenafil citrate (Viagra), and L-argninine.

The biglycan therapeutic can be combined with any appropriate agent that promotes repair of the muscle cell membrane. Exemplary agents that promote repair of the muscle cell membrane include recombinant dysferlin (Bansal D et al. "Dysferlin and the plasma membrane repair in muscular dystrophy." Trends Cell Biol. 2004 April; 14(4): 206-13), recombinant MG53 (Wang X et al. "Cardioprotection of ischemia/reperfusion injury by cholesterol-dependent MG53-mediated membrane repair." Circ Res. 2010 Jul. 9; 107(1):76-83. Epub 2010 May 13), or recombinant Cav3 (Cai C et al. "MG53 nucleates assembly of cell membrane repair machinery." Nat Cell Biol. 2009 January; 11(1):56-64. Epub 2008 Nov. 30).

The biglycan therapeutic can be combined with any appropriate agent that increases muscle regeneration. Exemplary agents that increase muscle regeneration include ACE-031 (Acceleron) and AMG-745 (Amgen).

The biglycan therapeutic can be combined with any appropriate agent that decreases fibrosis. Various treatments for fibrosis related disorders are known to those skilled in the art. Treatments include anti-inflammatory agents, corticosteroids, penicillamine, and colchicine. See e.g., Beers, M H, and Berkow, R, eds. The Merck Manual. 7th ed. Merck Research Laboratories, 1999. In some embodiments, anti-fibrotic therapy includes administration of profibrotic factor antagonists and/or anti-fibrotic agents. In this manner, anti-fibrotic therapy may targets fibrocyte, fibrocyte precursor, myofibroblast precursor, and/or hematopoetic monocyte precursor differentiation and fibrotic tissue formation and maintenance, for example using an inhibitory antibody. Profibrotic factors that may be targeted with antagonists as part of the therapies of the present invention include, without limitation, a transforming growth factor type β (TGF-β, including TGF-β1-5), VEGF, EGF, RANTES, members of the interleukin family (e.g., IL-1, IL-4, IL-5, IL-6, IL-8 and IL-13), tumor necrosis factor type alpha (TNF-α), platelet-derived growth factor (PDGF), basic fibroblast growth factor (bFGF), monocyte chemoattractant protein type 1 (MCP-1), macrophage inflammatory protein (e.g., MIP-1α, MIP-2), connective tissue growth factor (CTGF), endothelin-1, angiotensin-II, rennin, leptin, chemokines (e.g., CCL2, CCL12, CXCL12, CXCR4, CCR3, CCR5, CCR7), SLC/CCL21 and other factors known to promote or be related to the formation, growth, or maintenance of fibrotic tissue. In certain embodiments, anti-fibrotic therapy may include antibodies directed to one or more of the profibrotic factors. In other selected embodiments, anti-fibrotic therapy may include soluble forms of the receptor of one or more of the profibrotic factors and/or cytokines, such that the soluble receptor competes with its corresponding native cellular receptor for the target ligand. In certain embodiments, anti-fibrotic therapy may include one or more oligoribonucleotides that contain at least one sequence that is antisense with respect to one or more of the profibrotic factors and/or cytokines. In certain embodiments, the profibrotic factor antagonists can be replaced with, or augmented with, a cytokine known to have anti-fibrotic effects, such as IL-12, IL-10, IFN-γ or BMP-7 (OP-1). For instance, IFN-γ1b (Actimmune®; human interferon) is a single-chain polypeptide of 140 amino acids. It is made recombinantly in E. coli and is unglycosylated. Rinderknecht et al. (1984) J. Biol. Chem. 259:6790-6797. In some embodiments, the anti-fibrotic agent is a halofuginone analog such as HT-100 (Halo Therapeutics).

The biglycan therapeutic can be combined with any appropriate agent that promotes exon skipping in the dystrophin transcript. Exemplary agents that promote dystrophin exon skipping include AVI-4658 (AVI Pharmaceuticals), PRO51 and PRO44 (Prosensa and GSK). Antisense therapeutics mediating exon skipping are also described in (Heemskerk H et al. "Development of antisense-mediated exon skipping as a treatment for duchenne muscular dystrophy." Ann N Y Acad Sci. 2009 September; 1175:71-9.)

XI. Examples

The present invention is further illustrated by the following examples which should not be construed as limiting in any way. The contents of all cited references (including literature references, issued patents, published patent applications) as cited throughout this application are hereby expressly incorporated by reference.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, $2^{nd}$ Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Manipulating the Mouse Embryo, (Cold Spring Harbor Laboratory Press, Cold Spring Harbor, N.Y., 1986).

Example 1. Endogenous Biglycan Regulates Utrophin Expression in Immature Muscle

At postnatal day 14 (P14), utrophin is highly expressed in the perisynaptic sarcolemma (FIG. 1A) (9). To compare utrophin expression levels in the presence and absence of biglycan, we immunostained sections of muscle from bgn–/o mice and age-matched congenic controls. In all cases, the mutant and WT sections were mounted on the same slides, stained together and imaged concurrently (Materials and Methods). FIG. 1A shows that utrophin expression is decreased at the perisynaptic sarcolemma in bgn–/o muscle, whereas sarcolemmal dystrophin expression was unchanged. Quantification of 50 sarcolemmal segments from each of three animals from each genotype showed that utrophin levels were reduced by ~28% (FIG. 1B; Bgn–/o: 0.72±0.03, WT: 1.0±0.04, unpaired Student t test, P<0.0001). In contrast, there was no significant difference in the expression of dystrophin in the sarcolemma (FIG. 1C; Bgn–/o: 1.01±0.03, WT: 1.00±0.03, unpaired Student t test, P=0.76). Notably, the amount of utrophin transcript was indistinguishable in WT as compared with bgn–/o P14 muscle (text below and FIG. 1D). These results indicate that utrophin protein expression at the sarcolemma is selectively decreased in the absence of biglycan.

Example 2. RhBGN Treatment Up-Regulates Membrane-Associated Utrophin in Cultured Muscle Cells We next turned to a cell culture system to more precisely delineate the role of biglycan in regulating utrophin association with the sarcolemma. We stimulated bgn–/o myotubes with 1 nM rhBGN and assessed the levels of utrophin and γ-sarcoglycan in membrane fractions by Western blotting. As shown in FIG. 2A, rhBGN treatment up-regulates utrophin and γ-sarcoglycan protein in these membrane fractions. On the other hand, there was a reduction in utrophin transcript levels following rhBGN treatment (untreated: 1±0.10; rhBGN treated: 0.7±0.06; unpaired Student t test, P=0.02; n=6 separate experiments with three replicate flasks in each). Thus, the up-regulation of utrophin protein expression at the membrane is not associated with increases in the level of its transcript.

Figure 2:
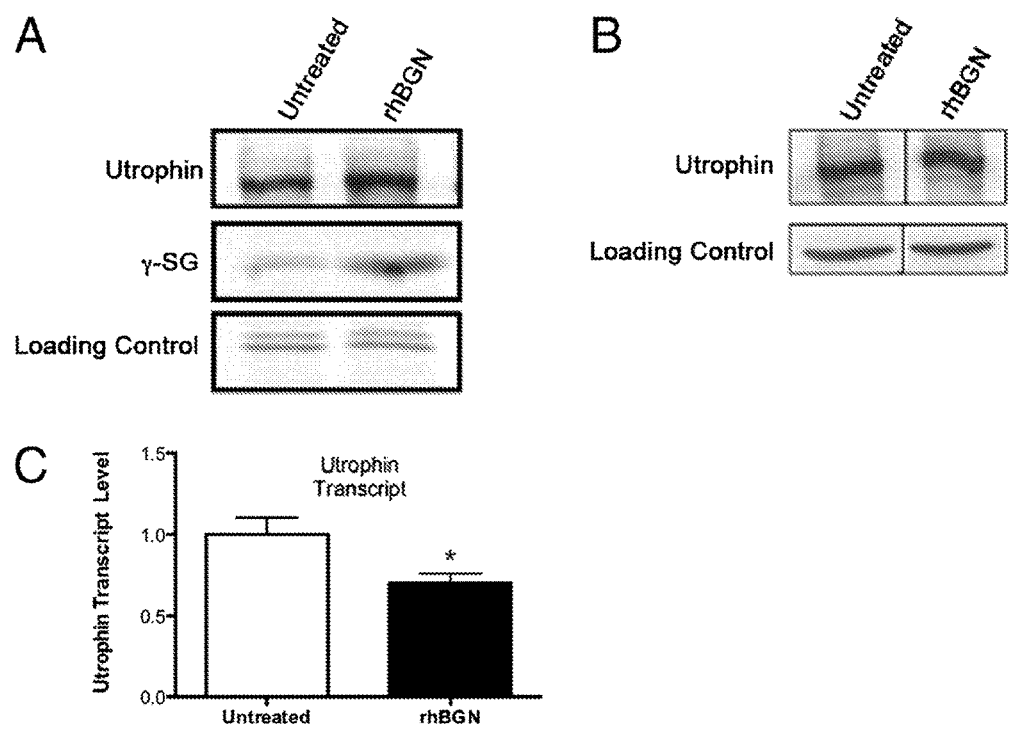
FIG. 2A-C. RhBGN treatment increases membrane-associated utrophin and γ-sarcoglycan protein in cultured myotubes. (A) Cultured bgn–/o myotubes were incubated for 8 h with either 1 nM rhBGN or vehicle as indicated. Shown are Western blots of membrane fractions probed for utrophin and γ-sarcoglycan (γ-SG). Note the increased expression of both utrophin and γ-sarcoglycan following rhBGN treatment. (B) Bgn–/o myotubes were treated as in A and whole-cell extracts were prepared. Proteins were separated by SDS/PAGE and immunoblotted for utrophin and actin (loading control). Total utrophin protein levels were similar in untreated and rhBGN treated cultures. (C) Quantitative RT-PCR analysis of untreated and rhBGN treated cultured bgn−/o myotubes. RhBGN treatment decreased utrophin transcript levels by ~30% (untreated: 1±0.10; rhBGN treated: 0.7±0.06; unpaired Student t test, P=0.02; n=6 separate experiments with three replicate flasks in each).

The results described above suggest that biglycan could regulate utrophin protein by mechanisms involving elevated translation, increased stability, and/or targeting of utrophin to the membrane. To distinguish among these possibilities, we assessed the level of total utrophin protein in control and biglycan-treated cultures. As shown in FIG. 2, total utrophin protein levels are indistinguishable in treated and untreated myotubes. The failure to detect changes in total cellular utrophin protein under conditions in which the membrane-bound fraction is increased indicates that biglycan regulates the association of utrophin with the membrane.

Example 3. Systemic Delivery of rhBGN

Figure 7:
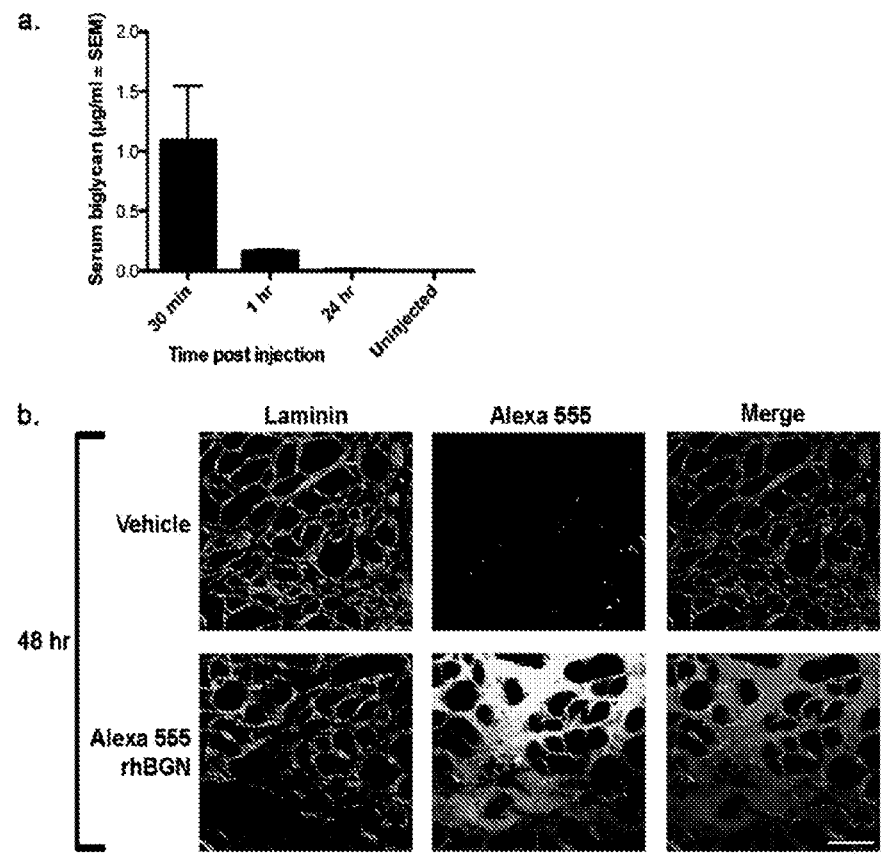
FIG. 7A-B. Systemically delivered rhBGN can be detected in the circulation and becomes localized to muscle. (A) Detection of rhBGN in serum following i.p. delivery. Mice were injected i.p. with 10 mg/kg rhBGN, and serum was collected 30 min, 1, and 24 h postinjection (n=3-4 animals/group). Two-site ELISAs were performed as described in Example 9. Biglycan (endogenous) was not detected in serum from uninjected mice. However, rhBGN was readily detected in serum following a systemic injection of the recombinant protein. (Scale bar=50 μm.) (B) Systemically delivered rhBGN becomes stably localized to muscle. Alexa 555-rhBGN (Example 9) was injected i.p. into adult mdx mice, and diaphragms were harvested 48 h later. Endogenous laminin was detected by indirect immunofluoresence. Systemically delivered Alexa 555-rhBGN is localized in the extracellular matrix surrounding the myofibers.

The role for biglycan in recruiting utrophin to the membrane, taken together with previous results, showing that both endogenous biglycan and intramuscularly delivered rhBGN can regulate DAPC proteins in vivo (15), suggesting that rhBGN could be a therapeutic agent for DMD. This experiment shows that rhBGN can be delivered systemically. A capture ELISA showed that rhBGN was readily detected in the circulation 30 and 60 min after i.p. delivery (FIG. 7A). To detect the recombinant protein in tissue, where endogenous biglycan is expressed (13), we injected animals i.p. with rhBGN conjugated to Alexa-555. As shown in FIG. 7B, this rhBGN is readily detected in the muscle extracellular matrix 48 h following injection. These observations indicate that the circulating recombinant protein partitions to muscle where it becomes stably associated with the ECM. This result is in agreement with our earlier findings that intramuscularly delivered rhBGN is stable in muscle for at least 2 wk following a single intramuscular injection in bgn–/o mice (15). This finding is also consistent with the efficacy of rhBGN observed 2 wk after a single injection in mdx mice (discussed below). Taken together, these findings indicate that rhBGN can be delivered systemically and can become localized to muscle for prolonged periods.

Example 4. RhBGN Up-Regulates Utrophin and Other DAPC Components in Mdx Mice

Figure 3:
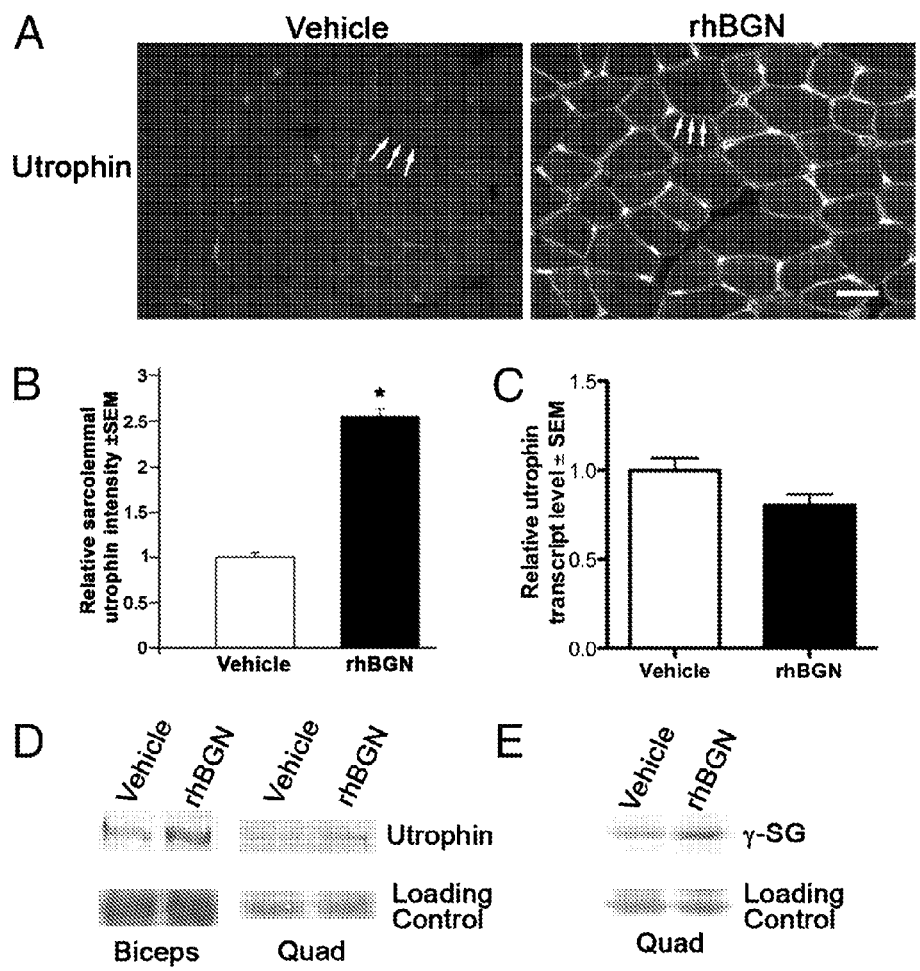
FIG. 3A-E. RhBGN treatment up-regulates utrophin at the sarcolemma of mdx mice. (A) Utrophin immunostaining of quadriceps muscles from P33 mdx littermate mice that received a single i.p. injection of either rhBGN or vehicle at P19. (Scale bar=25 μm.) (B) Levels of immunostaining at the sarcolemma (e.g., arrows in A) of peripherally nucleated fibers. A total of 100 sarcolemmal segments from each of four animals were analyzed (two littermate pairs, one rhBGN- and one vehicle-injected animal per pair). Sarcolemmal utrophin immunoreactivity was >2.5-fold higher in sections from rhBGN—as compared with vehicle-injected animals (unpaired Student t test, P<0.0001). (C) qRT PCR analysis of utrophin transcripts in from vehicle- or rhBGN-injected mdx mice. There was no significant difference in utrophin transcript levels in rhBGN treated mice compared with vehicle-injected controls (unpaired Student t test, P=0.057; n=8 vehicle- and 6 rhBGN-treated mice). (D) RhBGN treatment increases utrophin expression in muscle membrane fractions. Mdx mice from a single litter were injected at P16 and P38 (Left Pair) or P16, P38, and P63 (Right Pair) with rhBGN or vehicle. Muscles were harvested 3 wk after the last injection. (E) RhBGN treatment increases γ-sarcoglycan expression. Mdx mice were injected at 3-wk intervals starting at P14 with rhBGN or vehicle alone. Muscles were harvested at 15 wk of age and immunoblotted for γ-sarcoglycan. γ-Sarcoglycan is increased in the membrane fractions from rhBGN treated mdx mice compared with vehicle-treated animals.

We next asked whether rhBGN can up-regulate utrophin in mdx mice. A single i.p. dose of rhBGN was delivered to ~P18 mdx mice, and utrophin levels at the sarcolemma were assessed 2 wk later. Because utrophin expression increases transiently in regenerating myofibers (16) and is known to be enriched at synaptic and perisynaptic regions (8, 17), we restricted our analysis to extrasynaptic areas of nonregenerated (peripherally nucleated) myofibers. As shown in FIGS. 3 A and B, rhBGN treatment increased utrophin expression at the sarcolemma >2.5-fold in quadriceps muscle mdx mice (vehicle: 1.0±0.05, rhBGN: 2.5±0.08, unpaired Student t test, P<0.0001, n=200 sarcolemmal segments from two animals from each group).

Figure 4:
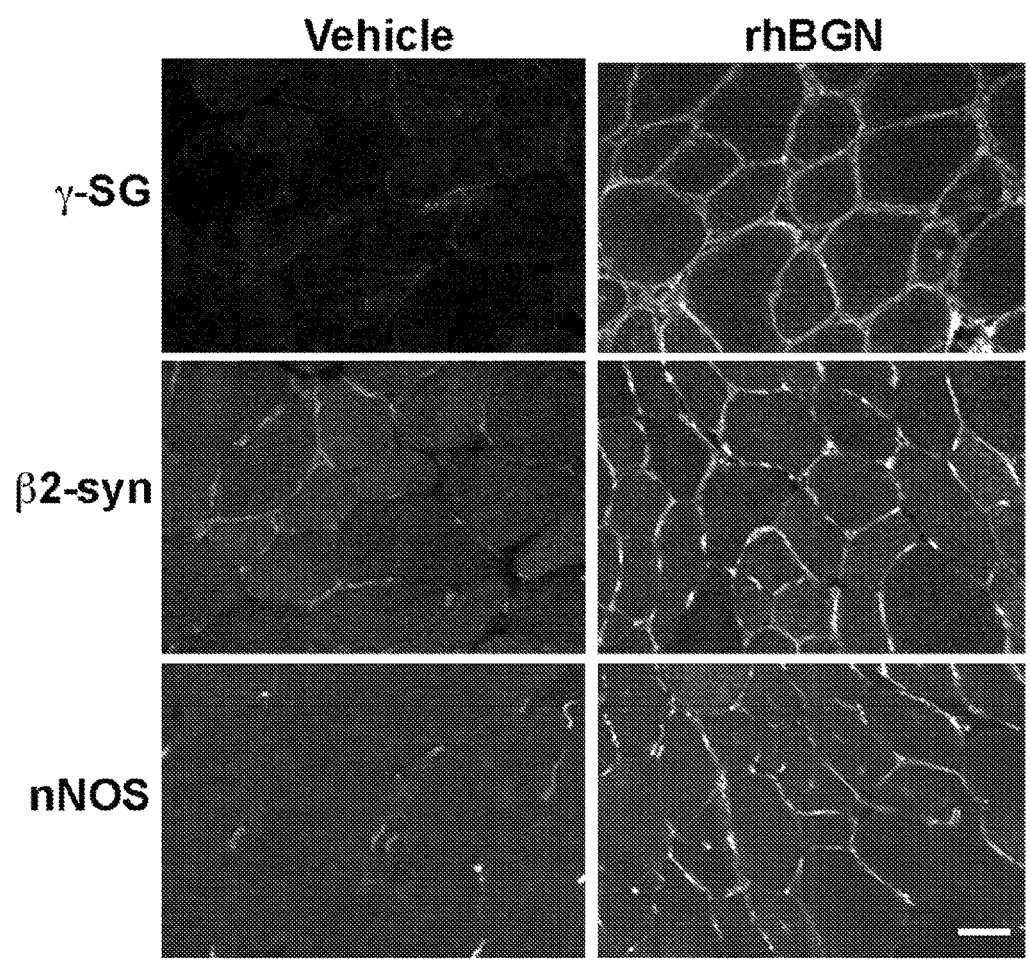
FIG. 4. RhBGN up-regulates DAPC components at the sarcolemma of mdx mice. Mdx mice were injected with rhBGN or vehicle at P18 and muscles were harvested at $^{32}$P. Sections of TA from vehicle- or rhBGN-treated animals were immunostained with antibodies to the indicated DAPC components as described in Example 9. RhBGN treatment increased the expression of sarcolemmal γ-sarcoglycan, β2-syntrophin, and nNOS in mdx mice.

Utrophin levels at the sarcolemma were also significantly increased in the tibialis anterior muscle (vehicle: 1.0±0.1, rhBGN: 1.7±0.1, unpaired Student t test; n=300 sarcolemmal segments from three animals from each group). The levels of γ-sarcoglycan, β2-syntrophin, and nNOS are also increased at the sarcolemma following a single dose of rhBGN (FIG. 4). We observed no change in α-syntrophin levels. The elevation in γ-sarcoglycan and nNOS is in agreement with our observations in cell culture, in which rhBGN treatment increased the levels of these proteins at the membrane (FIG. 2) (15). Furthermore, these proteins as well as β2 syntrophin are dysregulated in bgn–/o mice (14, 15).

Western blotting of membrane fractions provided further evidence that rhBGN treatment increased the levels of both utrophin and γ-sarcoglycan mdx mice (FIGS. 3 C and D). Taken together, these results indicate that rhBGN treatment restores the expression of utrophin and DAPC proteins to the sarcolemma.

Utrophin transcript levels were unchanged in rhBGN-treated mdx (FIG. 3C). This finding is in agreement with our in vivo and cell culture results with bgn−/o muscle (FIGS. 1 and 2), and indicates than rhBGN regulates utrophin in mdx mice at a posttranscriptional level. Finally, these results show that rhBGN effects can be observed after multiple doses spanning 6-13 wk of treatment (FIGS. 3D and E). Taken together, these immunohistochemical and biochemical results show that systemically delivered rhBGN can upregulate utrophin and other DAPC protein in the membranes of dystrophic mice.

Example 5. RhBGN Reduces Dystrophic Pathology in Mdx Mice

Figure 5:
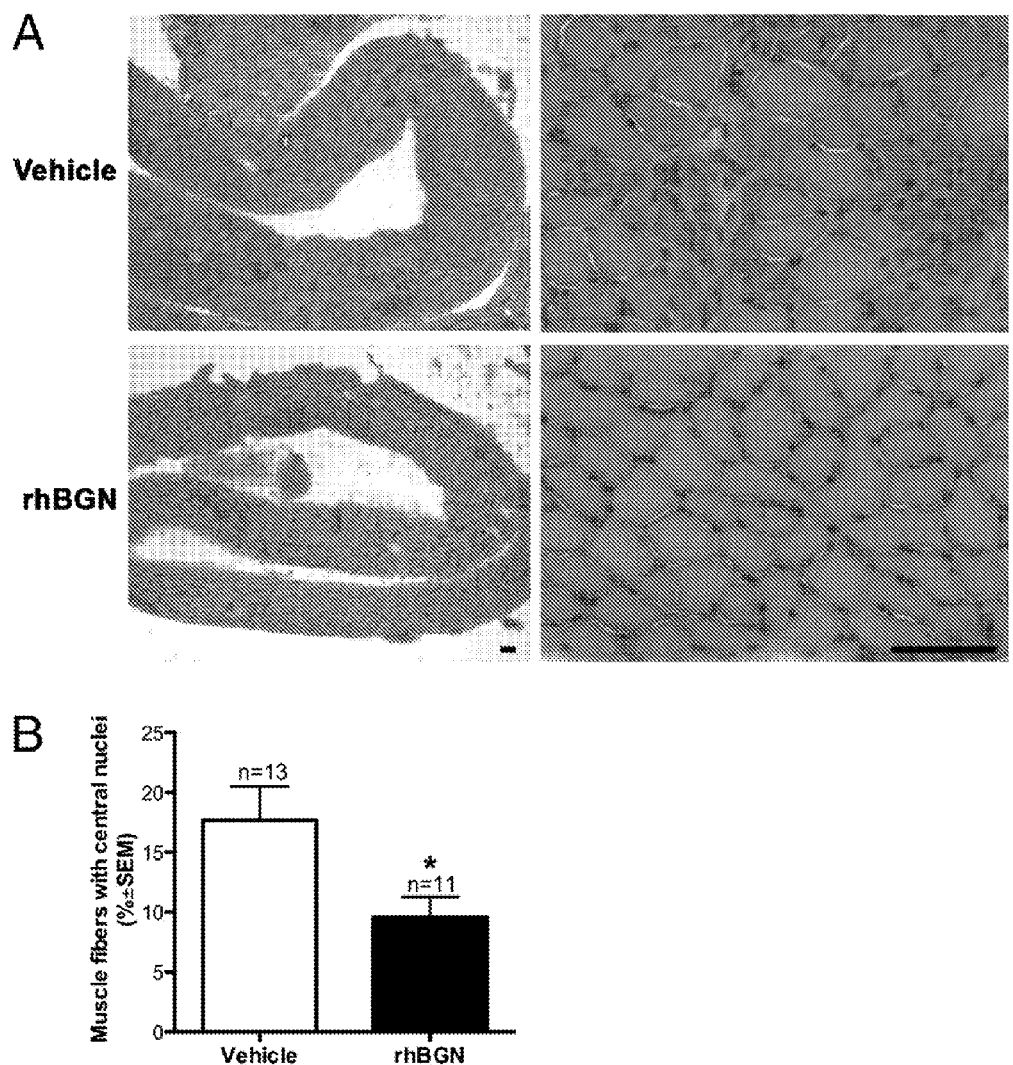
FIG. 5A-B. Systemically administered rhBGN counters dystrophic pathology in mdx mice. (A) H&E-stained sections of diaphragm from littermate mdx mice that were injected i.p. with vehicle (Upper Panels) or 100 μg rhBGN (Lower Panels) at P18 and harvested at P38. (Right Panels) Magnified view. Note the extensive areas of necrosis/regeneration and mononuclear cell infiltration in muscle from vehicle-injected as compared with rhBGN-injected mice. (Scale bars=50 μm.) (B) RhBGN administration decreases proportion of CNFs in mdx muscle compared with vehicle-injected littermates (single injection; Materials and Methods). Percentages of CNFs were determined from H&E stained diaphragm sections. RhBGN-treated mdx mice had ~50% fewer centrally nucleated myofibers as compared with vehicle-injected mdx mice (17.7%±2.8 and 9.6%±1.7 for vehicle- and rhBGN-injected animals, respectively; n=13 vehicle-injected and 11 rhBGN-injected animals; unpaired Student t test, P=0.028).
Figure 9:
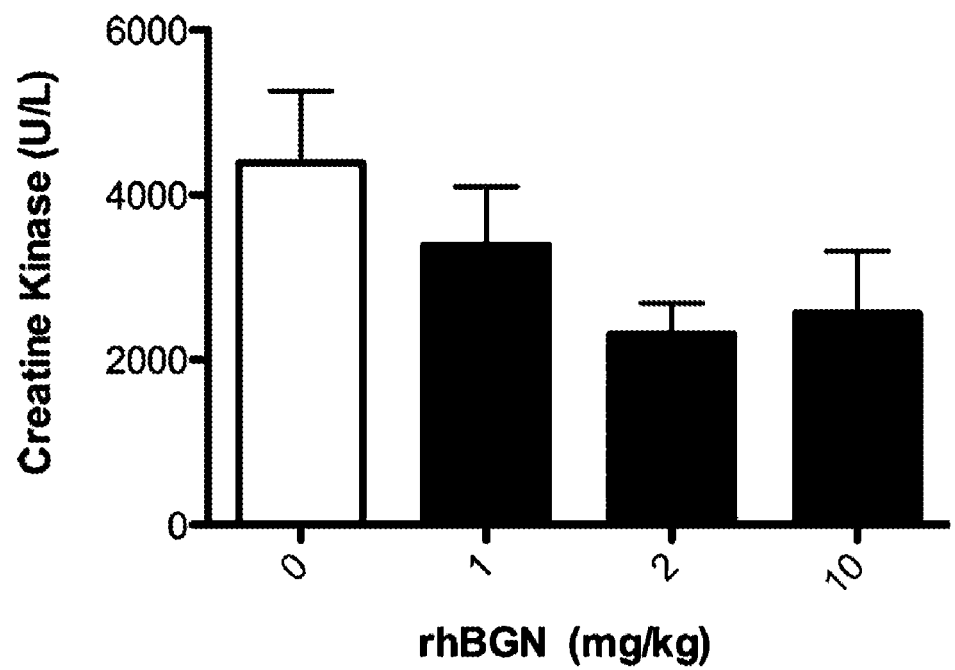
FIG. 9. Creatine kinase levels in rhBGN-treated mdx mice. Creatine kinase levels in $^{32}$P mdx mice that received a single injection of 1 mg/kg (n=23), 2 mg/kg (n=12), or 10 mg/kg (n=11) rhBGN or vehicle alone (n=24) at P18. RhBGN-treated mice showed trends of decreased CK levels, but the results did not reach statistical significance (one-way ANOVA, P>0.05).

To determine whether rhBGN counters dystrophic pathology in mdx mice, we first administered a single i.p. dose of rhBGN or vehicle alone to ~P18 mdx mice and assessed muscle histologically 2 or 3 wk later. FIG. 5A (Upper Panel) shows a section of diaphragm from vehicle-injected mice displaying characteristic dystrophic pathology including a high proportion of centrally nucleated fibers (CNFs) and foci of necrosis/regeneration and areas of mononuclear cell infiltration (18). Strikingly, rhBGN treatment resulted in a ~50% reduction in the proportion of CNFs observed in muscle from rhBGN treated mice (17.7%±2.8 and 9.6%±1.7 for vehicle- and rhBGN-injected animals, respectively; unpaired Student t test, P=0.028, n=13 vehicle- and 11 rhBGN-injected animals; FIG. 5B). We also assessed serum creatine kinase (CK) levels, a marker of muscle damage, in mice that had been given 1, 2, or 10 mg/kg rhBGN. As reported by others (18), there was considerable variation in the baseline levels of CK among experiments. Although we observed a trend toward decreased CK levels in these animals, the data did not reach statistical significance (FIG. 9). Taken together, these findings indicate that rhBGN treatment reduces dystrophic pathology in mdx mice.

Example 6. RhBGN Efficacy is Utrophin Dependent

We next asked whether the ability of rhBGN to counter dystrophic pathology in mdx mice is dependent upon utrophin. If utrophin is necessary for rhBGN action in mdx mice, the pathology of mice mutant for both utrophin and dystrophin would be unaffected by rhBGN administration. FIG. 10 shows that the histology and number of regenerated muscle fibers in mdx:utrn−/− mice were indistinguishable after a single injection of rhBGN or vehicle. Thus, at least some utrophin is necessary for high therapeutic efficacy of rhBGN.

Example 7. RhBGN Treatment Improves Muscle Function in Mdx Mice

Figure 6:
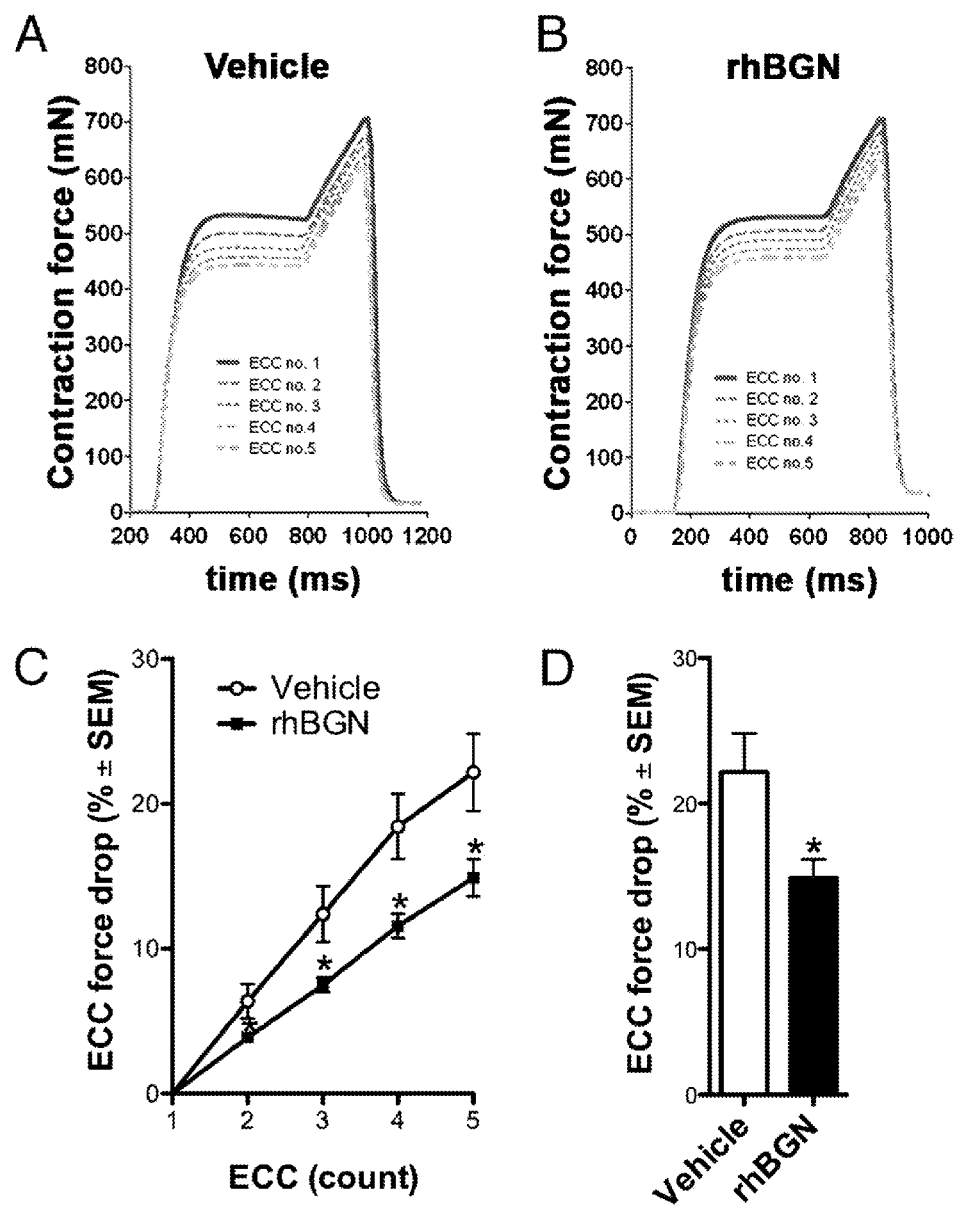
FIG. 6A-D. Physiological improvement of muscle in rhBGN-treated mdx mice. Mdx mice were injected at 3-wk intervals starting at P14 with either rhBGN (25 μg/injection; i.p.) or vehicle and tissue was harvested at 15 wk of age. Representative first to fifth ECCs of EDL muscles from mdx mice injected with (A) vehicle, or (B) rhBGN. (C) Comparisons of ECC force drop between the first and the second, third, fourth, and fifth ECC of vehicle-treated (6.4±1.2%; 12.4±1.9%; 18.4±2.3%; 22.2±7%; n=16) and rhBGN-treated (3.9±0.3%; 7.5±0.5%; 11.6±0.8%; 14.9±1.2%; n=16) mdx mice, respectively. There is significant difference in the force drop between ECCs of vehicle treated and rhBGN-treated mdx mice on the second, third, fourth, and fifth contractions (P=0.05, 0.02, 0.01, 0.02, respectively; unpaired Student t test). (D) Average force drop between first and fifth ECC in vehicle-treated and rhBGN-treated mdx mice (22.2±2.7% vs. 14.9±1.2%, respectively; P=0.02; n=16 muscles in each group; unpaired Student t test).

An effective treatment for DMD should improve muscle function. One of the primary causes of myofiber pathology, dysfunction, and death in DMD is increased susceptibility to contraction-induced damage. Such muscle damage can be assessed ex vivo by measuring the force produced after each of several successive eccentric (lengthening) contractions (ECCs) (19, 20). In these ex vivo mdx muscles, susceptibility to injury is evidenced by an increase in force drop after a series of ECCs. We injected mdx mice at 3-wk intervals (starting at P14) with either rhBGN or vehicle until 15 wk of age, and measured muscle physiology as previously described (21, 22). RhBGN treatment improved performance on muscle function measurements, as shown by a reduced amount of force drop following each consecutive ECC (FIGS. 6 C and D). This improvement was robust and statistically significant from the second ECC onward (FIG. 6C). We observed no change in other parameters of muscle function including the amount of specific force generated (Table 1). Such a profile of physiological improvement—increased resistance to damage with no change in specific force—is similar to that observed with AAV delivery of microdystrophin (R4-R23) (23) or heregulin treatment (24). Thus rhBGN treatment improves muscle function in mdx mice.

TABLE 1

Contractile properties of extensor digitorum longus (EDL) muscles

| Parameter | Control mdx (n = 16 muscles) | Treated mdx (n = 16 muscles) |
|---|---|---|
| ECC force drop 1-5 (%) | 22.2 ± 2.7 | 14.9 ± 1.2* |
| Twitch | | |
| Absolute force (mN) | 108.9 ± 5.1 | 107.3 ± 6.2 |
| Specific force (mN/mm$^2$) | 54.0 ± 3.2 | 56.6 ± 4.0 |
| Tetanus | | |
| Absolute force (mN) | 577.5 ± 27.6 | 559.4 ± 30.5 |
| Specific force (mN/mm$^2$) | 287.0 ± 18.3 | 295.0 ± 19.7 |
| EDL weight (mg) | 14.7 ± 0.7 | 14.2 ± 0.4 |
| EDL Lo (mm) | 12.4 ± 0.2 | 12.5 ± 0.1 |
| CSA (mm$^2$) | 2.07 ± 0.07 | 2.00 ± 0.08 |

Figure 8:
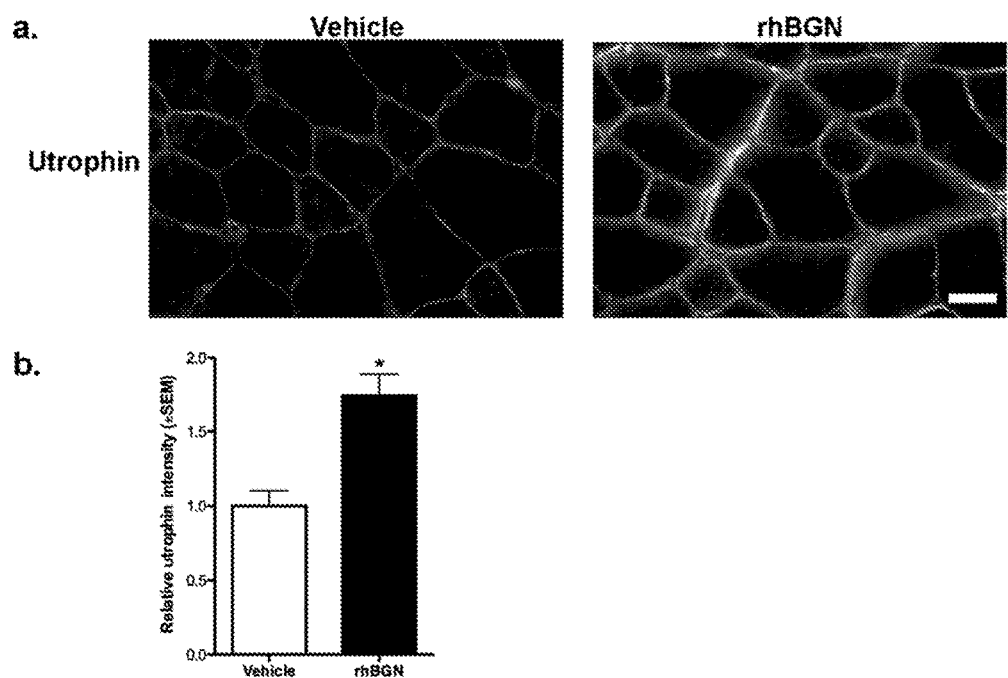
FIG. 8A-B. RhBGN treatment increases sarcolemmal utrophin expression in the tibialis anterior of mdx mice. (A) Utrophin immunostaining of TA muscles from mdx mice that received one i.p. injection of rhBGN or vehicle. Systemically delivered rhBGN increased utrophin expression in TAs of mdx mice compared with vehicle-injected mice. (B) Quantification of increased utrophin expression in TA muscle from rhBGN treated mice (1.74-fold increase, *P<0.001, Student unpaired t test; n=300 sarcolemmal segments from three muscles for each group). (Scale bar=25 μM.)

Mdx mice were injected at 3-wk intervals starting at P14 with either rhBGN (25 μg/injection, i.p.) or vehicle, and tissue was harvested at 15 wk of age. Data were collected and analyze as described in Materials and Methods and are from the same set of muscles as presented in FIG. 8 CSA, cross sectional area; ECC, eccentric contraction; Lo, muscle length.
*P = 0.02, unpaired Student t test

Example 8. RhBGN is Well Tolerated in Mdx Mice

Figure 11:
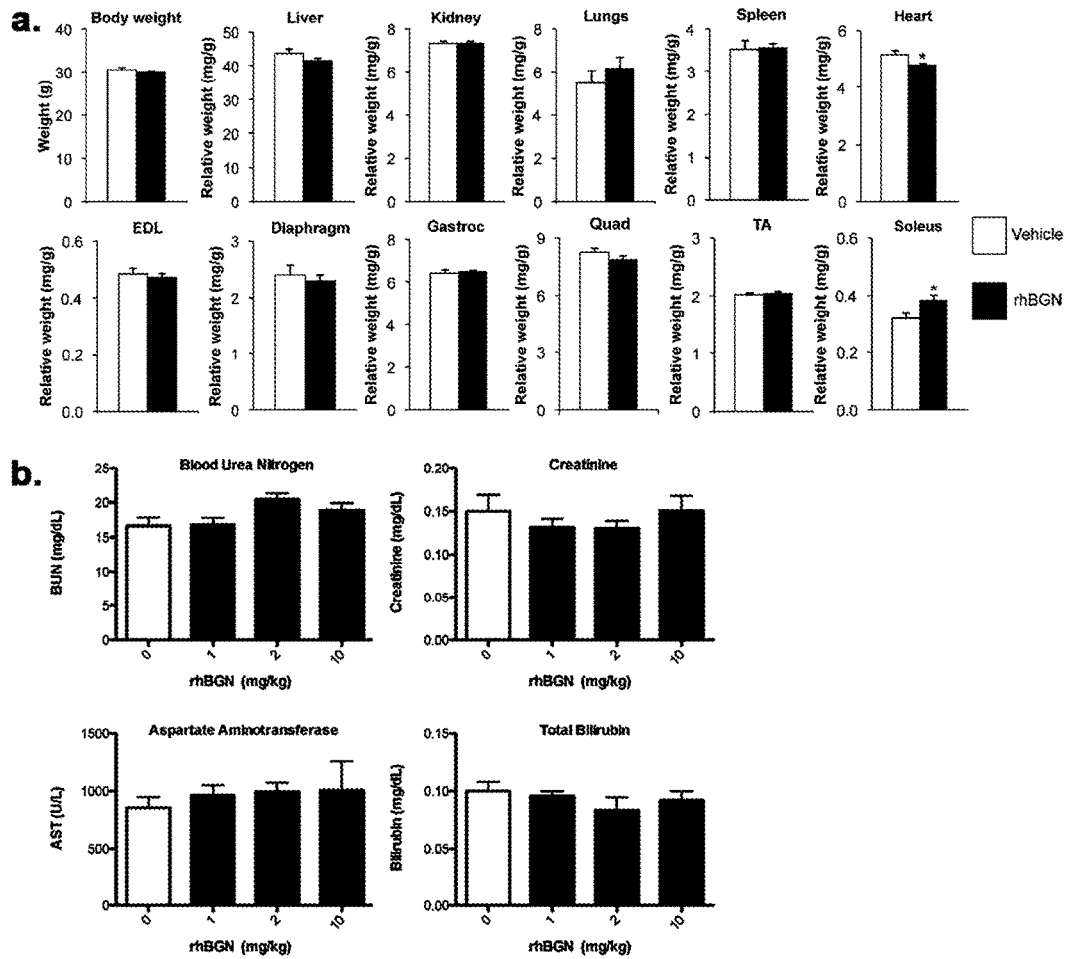
FIG. 11A-B. RhBGN is well tolerated in mdx mice. (A) P14 mdx mice were injected at 3-wk intervals for 3 mo with either rhBGN or vehicle. Tissues were harvested at 15 wk and weighed. All organ and muscle weights are plotted relative to total body weight in mg/g (n=8 animals/group; *P<0.05; unpaired Student t test). (B) Liver and kidney function in rhBGN treated mice. Serum was collected from $^{32}$P mdx mice that received an i.p. injection of 1, 2, or 10 mg/kg rhBGN or vehicle only. There were no significant changes in serum levels of BUN, creatinine, AST, or total bilirubin.
Figure 12:
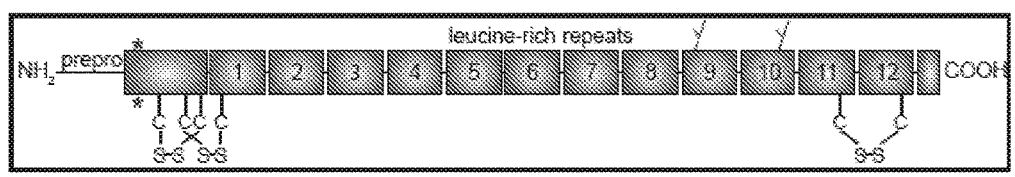
FIG. 12 is a diagram of the structure of biglycan. The prepro-region, which is absent in the mature biglycan corresponds to amino acids 1-37 of SEQ ID NO: 9; the N-terminal cysteine-rich region corresponds to amino acids 38-80 of SEQ ID NO: 9; the LRR region corresponds to about amino acids 81-314 of SEQ ID NO: 9; and the C-terminal cysteine-rich region corresponds to amino acids 315-368 of SEQ ID NO: 9. Circles represent attachment sites for chondroitin sulfate side chains. "S—S" denotes intrachain disulfide binding.

We have not observed deleterious effects of rhBGN administration in mdx mice, even after 3 mo of treatment. Organ weight is a long-standing and widely accepted measure of pharmacological toxicity (25, 26). As shown in FIG. 11A, there were no significant differences in the weights of the liver, kidney, lung, or spleen. There was an 8% decrease in the weight of the heart. Whole-animal weights were equivalent in vehicle- and rhBGN-dosed animals. Muscle weights were also unchanged with the exception of the soleus, which was 17% larger in rhBGN-treated animals. Furthermore, no indication of kidney or liver dysfunction was observed: there were no significant changes in the levels of serum creatinine, blood urea nitrogen (BUN), aspartate transaminase (AST), or bilirubin at single doses ranging from 1 to 10 mg/kg (FIG. 11B).

Example 9. Materials and Methods for Examples 1-8

Biglycan.

Recombinant, nonglycanated human biglycan (rhBGN) was produced in mammalian cells and purified as previously described (15). This form lacks GAG side chains. The Alexa 555 protein labeling kit (Invitrogen Corporation) was used to conjugate this fluor to rhBGN.

Animals and Injections.

All protocols were conducted under accordance and with the approval of Brown University's Institutional Animal Care and Use Committee. For single injections, P16-19 mice received an i.p. injection of 100 μg rhBGN in 25 μL, 20 mM Tris, 0.5M NaCl, 0.2% CHAPS, or vehicle (20 mM Tris, 0.5 M NaCl, 0.2% CHAPS). Multiply injected mice received additional i.p. injections of 100 μg rhBGN or vehicle at 3-wk intervals. Mice were harvested 13-25 d after the final injection. For tracing studies, adult mdx mice received an i.p. injection of Alexa 555-labeled rhBGN, and diaphragms were harvested 48 h later.

Histology and Immunohistochemistry.

Frozen sections were prepared and stained as previously described (15). For bgn−/o analysis, P14 congenic bgn−/o and WT sections were mounted on the same slide, immunostained simultaneously, and imaged with a cooled CCD camera in the same session using identical exposures. All comparisons of sections from injected mice (vehicle and rhBGN) were also mounted, stained and imaged together. Sections were observed using a Nikon (Melville, N.Y.) Eclipse E800 microscope and images acquired with Scanalytics IP Lab Spectrum software or NIS Elements (Nikon). Utrophin and dystrophin immunoreactivity intensity was quantified using Metamorph image analysis software (Universal Imaging) or ImageJ software (National Institutes of Health). We also observed structures in the interstitial space, which may be blood vessels, that showed increased utrophin in some experiments (FIG. 3). These structures were not included in our measurements. The average pixel intensities of sarcolemmal segments were measured, and the mean background (determined by measuring nonsarcolemmal regions from each condition) was subtracted from them. The average background levels were indistinguishable between conditions. Analysis in mdx mice was performed on quadriceps from two mice of each condition and on TAs from three mice of each condition. For scoring the percentage of CNFs, all cross-sectioned myofibers outside of necrosis/regenerative foci in H&E stained sections were counted under a 20x objective (270-1,913 fibers/muscle section).

Quantitative RT-PCR and Western Blot Analysis.

Utrophin transcript levels were measured using SYBR-Green (Invitrogen). Culture methods, preparation of lysates, and membrane fractions and analysis by Western blot were by standard procedures detailed below.

Muscle Physiology.

Mdx mice were injected i.p. with rhBGN (25 μg/animal) or vehicle every 3 wk starting at P14 and the physiological properties of the EDL muscles were analyzed ex vivo at 3.5 mo of age as described previously (21, 22). Muscle length was adjusted to achieve maximal twitch response and this length (Lo) was measured. Eccentric contraction force decrease was calculated for each tetanus of a standard ECC protocol of supramaximal stimulus 700 ms, total lengthening Lo/10; lengthening velocity 0.5 Lo/s. EDL sections were obtained and images were acquired as above. Cross-sectional area was measured using ImageJ software (National Institutes of Health).

Western Blot Analysis.

For cell membrane preparations, biglycan null myotubes were washed in PBS, scraped from tissue culture flasks and homogenized in dissection buffer (0.3M sucrose, 35 mM Tris, pH 7.4, 10 mM EDTA, 10 mM EGTA, and protease inhibitor mixture; Roche Applied Science). Samples were centrifuged at 7,000×g at 4° C. for 5 min. Membranes were then collected by centrifugation of the supernatants at 38,000×g for 60 min at 4° C. Protein concentrations were determined by the bicinchoninic acid protein concentration assay (Pierce). For total protein extraction from biglycan null myotubes, cells were washed in PBS and solubilized in RIPA lysis buffer (Santa Cruz Biotechnology) for 25 min, lysates were centrifuged at 10,000×g, and supernatants were collected. Membrane fractions from quadriceps and biceps femoris were prepared as previously described (Mercado M L, et al. (2006) Biglycan regulates the expression and sarcolemmal localization of dystrobrevin, syntrophin, and nNOS. FASEB J).

Cell or muscle fractions were separated by SDS/PAGE and proteins were transferred to nitrocellulose membranes. Total protein staining (SYPRO Ruby; Invitrogen) was visualized on a Storm Imager (Amersham Bioscience). Blots were incubated with primary antibody followed by goat anti-mouse IgG conjugated to HRP (Amersham). Signal was detected with ECL plus (Amersham) using a Storm Imager.

Quantitative RT-PCR.

RNA extraction from the biglycan null immortalized muscle cell line and quadriceps femoris muscles from injected mdx animals was performed using the TRIzol method (Invitrogen). Purified RNA was converted to cDNA using the SuperScript III First-Strand Synthesis System Kit (Invitrogen). qPCR reactions were performed using the SYBR-Green method (Invitrogen) on the ABI PRISM 7300 real-time thermocycler. Primers were designed using DS Gene primer design software (Accelrys). ATP synthase was used for normalization. Data analysis was performed using the standard curve method (Biggar W D, et al. (2004) Deflazacort in Duchenne muscular dystrophy: A comparison of two different protocols. Neuromuscul Disord 14:476-482).

The primers used were as follows: ATPSase forward: 5'-TGG GAA AAT CGG ACT CTT TG-3' (SEQ ID NO: 14); ATPSase reverse: 5'-AGT AAC CAC CAT GGG CTT TG (SEQ ID NO: 15); Utrophin forward: 5'-TCC CAA GAC CCA TTC AAC CC (SEQ ID NO: 16); Utrophin reverse: TGG ATA GTC AGT GTT TGG TTC C (SEQ ID NO: 17) (gi110431377; 3' UTR between bases 10383-12382).

Animals.

Congenic biglycan null mice on a C3H background were generated as described previously (Mercado et al 2006) and were compared with WT C3H from the Jackson Laboratory. C57BL/10ScSn-mdx/J mice were obtained from Jackson Laboratory; mdx:utrn−/− mice were bred as described (Mann C J, et al. (2001) Antisense-induced exon skipping and synthesis of dystrophin in the mdx mouse. Proc Natl Acad Sci USA 98:42-47).

Antibodies.

The following primary antibodies were used: monoclonal anti-utrophin (Vector Labs), rabbit anti-utrophin (a generous gift of S. Froehner, University of Washington, Seattle, Wash.), Q:2 rabbit anti-dystrophin (Abcam), monoclonal anti-γ-sarcoglycan (Vector), rabbit anti-laminin (Sigma), rabbit anti-β2-syntrophin (van Deutekom J C, et al. (2007) Local dystrophin restoration with antisense oligonucleotide PRO051. N Engl J Med 357:2677-2686), and rabbit anti-nNOS (Invitrogen). The specificity of the monoclonal anti-biglycan (2A5) (Mercado et al 2006) and rabbit anti-biglycan (Bowe M A, Mendis D B, Fallon J R (2000) The small leucine-rich repeat proteoglycan biglycan binds to alpha-dystroglycan and is upregulated in dystrophic muscle. J Cell Biol 148:801-810) was established by Western blot (Mercado et al. 2006, Bowe et al 2000, Rafii M S, et al. (2006) Biglycan binds to alpha- and gamma-sarcoglycan and regulates their expression during development. J Cell Physiol 209:439-447) and ELISA (Example 3); no reactivity was observed when these reagents were tested on biglycan null samples. The following secondary antibodies were used: Alexa 488 goat anti-mouse IgG and Alexa 555 goat anti-rabbit IgG (Invitrogen), HRP goat anti-mouse IgG, and HRP goat anti-rabbit IgG.

Cell Culture.

Immortalized biglycan null cells were grown as previously described (Mercado et al. 2006). Cells were differentiated for 4-5 d and then treated with 1 nm rhBGN in differentiation medium for 8 h.

Serum Chemistries.

Blood was collected by cardiac puncture from rhBGN and vehicle injected mice and spun at 3,300 RPM for 10 min to separate serum. Serum creatine kinase, BUN, creatinine, AST, and total bilirubin analyses were performed by the University of California-Davis Comparative Pathology Laboratory.

Detection of rhBGN in Serum.

Adult C57/B6 mice were injected i.p. with 10 mg/kg rhBGN, and blood was collected by cardiac puncture 30 min, 1 h, and 24 h postinjection (n=3-4 mice/condition). Control experiments showed that comparable levels of rhBGN were present in plasma (0.12 µg/mL at 1 h postinjection, n=2). For two-site ELISAs, plates were coated with mouse anti-biglycan antibody, blocked, and incubated with serum samples or standard biglycan dilutions followed by rabbit anti-biglycan and goat anti-rabbit HRP. Sensitivity of the assays was ~5 ng/mL.

Example 10. Preparation and Characterization of Different Forms of Biglycan

Biglycan is an extracellular matrix protein that is expressed as both a proteoglycan (PG) and a non-glycanated (NG) form. The proteoglycan form of biglyvan contains either one or two glycosaminoglycan side chains that can be added at either serine 5 or serine 10 (numbering is based upon the sequence of the mature polypeptide).

We used recombinant DNA technology to create a mutant form of biglycan where the two serines that can be the site of GAG addition are mutated to alanines This mutant is termed "S5A-S10A" or simply "SA". We also made a wild type construct. All were 6-HIS tagged and were based upon the human biglycan sequence. The prefix "His" is used to denote the presence of this tag.

Figure 13:
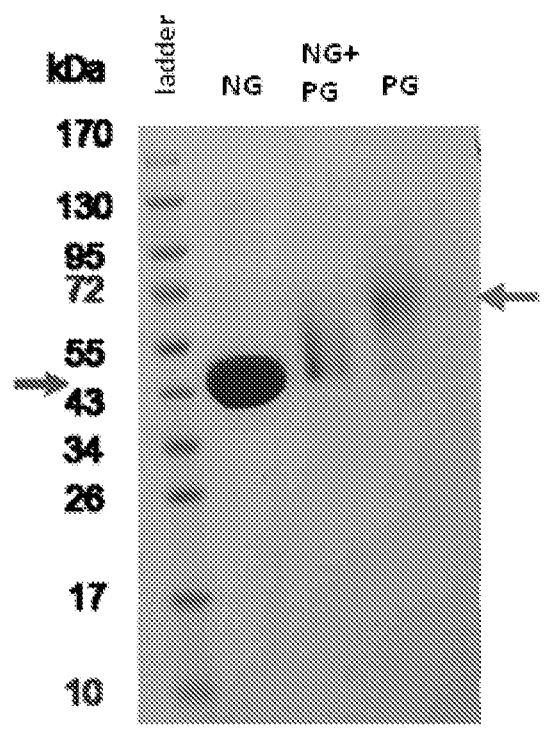
FIG. 13 shows the non-glycanated form (NG) and the proteoglycan form (PG) of biglycan. Final material was analyzed by SDS-PAGE followed by Coomassie Staining Molecular weights of the ladder are indicated to the left of the gel. The arrow to the left of the gel indicates the non-glycanated form (NG) of biglycan and the light arrow to the right of the gel indicates the proteoglycan form (PG) of biglycan.
Figure 14:
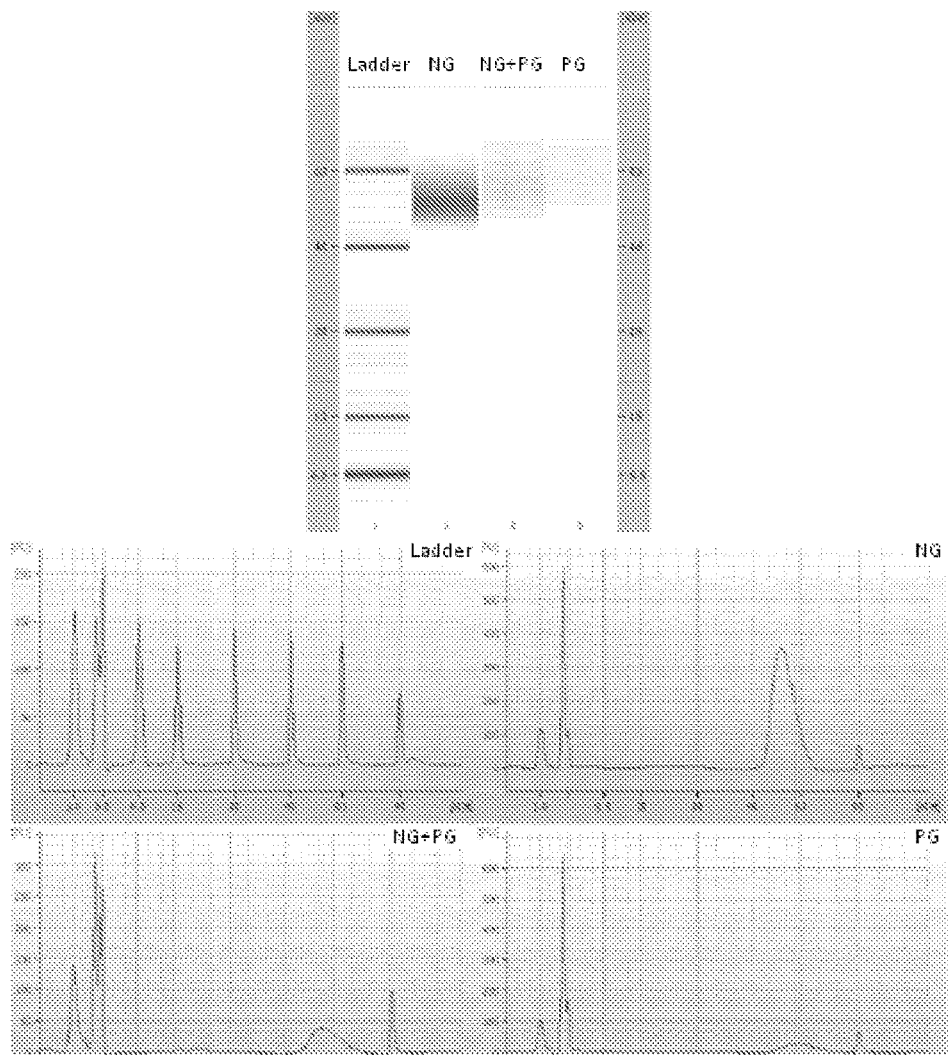
FIG. 14 shows analysis of the NG form and the PG form of biglycan. Final material was analyzed by Agilent Bioanalyzer 2100 Protein 80 chip assay. 2 µg total protein loaded per well. Top panel shows pseudo-gel image. Lower panels are electropherograms of the standards and each sample. Peaks below 4 kd and above 95 kd are system peaks used for chip calibration.

We produced and analyzed three forms of biglycan (PG, NG, S5A-S10A). All biglycan forms were made in HEK293 cells and purified by a combination of nickel and ion-exchange chromatography. These preparations were >90% pure as shown in FIGS. 13 and 14. Specifically, FIG. 13 shows the non-glycanated form (NG) and the proteoglycan form (PG) of biglycan as analyzed by SDS-PAGE followed by Coomassie Staining FIG. 14 shows analysis of the NG form and the PG form of biglycan as analyzed by Agilent Bioanalyzer 2100 Protein 80 chip assay. For the NG form of biglycan, the apparent mass was 55.9 kd and the purity was 92.6%. For the mixture of NG and PG forms of biglycan, the apparent mass was 58.9 kd, and the purity was 74%. For the PG form of biglycan, the apparent mass was 60 kd, and the purity was not determined.

Figure 15:
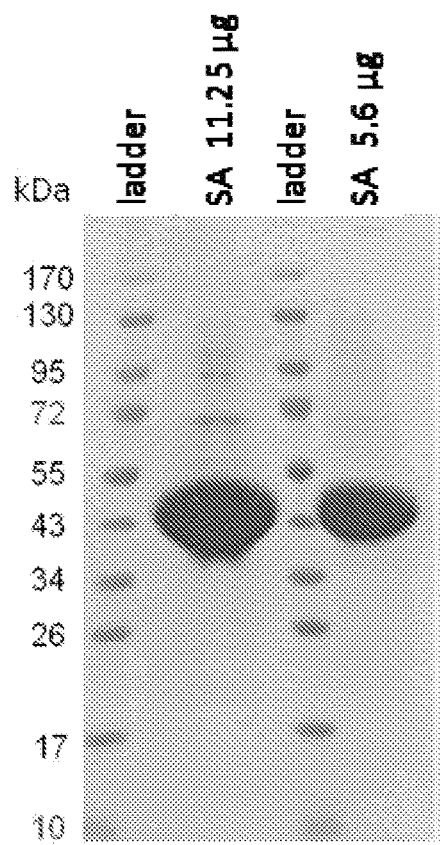
FIG. 15 shows analysis of S5A,S10A biglycan by SDS-PAGE. Final material was analyzed by SDS-PAGE followed by Coomassie staining Molecular weights of the ladder are indicated to the left of the gel. The His-Biglycan (S5A, S10A) double mutant, designated SA, was loaded on the gel in two different amounts, indicated above each lane.
Figure 16:
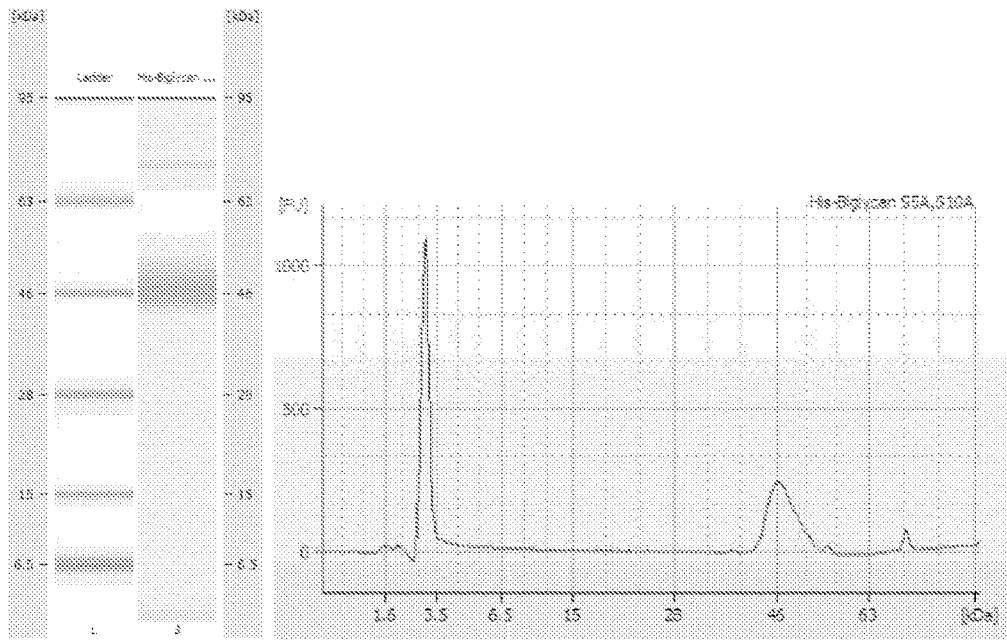
FIG. 16 shows final analysis of S5A,S10A biglycan by Agilent Bioanalyzer 2100. 2 µg of His-Biglycan (S5A, S10A) was loaded on a Protein 80 chip. Left panel is the pseudo-gel image. Right panel shows the electropherogram. Bands below 6 kd and above 95 kd are system peaks used for calibration.

The purity of the S5A-S10A preparation were also >90% as shown in FIGS. 15 and 16. Specifically, FIG. 15 shows analysis of S5A,S10A biglycan as analyzed by SDS-PAGE followed by Coomassie Staining FIG. 16 shows finaly analysis of S5A,S10A biglycan by Agilent Bioanalyzer 2100. The apparent mass was 46.3 kd and the purity was 93.2%.

Figure 17:
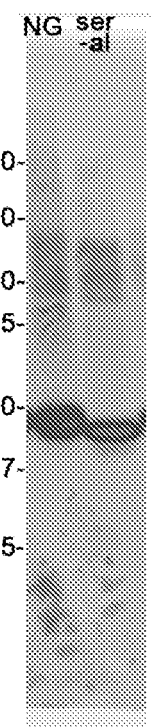
FIG. 17 shows western blot analysis of recombinant non-glycanated (NG) and S5A,S10A mutant biglycan. Samples were run on an SDS PAGE, transferred to a nitrocellulose membrane and probed with a biglycan antibody. The lane marked "ser-al" contains the S5A; 510A biglycan. The indicated amino acid positions are those of mature protein.

Western blot data shows that the S5A-S10A migrated faster on SDS gels than the NG, consistent with the presence of O-linked glycosylation on S5 and/or S10 (FIG. 17). FIG. 17 shows western blot analysis of recombinant non-glycanated (NG) and S5A,S10A mutant biglycan. Samples were run on an SDS PAGE, transferred to a nitrocellulose membrane and probed with a biglycan antibody. "ser-al" is double mutant of the both the GAG addition sites (S5A; S10A). Amino acid positions are for mature protein. Note that the mobility of the S5A; S10A mutant was faster than the (wild type) non-glycanated. These data indicate that one or both of the serines is modified in the non-glycanated. Note that the relative mobility of the NG sample is different in FIG. 15 due to gel systems use to generate this Figure as compared to that in FIGS. 13 and 14. All of the NG samples have the same mobility when separated on the same system.

Glycosyl analysis by gas chromatography of the total carbohydrates of the NG and the S5A-S10A revealed that there were major differences between them (Table 2). Notably, total glycosylation of S5A-S10A was 57% of that in NG. No iduronic or glucuronic acid was detected in NG, indicating that there was no GAG present in NG preparation. For comparison, both iduronic and glucuronic acid are highly enriched in PG proteoglycan (see Table 2 below).

Methods of determining glycosyl composition by GC-MS (Table 2) were carried out as follows. The samples (to provide ~125 µg based on undialyzed sample information) allocated for monosaccharide composition analysis were placed in screw-cap tubes, added with 10 µg inositol as internal standard, and lyophilized. Methyl glycosides then were prepared from the dried samples by methanolysis with 3 M HCl in methanol at 100° C. for 2 h followed by re-N-acetylation with pyridine and acetic anhydride in methanol (for detection of amino sugars). The preceding methanolysis and re-N-acetylation steps were repeated two times. The samples then were per-O-trimethylsilylated (TMS) with a Tri-Sil reagent (Thermo Scientific) at 80° C. for 0.5 h. These procedures were carried out as described previously in Merkle and Poppe (1994) *Methods Enzymol.* 230:1-15; York, et al. (1985) *Methods Enzymol.* 118:3-40. Analysis of the TMS methyl glycosides was performed on a Hewlett Packard Series II 5890 gas chromatograph equipped with a Supelco EC-1 fused silica capillary column (30 m×0.25 mm ID) and interfaced to a Hewlett Packard 5970 MSD.

TABLE 2

Carbohydrate analysis of biglycan glycoforms.

| Sample | Glycosyl residue | Mass (µg) | Mole % |
|---|---|---|---|
| Non-glycanated | Iduronic acid | nd | — |
| | Fucose (Fuc) | 0.21 | 17.1 |
| | Xylose (Xyl) | 0.10 | 8.7 |
| | Glucuronic Acid (GlcA) | nd | — |
| | Galacturonic acid (GalA) | nd | — |
| | Mannose (Man) | 0.46 | 34.8 |
| | Galactose (Gal) | 0.29 | 21.6 |
| | N-Acetyl Galactosamine (GalNAc) | nd | — |
| | N-Acetyl Glucosamine (GlcNAc) | 0.29 | 17.8 |
| | N-Acetyl Mannosamine (ManNAc) | nd | — |
| | Total | 1.34 | 100.0 |
| | Percent total carbohydrate by weight | 1.07 | |

TABLE 2-continued

Carbohydrate analysis of biglycan glycoforms.

| Sample | Glycosyl residue | Mass (µg) | Mole % |
|---|---|---|---|
| Proteoglycan | Iduronic acid | 5.28 | 12.5 |
| | Fucose (Fuc) | 0.86 | 1.9 |
| | Xylose (Xyl) | 0.50 | 1.2 |
| | Glucuronic Acid (GlcA) | 10.18 | 18.6 |
| | Galacturonic acid (GalA) | 0.30 | 0.5 |
| | Mannose (Man) | 0.17 | 0.3 |
| | Galactose (Gal) | 3.14 | 6.2 |
| | N-Acetyl Galactosamine (GalNAc) | 28.00 | 44.8 |
| | N-Acetyl Glucosamine (GlcNAc) | 7.92 | 12.7 |
| | N-Acetyl Mannosamine (ManNAc) | 0.89 | 1.4 |
| | Total | 57.23 | 100.0 |
| | Percent total carbohydrate by weight | 45.78 | |
| Mutant protein (S5A-S10A) | Iduronic acid | nd | — |
| | Fucose (Fuc) | 0.02 | 3.9 |
| | Xylose (Xyl) | 0.02 | 3.5 |
| | Glucuronic Acid (GlcA) | nd | — |
| | Galacturonic acid (GalA) | nd | — |
| | Mannose (Man) | 0.09 | 14.4 |
| | Galactose (Gal) | 0.02 | 2.6 |
| | N-Acetyl Galactosamine (GalNAc) | nd | — |
| | N-Acetyl Glucosamine (GlcNAc) | 0.61 | 75.5 |
| | N-Acetyl Mannosamine (ManNAc) | nd | — |
| | Total | 0.77 | 100.0 |
| | Percent total carbohydrate by weight | 0.61 | | nd = not detected.

The different forms of biglycan were further characterized by lectin blotting (FIG. 23). The recombinant bilgycan samples NG (non-glycanated), PG (proteoglycan), SA (mutant) and the controls BSA, Carboxypeptidase Y (a), Transferrin (b), and Asialofetuin (d) were stained by Ponceau S. Fetuin (c) was hardly stained by Ponceau S, perhaps because this glycoprotein is highly glycosylated and sialylated. PG was stained by MAA and DSA. SA was slightly stained by GNA and MAA and strongly stained by SNA and DSA. These results indicate that the glycans on NG and SA protein have terminal mannose, Sialic acid linked (2-6) and (2-3) to Gal or GalNAc, and Galβ(1-4)GlcNAc or terminal GlcNAc, while PG protein glycans contains Sialic acid linked (2-3) to Gal, and Galβ(1-4)GlcNAc or terminal GlcNAc structures.

Lectin blotting was carried out using DIG glycan differentiation kit (Roche). Briefly, the sample and controls were blotted onto the nitrocellulose membrane (1 µg of the sample, positive and negative control. The membranes were immersed in a blocking solution (supplied by the kit) followed by incubation with Digoxigenin-labeled lectins at 1 µg/ml in TBS. The binding activity was visualized using 750 mU alkaline-phosphatase-conjugated sheep anti-Digoxigenin as secondary antibody and nitro blue tetrazolium/5-bromo-4-chloro-3-indoyl phosphate as color developing reagent. Carboxypeptidase Y (a, GNA positive), Transferin (b, SNA positive), Fetuin (c, MAA positive) and Asialofetuin (d, PNA and DSA positive) were used as positive controls. Bovine serum albumin (BSA) was used as a negative control. Ponceau S staining was used for detection of protein on the membrane.

In addition, the position of N-linked glycosylation on different forms of biglycan was determined (FIG. 24). There are 2 potential N-glycosylation sites on SA protein; $Asn^{248}$ and $Asn^{288}$ are found within N-X-S/T consensus sequences for N-glycosylation. The SA mutant biglycan was digested with trypsin and the glycopeptides were deglycosylated with PNGase F in $H_2^{18}O$ converting the glycosylated asparagine residues into aspartic acid residues. A glycosylated peptide shows an increase of 3 Da mass compared to the corresponding non-glycosylated peptide. Glycosylation sites $Asn^{248}$ and $Asn^{288}$ of SA were shown to be glycosylated by LC-MS/MS in conjunction with a parent mass list monitoring method and database searching using the TurboSequest algorithm. The summary of N-linked glycosylation site peptides from SA is shown in FIG. 24. These results indicated that two potential N-linked glycosylation site of SA are fully glycosylated. It is worth noting that the numbering of amino acids in SA is different from that of NG. However, peptide sequence including N-glycosylation sites are identical between the two samples and the numbering in for the NG sample is consistent with that found in the UniProt database.

To perform the N-linked glycosylation analysis, fifty micrograms of the SA biglycan was reduced with 25 mM DTT for 1 h at 55° C. and carboxyamidomethylated with 90 mM iodoacetamide in the dark for 45 min. The dried dialyzed sample was resuspended in 50 mM ammonium bicarbonate ($NH_4HCO_3$) and digested with 2.5 µg of trypsin at 25° C. for 20 h. Following deactivation of trypsin at 100° C. for 5 min, the sample was then deglycosylated with 2 µg of PNGaseF in 36 µL of $^{18}O$ Water ($H_2^{18}O$) and 2 µL of 1 M $NH_4HCO_3$.

The labeled peptides were resuspended with 200 µL of mobile phase A (0.1% formic acid in water). The sample was then loaded onto a nanospray tapered capillary column/emitter (360×75×15 µm, PicoFrit, New Objective, Woburn, Mass.) self-packed with C18 reverse-phase resin (10.5 cm, Waters, Milford, Mass.) in a nitrogen pressure bomb apparatus for 10 min at 1,000 psi (~5 uL load) and then separated via a 160 min linear gradient of increasing mobile phase B at a flow rate of ~500 nL/min directly into the mass spectrometer.

LC-MS/MS analysis was performed on a LTQ Orbitrap Discoverer mass spectrometer (Thermo Scientific) equipped with a nanospray ion source. The resulting data were searched against the recombinant SA sequence using the TurboSequest algorithm (Proteome Discoverer 1.1, Thermo Scientific). The SEQUEST parameters were set to allow 30.0 ppm of precursor ion mass tolerance and 0.8 Da of fragment ion tolerance with monoisotopic mass. Tryptic peptides were allowed with up to two missed internal cleavage sites, and the differential modifications of 57.02146 Da, 15.9949 Da and 2.98826 Da were allowed for alkylated cysteine, oxidation of methionines and $^{18}O$-labeled aspartic acid, respectively.

For the NG sample, all of the above procedures were followed, except for the initial steps. Forty micrograms of NG was reduced with 25 mM DTT for 1 h at 55° C. and carboxyamidomethylated with 90 mM iodoacetamide in the dark for 45 min. The dried dialyzed sample was resuspended in 50 mM ammonium bicarbonate ($NH_4HCO_3$) and digested with 2 µg of trypsin at 25° C. for 20 h. Following deactivation of trypsin at 100° C. for 5 min, the sample was then deglycosylated with 2 µg of PNGaseF in 36 µL of $^{18}O$ Water ($H_2^{18}O$) and 2 µL of 1M $NH_4HCO_3$.

Together, these data indicate that the "non-glycanated" and SA mutant forms of biglycan do contain some carbohydrate moieties, but these differ from the proteoglycan form of biglycan.

Figure 18:
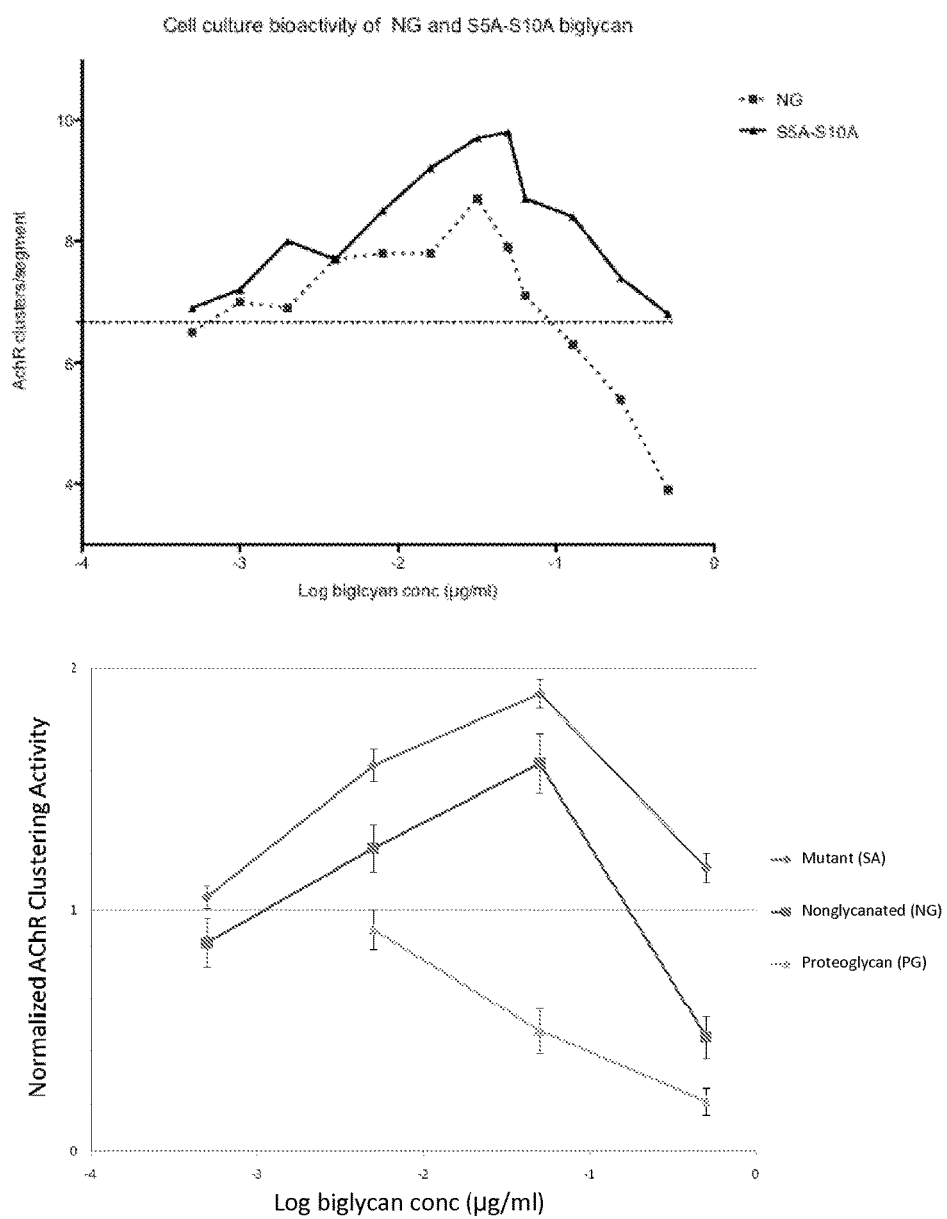
FIG. 18 shows bioactivity of NG and S5A-S10A biglycan in a cell culture bioassay. Upper panel: Primary chick myotubes were treated with 1U of purified agrin and varying concentrations of either NG or S5A-S10 biglycan. The number of AChR clusters per myotube segment was then counted in triplicate cultures as described (Nastuk et al., 1991, PMID 1660286). The level of AChR clustering induced by agrin alone is indicated by the horizontal dotted line. Lower panel: the effects of PG, NG, and S5A-S10A on AChR clustering are shown.

Bioactivity comparison of NG and S5A-S10A showed distinct activities. S5A-S10A shows a biphasic response (potentiation and depotentiation), while NG shows a triphasic response (potentiation, depotentiation, and inhibition (FIG. 18). FIG. 18 (upper panel) shows bioactivity of NG and S5A-S10A biglycan in a cell culture bioassay. Primary chick myotubes were treated with 1U of purified agrin and varying concentrations of either NG or S5A-S10A biglycan. The number of AChR clusters per myotube segment was then counted in triplicate cultures as described (Nastuk et al., 1991, PMID 1660286). The level of AChR clustering induced by agrin alone is indicated by the horizontal dotted line. Note that S5A-S10A shows potentiation at low concentrations (≤0.05 µg/ml) and depotentiation at all higher concentrations. In contrast, NG biglycan shows potentiation at ≤0.05 µg/ml, but then demonstrates depotentiation and inhibition at higher concentrations. Compared to SA and NG, PG shows a markedly different effect on AChR clustering (see lower panel).

We found that S5A-S10A was active in vivo. Systemic injection of S5A-S10A to mdx mice decreased muscle cell damage as assessed by measurement of serum Creatine Kinase levels (FIG. 19). FIG. 19 shows that S5A-S10A biglycan decreases muscle damage in mdx mice. P18 Mdx mice were injected weekly intraperitoneally for two weeks with either vehicle or S5A-S10A biglycan and the levels of serum Creatine Kinase (sCK) were measured. The levels of sCK were reduced over 2-fold in the biglycan-injected animals. ($p<0.01$; $n=4$).

FIG. 20 shows the functional efficacy of S5A-S10A rhBGN. Mdx mice were dosed with 10 mg/kg SA-rhBGN by intraperitoneal injection for 3 months at the intervals indicated. Eccentric contraction measurements were made on isolated muscle. Muscle length was adjusted to achieve maximal twitch response and this length (Lo) was measured. Eccentric contraction force decrease was calculated for each tetanus of a standard ECC protocol of supramaximal stimulus 700 ms, total lengthening Lo/10; lengthening velocity 0.5 Lo/s. A dose-frequency response in improvement of muscle function is apparent in FIG. 20.

Figure 21:
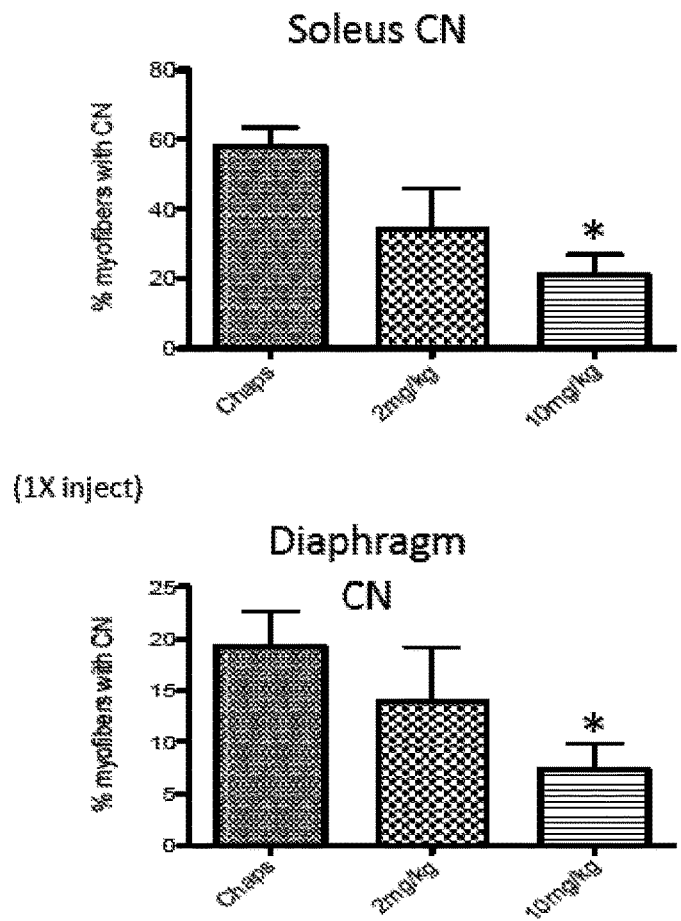
FIG. 21 shows the effects of SA-rhBGN on myofibers in vivo. Mdx mice were injected with the indicated doses of SA-rhBGN at P18 and the percentage of myofibers with centrally-localized nuclei were determined for the soleus. The same measurement was performed for diaphragm muscles two weeks later.

FIG. 21 shows the effects of SA-rhBGN on myofibers in vivo. Mdx mice were injected intraperitoneally with the indicated doses of SA-rhBGN at P18 and the percentage of myofibers with centrally-localized nuclei were determined for the soleus. The same measurement was performed for diaphragm muscles two weeks later. Frozen sections were prepared and stained as previously described (Mercado et al. Faseb J. 2006). Sections were observed using a Nikon (Melville, N.Y.) Eclipse E800 microscope and images acquired with Scanalytics IP Lab Spectrum software (Fairfax, Va.) or NIS Elements (Nikon). For scoring the percentage of centrally-localized nuclei, all cross-sectioned myofibers outside of necrosis/regenerative foci in H&E stained sections were counted under a 20× objective.

Example 11. Biglycan Administration Causes an Increase in Collagen VI Levels in a Mouse with Deficient Collagen VI Levels In biglycan null mice with wild-type collagen VI, collagen VI levels are reduced. To test the efficacy of recombinant biglycan to restore collagen VI levels in vivo in this system, a rescue approach was used. Recombinant biglycan was injected intramuscularly into biglycan null mice and the expression of collagen VI was assessed. Purified recombinant non-glycanated biglycan or proteoglycan was injected into the right quadriceps femoris muscles of five week old biglycan null animals (six animals total). Vehicle alone was injected into the left quadriceps to enable intra-animal comparison. In each case the injection site was visualized by the inclusion of 1.0% India ink in the solution. FIG. 22a shows that the injected recombinant biglycan proteoglycan appropriately localizes to the perimysium and epimysium the site of injection.

The injected biglycan had a striking effect on the expression of collagen VI in the biglycan null muscle. By four days post-injection we observed increased collagen VI expression that was tightly colocalized with areas of biglycan staining (FIG. 22b). No upregulation in collagen VI was observed in the vehicle-injected muscle (data not shown). Collagen VI expression was also upregulated by non-glycanated biglycan polypeptide (data not shown). Taken together, these results show that biglycan polypeptide can be delivered to muscle in vivo where it enhances collagen VI expression levels in the interstitium and at the muscle cell surface. Moreover, this rescue can be achieved with either the non-glycanated or proteoglycan forms of biglycan.

Example 12. Purification of S5A-S10A rhBGN

Untagged S5A-S10A rhBGN was purified according to the following scheme. First, frozen aliquots of mutant biglycan were thawed at 4° C. Once completely thawed, these samples were centrifuged to remove any particulate matter. The supernatants were then filtered using a 0.45 µm syringe filter. Filtered sample was then diluted 1:3 with deionized water.

Figure 25:
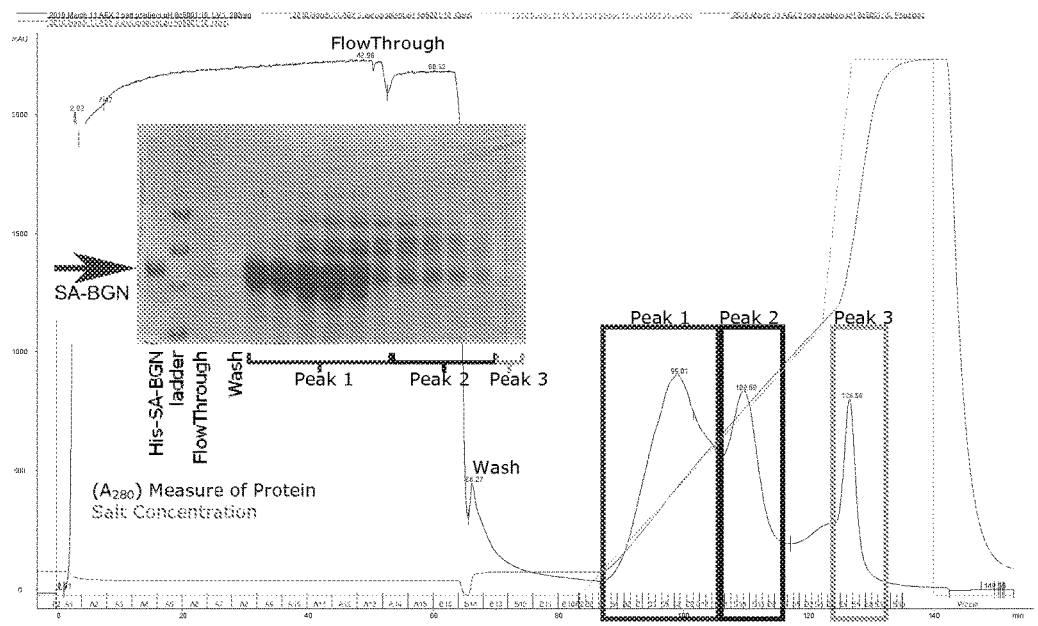
FIG. 25 shows the first step of a protocol for purifying untagged mutant biglycan. In this capture step, an anion exchange column was used. The inset coomassie gel shows that the biglycan eluted in the first peak.

Mutant biglycan was applied to 1 mL HiTrap QFF (GE LifeSciences) anion exchange column at 1 mL/min. The column was initially equilibrated in QFF A buffer (20 mM Tris pH 8.5; 50 mM NaCl). Unbound sample was washed out of the column using QFF A and 4 mL fractions were collected during sample application and wash. Mutant biglycan was eluted in the first portion of a two step gradient (0-50% B over 40 column volumes; 50-100% B over 5 column volumes; QFF B buffer consists of 20 mM Tris pH 8.5; 1 M NaCl). 1 mL fractions were collected and sampled for SDS-PAGE analysis and coomassie staining. Mutant biglycan containing fractions were pooled for the next purification step. FIG. 25 shows the elution profile and coomassie staining obtained for the anion exchange purification step.

Figure 26:
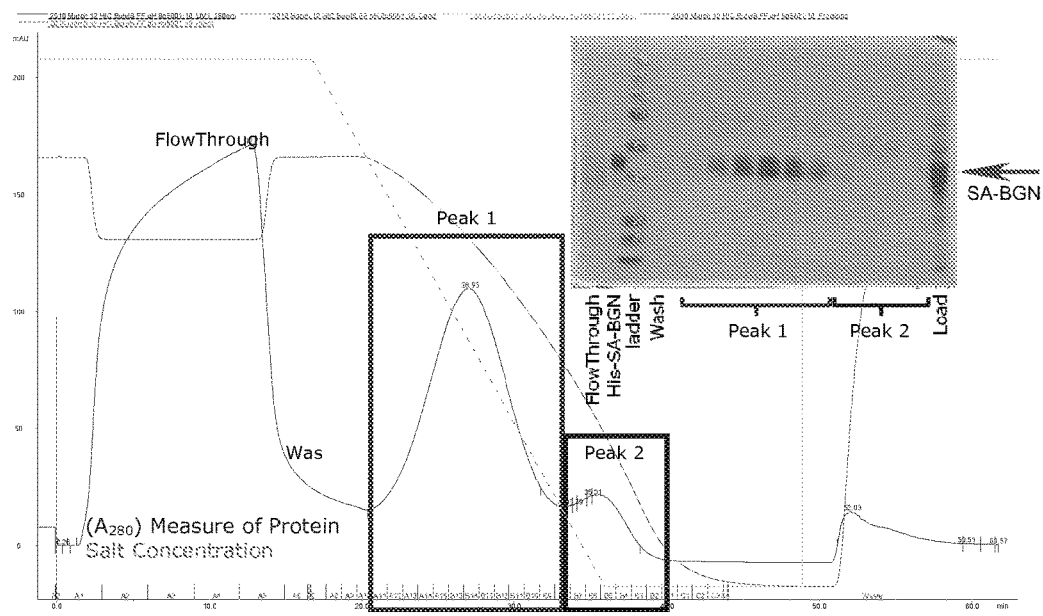
FIG. 26 shows the second step of a protocol for purifying untagged mutant biglycan. This purification step removes bulk impurities using hydrophobic interaction chromatography. The inset coomassie gel shows that the biglycan eluted in the first peak.

Pooled fractions from anion exchange were combined 1:1 with 1 M sodium citrate for a final sodium citrate concentration of 500 mM. Protein was applied to a 1 mL HiTrap ButylS FF (GE LifeSciences) HIC (hydrophobic interaction chromatography) column at 1 mL/min. The column was initially equilibrated in HIC A buffer (20 mM Tris pH 8.5; 200 mM NaCl; 500 mM Sodium Citrate). Unbound sample was washed out of the column using HIC A and 4 mL fractions were collected during sample application and wash. Mutant biglycan was eluted over a 100-0% B gradient over 20 column volumes. (HIC B buffer consists of 20 mM Tris pH 8.5; 200 mM NaCl.) 0.75 mL fractions were collected and sampled for SDS-PAGE analysis and both silver and coomassie staining FIG. 26 shows the elution profile and coomassie staining obtained for the HIC purification step.

Figure 27:
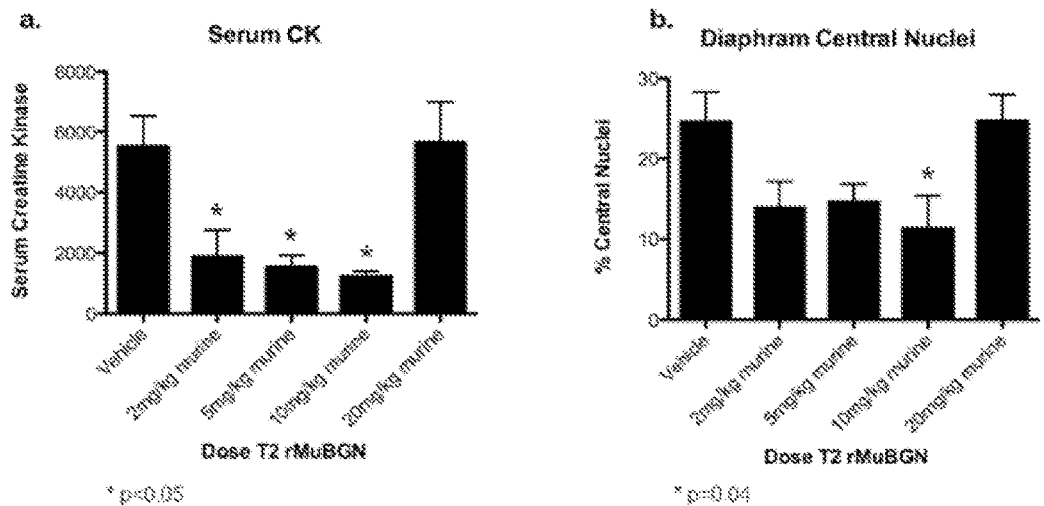
FIG. 27A-B show that untagged T2 biglycan reduces sCK and the percentage of central nuclei in mdx mice. P18 mdx mice were injected weekly (for 2 weeks) with the indicated doses of (non-tagged) T2-rMuBGN. Serum was harvested, sectioned, and stained with H&E. Montages of the sections were acquired and all the myofibers in cross-section (~600-1000 myofibers)/montage) were scored for central nuclei by workers blind to experimental condition. Treatment with untagged T2 biglycan resulted in a significant reduction in sCK levels at doses of 2, 5, and 10 mg/kg (p<0.05; 1-way ANOVA analysis with post-hoc Dunnett's Multiple Comparison Test; n=5-7 animals/group). Central nuclei were reduced by 54% in animals dosed at 10 mg/kg (p=0.04; Student's t test; n=5-7 animals/group).

Example 13. Untagged Murine Biglycan Reduces Markers of Dystrophy in Acute Studies in Mice Murine and human forms of non-tagged T2 biglycan were produced and tested. As shown in FIG. 27, T2 biglycan treatment resulted in a significant reduction in the levels of sCK and central nuclei in mdx mice that had been injected systemically (1/week for 2 wks total). There was a significant reduction in sCK at doses of 2, 5, and 10 mg/kg (p<0.05; n=5-7 animals/group; 1-way ANOVA analysis with post-hoc Dunnett's Multiple Comparison Test). At 10 mg/kg the levels of sCK was reduced 4.5-fold. The percentage of central nuclei was also reduced in treated animals. At 10 mg/kg dose there was a 54% reduction in the diaphragm CN percentage (p=0.04; Student's t test; n=5-7 animals/group). A trend towards efficacy (p~0.06) was also observed at doses of 2 and 5 mg/kg.

Figure 28:
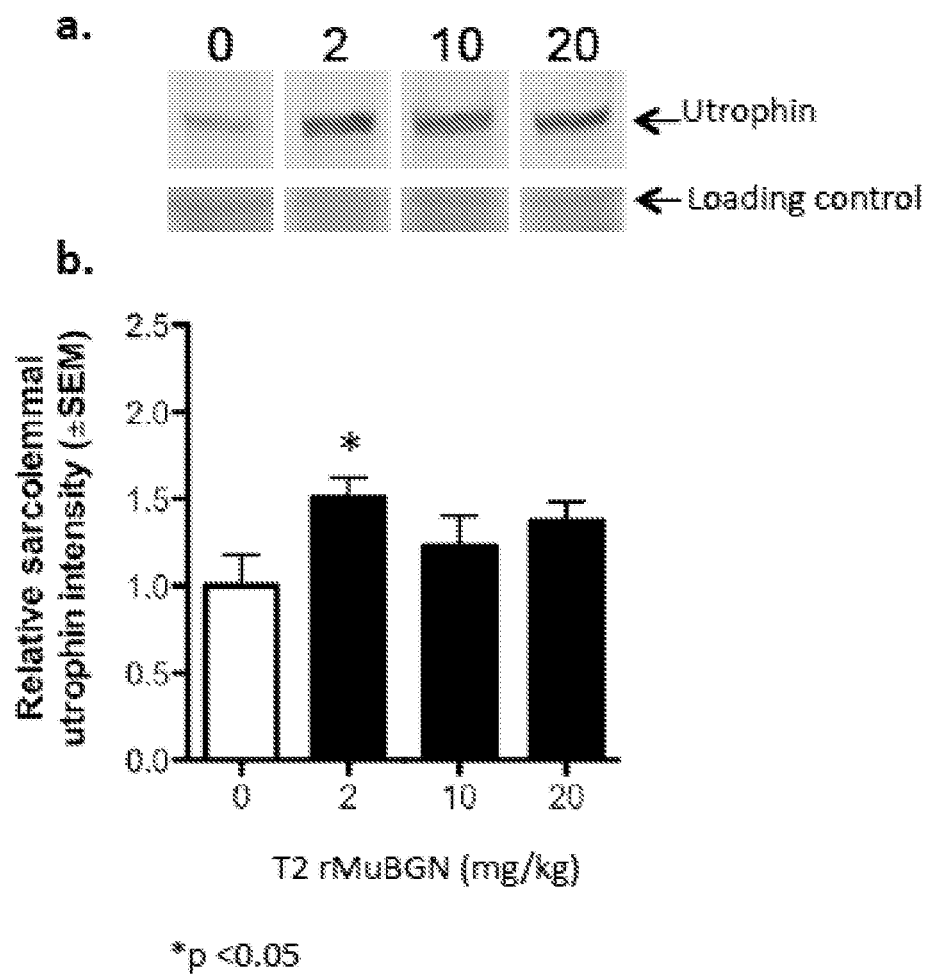
FIG. 28 shows that treatment of mdx mice with T2 biglycan increases utrophin expression. P18 mdx mice were injected weekly (for 2 weeks) with the indicated doses of (non-tagged) T2-rMuBGN. KCl-washed membrane fractions from quadriceps muscle were prepared as described (Amenta et al., 2011) and utrophin protein levels were detected by western blotting and quantified on a Storm system. Treatment with 2 mg/kg T2-rMuBGN elicited a 1.5 fold increase in utrophin expression (p<0.05; Student's t test; n=4-5 animals/group).

As shown in FIG. 28, 2 mg/kg of T2 rMuBGN elicited a 1.5-fold increase in utrophin protein levels in membrane fractions from quadriceps muscle p<0.05; n=4-5 muscles/group). In this assay we prepared KCl-washed membranes from quadriceps muscle from mice injected systemically with biglycan for (1/wk for 2 wks). Utrophin levels were quantified on western blots using a Storm imaging system.

These experiments confirm that a tag is not necessary for therapeutic efficacy of biglycan.

Figure 29:
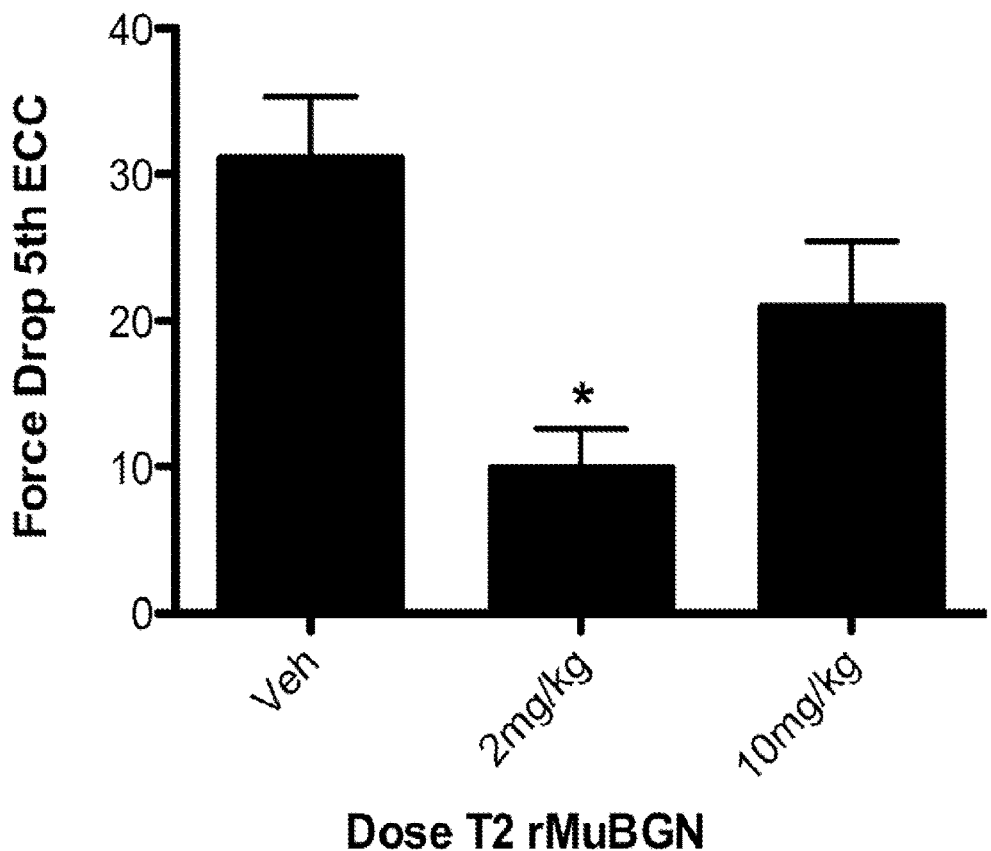
FIG. 29 shows that treatment of mdx mice with T2 biglycan improves muscle function. P18 mdx mice were injected once per week for 12 weeks with the indicated doses of T2-rMuBGN. The animals' muscle function was analyzed by Eccentric Contraction. There was a 63% improvement in muscle function in animals treated with 2 mg/kg T2-rMuBGN (p=0.007; n=3-4 animals/group).

Example 14. Untagged Murine Biglycan Reduces Dystrophic Pathology in Long-Term Studies in Mice T2 biglycan improved muscle function as judged by ECC. As shown in FIG. 29, treatment of mdx mice with 2 mg/kg of T2-rMuBGN (1/week for 12 weeks) resulted in a 63% improvement in resistance to damage by eccentric contraction as compared to vehicle-injected controls (p=0.007; n=3-4 animals/group).

Figure 30:
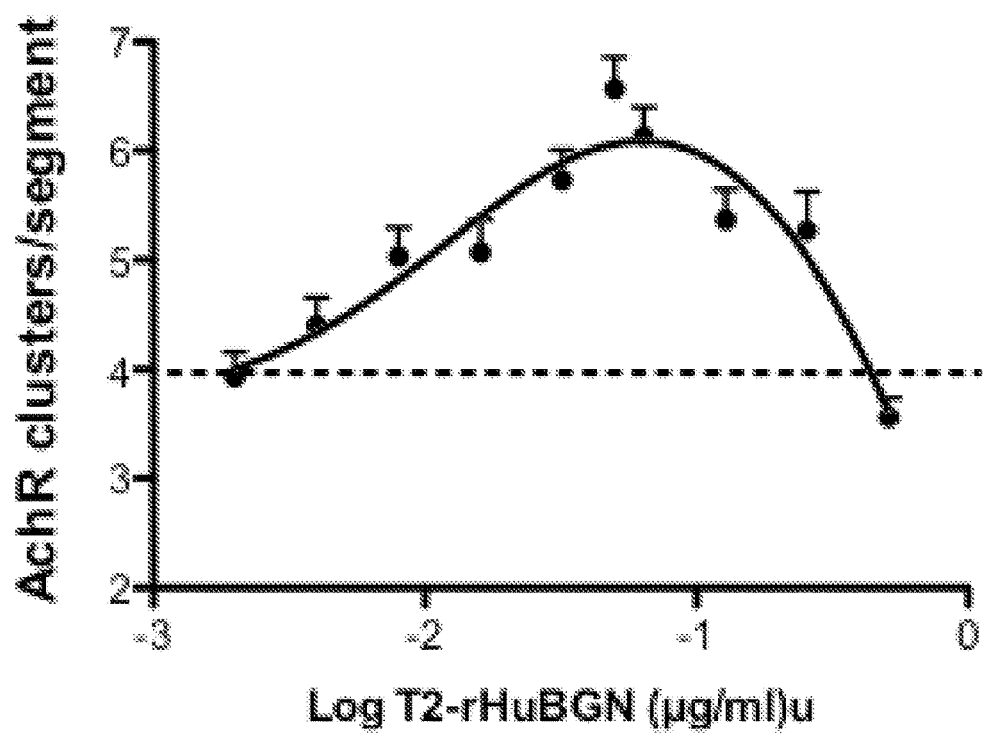
FIG. 30 shows a dose-response of T2 biglycan in a cell culture bioassay. Cultured myotubes were treated with 1U of agrin plus the indicated concentration of T2 rHuBGN for 16 hr. The number of AChR clusters per myotubes segment was then quantified for each point (n=30 segments in three coverslips). The level of activity observed with 1U of agrin alone is indicated by the dotted line. Note the 'inverted U' type dose response curve. Curve fitting was performed in Prism using a non-linear equation. Potentiation of activity was observed at concentrations ranging from 0.008 to 0.256 µg/ml (0.2 to 7.9 nM).

Example 15. Dose-Response Curve of Human Biglycan Used in a Cell Culture Biassay A range of doses of untagged T2 biglycan were assayed in a cell culture bioassay. As shown in FIG. 30, T2 biglycan potentiates agrin-induced AChR clustering activity over a 30-fold concentration range: 0.008 to 0.256 µg/ml (~0.2-7 nM). The response returns approximately to baseline at the higher dose of 0.512 µg/ml (14 nM). We have observed similar dose-response profiles with all recombinant biglycans lacking GAG side chains that we have tested including tagged rHuBGN, tagged and untagged T2 rHuBGN, and T2 rMuBGN.

Untagged T2 biglycan shows a similar "inverted-U" dose-response curve in the mouse model. FIGS. 27-29 show higher efficacy at lower doses—2 and 10 mg/kg—than at a 20 mg/kg dose. The 2 and 10 mg/kg doses showed efficacy in all three short-term assays (two week treatment)—sCK, CN, utrophin—as well as the long-term (12 week treatment) ECC measures (FIGS. 27-29). However, in both the sCK and the CN assays there was a return to baseline at the 20 mg/kg dose. A similar trend was observed in the utrophin response and the ECC. Interestingly, in these latter two cases the 2 mg/kg dose was superior to the 10 mg/kg dose.

The concordance of the in vivo and cell culture dose response profiles of T2/NG biglycan suggest that this response is due to an intrinsic pharmacological property of biglycan. One plausible explanation for such pharmacology is the presence of high and low affinity binding sites for T2/NG biglycans. It is also possible that the biphasic response reflects biglycan's action as a dimer (Scott et al., JBC 2006). The dose-response curve could reflect a preferred concentration at which the dimer is able to cross-link its ligand(s).

Moreover, together, Examples 13-15 illustrate both human biglycan and mouse biglycan produce physiologically relevant effects in the mouse model. These experiments indicate that biglycan can retain its therapeutic activity despite some amino acid sequence variation.

EQUIVALENTS

Those skilled in the art will recognize, or be able to ascertain using no more than routine experimentation, many equivalents of the specific embodiments of the invention described herein. Such equivalents are intended to be encompassed by the following claims.

We claim:

1. A method of treating a muscular dystrophy in a patient in need thereof, the method comprising:
   (i) determining that a patient has a utrophin deficiency by measuring a level of membrane-associated utrophin at the sarcolemma in a sample of muscle cells from the patient and comparing with a reference value, wherein the utrophin deficiency is characterized by a decreased level of utrophin protein or activity;
   (ii) administering a first dose of a biglycan polypeptide to the patient, wherein the biglycan polypeptide comprises an amino acid sequence corresponding to amino acids 38-365 of SEQ ID NO: 11; and
   (iii) measuring the level of membrane-associated utrophin at the sarcolemma in a sample of muscle cells from the patient; and if the level of utrophin measured in (iii) is increased relative to the level of utrophin determined in (i), then
   (iv) administering a second dose of the biglycan polypeptide.

2. A method of treating a muscular dystrophy in a patient in need thereof, the method comprising:
   (i) determining that a patient has a utrophin deficiency by measuring the level of membrane-associated utrophin at the sarcolemma in a sample of muscle cells from the patient and comparing with a reference value, wherein the utrophin deficiency is characterized by a decreased level of utrophin protein or activity;
   (ii) administering a dose of a biglycan polypeptide to the patient to increase the level of utrophin at the sarcolemma in a patient in need thereof, wherein the biglycan polypeptide comprises an amino acid sequence corresponding to amino acids 38-365 of SEQ ID NO: 11; and
   (iii) measuring the level of membrane-associated utrophin at the sarcolemma in another sample of muscle cells from the patient.

3. A method of treating a muscular dystrophy in a patient in whom a utrophin deficiency characterized by a decreased level of utrophin protein or activity has been determined by measuring the level of membrane-associated utrophin at the sarcolemma in a sample of muscle cells from the patient and comparing with a reference value, comprising administering a dose of a biglycan polypeptide to the patient, wherein the biglycan polypeptide comprises an amino acid sequence corresponding to amino acids 38-365 of SEQ ID NO: 11, wherein the level of membrane-associated utrophin at the sarcolemma of muscle cells in the patient is increased after administration of the biglycan polypeptide.

* * * * *